(12) United States Patent
Kim et al.

(10) Patent No.: US 11,548,915 B2
(45) Date of Patent: *Jan. 10, 2023

(54) COMPOSITION FOR OVERCOMING RESISTANCE TO EGFR-TARGETING AGENT

(71) Applicant: Pinetree Therapeutics, Inc., Cambridge, MA (US)

(72) Inventors: Yong Sung Kim, Suwon-si (KR); Ye Jin Kim, Busan (KR)

(73) Assignee: Pinetree Therapeutics, Inc., Cambridge, MA (US)

( * ) Notice: Subject to any disclaimer, the term of this patent is extended or adjusted under 35 U.S.C. 154(b) by 838 days.

This patent is subject to a terminal disclaimer.

(21) Appl. No.: 16/081,342

(22) PCT Filed: Mar. 28, 2017

(86) PCT No.: PCT/KR2017/003365
§ 371 (c)(1),
(2) Date: Aug. 30, 2018

(87) PCT Pub. No.: WO2017/171373
PCT Pub. Date: Oct. 5, 2017

(65) Prior Publication Data
US 2019/0062375 A1  Feb. 28, 2019

(30) Foreign Application Priority Data

Mar. 29, 2016 (KR) .......... 10-2016-0037876
Mar. 24, 2017 (KR) .......... 10-2017-0037741

(51) Int. Cl.
| | | |
|---|---|---|
| *C07K 7/08* | (2006.01) | |
| *C07K 16/28* | (2006.01) | |
| *A61K 39/395* | (2006.01) | |
| *A61K 38/17* | (2006.01) | |
| *A61K 38/08* | (2019.01) | |
| *C07K 14/71* | (2006.01) | |
| *A61K 39/00* | (2006.01) | |

(52) U.S. Cl.
CPC ........... *C07K 7/08* (2013.01); *A61K 38/08* (2013.01); *A61K 38/1709* (2013.01); *A61K 39/39558* (2013.01); *C07K 14/71* (2013.01); *C07K 16/2863* (2013.01); *A61K 2039/505* (2013.01); *A61K 2039/572* (2013.01); *C07K 2317/73* (2013.01); *C07K 2317/76* (2013.01); *C07K 2317/92* (2013.01); *C07K 2319/00* (2013.01); *C07K 2319/30* (2013.01); *C07K 2319/33* (2013.01)

(58) Field of Classification Search
None
See application file for complete search history.

(56) References Cited

FOREIGN PATENT DOCUMENTS

| KR | 10-2014-0138539 A | 12/2014 |
| KR | 10-2015-0086819 A | 7/2015 |
| KR | 10-1551306 B1 | 9/2015 |

OTHER PUBLICATIONS

Tame (J. Comput. Aided Mol. Des. Mar. 1999; 13 (2): 99-108).*
Dixon (Proteins. 1997; Suppl 1: 198-204).*
Lensink et al. (Proteins. 2007; 69: 704-718).*
Almagro & Fransson, Frontiers in Bioscience 2008; 13:1619-33.*
De Genst et al., Developmental and Comparative Immunology, 2006, 30:187-98.*
Ward et al. (Nature, 1989, 341:544-546).*
Barthelemy et al. (Journal of Biological Chemistry, 2008, 283:3639-3654).*
Choi et al., 2011, Molecular BioSystems, 2011, 7:3327-334.*
Griffiths et al. (The EMBO Journal, 1993, 12:725-734).*
Klimka et al., British Journal of Cancer, 2000, 83:252-260.*
Beiboer et al. (Journal of Molecular Biology, 2000, 296:833-849).*
Pirker, Robert (TLCR, 1(4):269-275, 2012).*
Ye-Jin Kim, et al., "Immunoglobulin Fc-fused, neuropilin-1-specific peptide shows efficient tumor tissue penetration and inhibits tumor growth via anti-angiogenesis", Journal of Controlled Release, 2015, pp. 56-68, vol. 216.
Zhiguo Chen, et al., "A Human IgG-like Bispecific Antibody Co-targeting Epidermal Growth Factor Receptor and the Vascular Endothelial Growth Factor Receptor 2 for Enhanced Antitumor Activity", Cancer Biology and Therapy, Dec. 15, 2015, pp. 139-150, vol. 17, No. 2.
Y-J Kim, et al., "Co-targeting of EGF receptor and neuropilin-1 overcomes cetuximab resistance in pancreatic ductal adenocarcinoma with integin β1-driven Src-Akt bypass signaling", Oncogene, Oct. 31, 2016, pp. 1-10.

(Continued)

*Primary Examiner* — Brad Duffy
(74) *Attorney, Agent, or Firm* — United One Law Group LLC; Kongsik Kim; Jhongwoo Peck

(57) ABSTRACT

The present invention relates to methods of overcoming the resistance to an EGFR (Epidermal Growth Factor Receptor)-targeting antibody through a peptide that binds specifically to neuropilin-1 (NRP1). Moreover, the present invention relates to a fusion antibody in which a peptide that binds specifically to NRP1 is fused to an EGFR-targeting antibody, and to a composition of overcoming the resistance to an EGFR-targeting antibody alone by co-administration of the EGFR-targeting antibody and an NRP1-binding peptide-fused Fc. In addition, the fusion antibody according to the present invention, in which the NRP1-specific binding peptide is fused to an EGFR-targeting antibody, overcomes the resistance to the EGFR-targeting antibody alone in pancreatic cancer. Furthermore, the fusion antibody, in which the NRP1-specific binding peptide is fused to the EGFR-targeting antibody, also overcomes resistance to the EGFR-targeting antibody alone even in lung cancer. Thus, the NRP1-specific binding-fused EGFR-targeting antibody according to the present invention may be highly effective in the treatment of various tumors resistant to EGFR-targeting antibody alone.

14 Claims, 23 Drawing Sheets

Specification includes a Sequence Listing.

(56) References Cited

OTHER PUBLICATIONS

Melissa Oliveira-Cunha, et al., "Epidermal Growth Factor Receptor in Pancreatic Cancer", Cancers, 2011, pp. 1513-1526, vol. 3.
Deric L. Wheeler, et al., "Understanding resistance to EGFR inhibitors—impact on future treatment strategies", Nat. Rev. Clin. Oncol., Sep. 2010, pp. 493-507, vol. 7, No. 9.
Curtis R. Chong, et al., "The quest to overcome resistance to EGFR-targeted therapies in cancer", Nat. Med., Nov. 2013, pp. 1389-1400, vol. 19, No. 11.
Sreenath V. Sharma, et al., "Epidermal growth factor receptor mutations in lung cancer", Nature Reviews, Cancer, Mar. 2007, pp. 169-181, vol. 7.
Floriana Morgillo, et al., "Mechanisms of resistance to EGFR-targeted drugs: lung cancer", ESMO Open Access, 2016, Review, pp. 1-11.
Mark A. Socinski, "Antibodies to the Epidermal Growth Factor Receptor in Non-Small Cell Lung Cancer: Current Status of Matuzumab and Panitumumab", Clin Cancer Res, Aug. 1, 2007, pp. 4597-4601, vol. 13, No. 15 Suppl.
Christel Larbouret, "In Pancreatic Carcinoma, Duel EGFR/HER2 Targeting with Cetuximab/Trastuzumab Is More Effective than Treatment with Trastuzumab/Erlotinib or Lapatinib Alone: Implication of Receptors' Down-regulation and Dimers' Disruption", Neoplasia, Feb. 2012, pp. 121-130, vol. 14, No. 2.
Matthew H. Wong, et al., "Contargeting of Epidermal Growth Factor Receptor and PI3K Overcomes PI3K-Akt Oncogenic Dependence in Pancreatic Ductal Adenocarcinoma", Clinical Cancer Research, Cancer Therapy: Preclinical, Aug. 1, 2014, pp. 4047-4058, vol. 20, No. 15.
Laetitia Sequin, et al., "An integrin $\beta_3$-KRAS-RalB complex drives tumor sternness and resistance to EGFR inhibition", Nature Cell Biology, May 2014, pp. 457-468, vol. 16, No. 5.
Hou-Fu Guo, et al., "Neuropilin Functions as an Essential Cell Surface Receptor", The Journal of Biological Chemistry, Dec. 4, 2015, pp. 29120-29126, vol. 290, No. 49.
Gerald J. Prud'Homme, et al., "Neuropilins are multifunctional coreceptors involved in tumor initiation, growth, metastasis and immunity", Oncotarget, Sep. 2012, pp. 921-939, vol. 3, No. 9.
Mathieu Berge, et al., "Neuropilin-1 is upregulated in hepatocellular carcinoma and contributes to tumor growth and vascular remodeling", Journal of Hepatology, 2011, pp. 866-875, vol. 55.
Tse-Ming Hong, et al., "Targeting Neuropilin 1 as an Antitumor Strategy in Lung Cancer", Human Cancer Biology, Aug. 15, 2007, pp. 4759-4768, vol. 13, No. 16.
Rina Kanda, et al., "Erlotinib Resistance in Lung Cancer Cells Mediated by Integrin $\beta$1/Src/Akt-Driven Bypass Signaling", Cancer Research, Oct. 15, 2013, pp. 6243-6253, vol. 73, No. 20.
Philip A. Philip, et al., "Phase III Study Comparing Gemcitabine Plus Cetuximab Versus Gemcitabine in Patients With Advanced Pancreatic Adenocarcinoma: Southwest Oncology Group-Directed Intergroup Trial S0205", Journal of Clinical Oncology, Aug. 1, 2010, pp. 3605-3610, vol. 28, No. 22.
International Search Report for PCT/KR2017/003365 dated Jun. 26, 2017 [PCT/ISA/210].

\* cited by examiner

[Figure 1a]
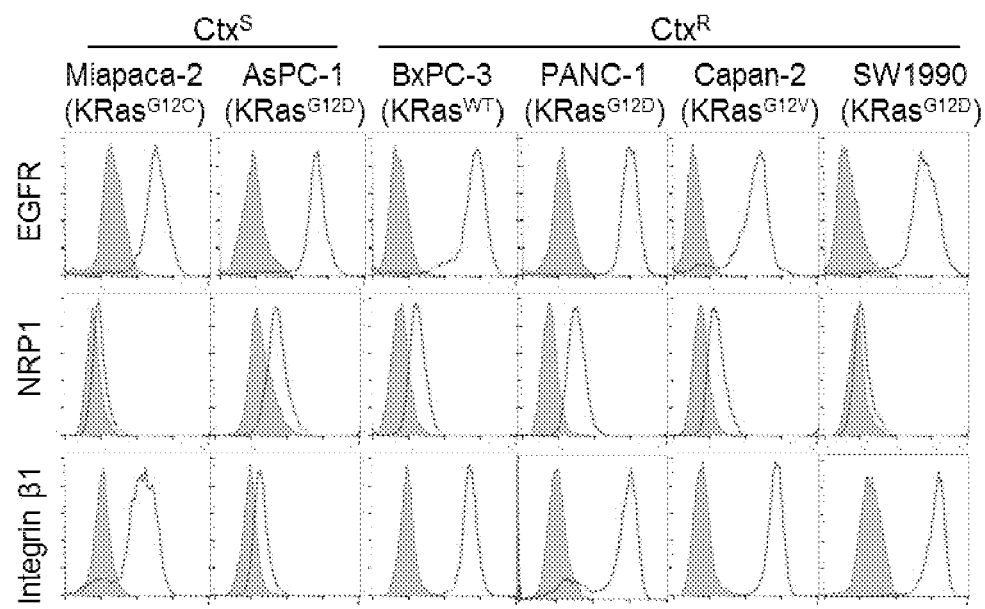
[Figure 1b]
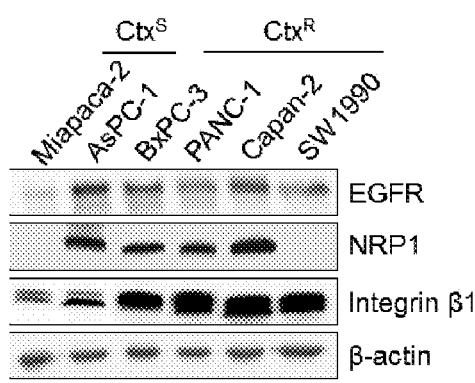

[Figure 1c]
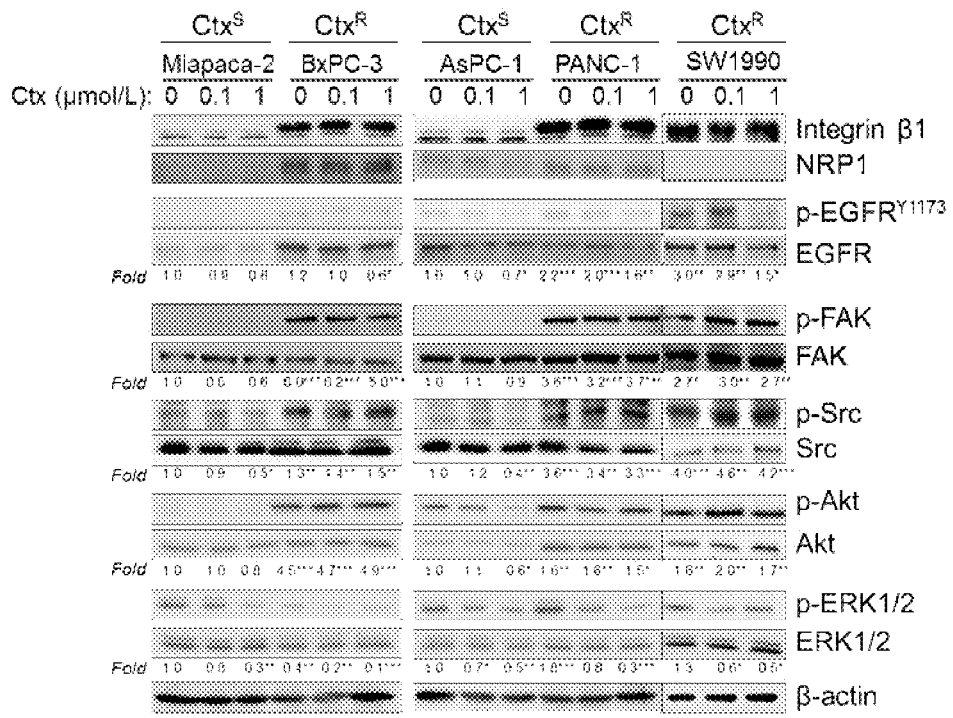
[Figure 2a]
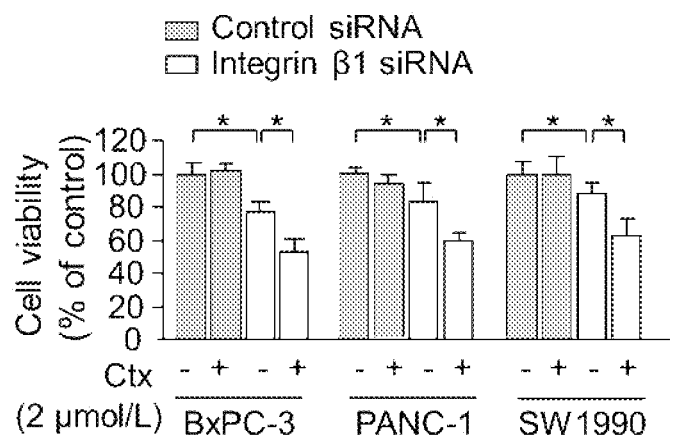

[Figure 2b]
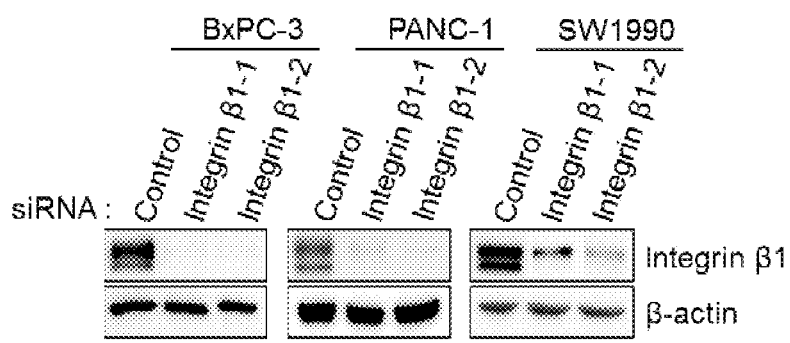
[Figure 2c]
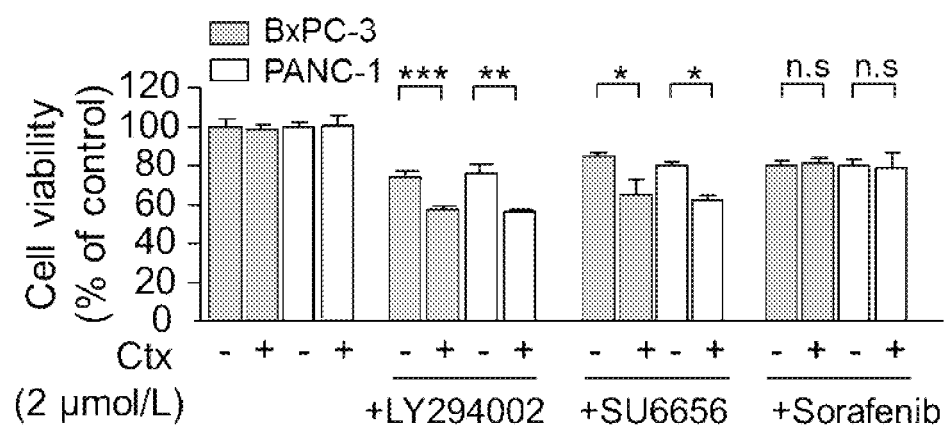

[Figure 3a]
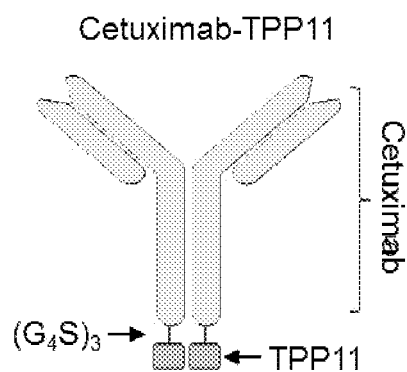
[Figure 3b]
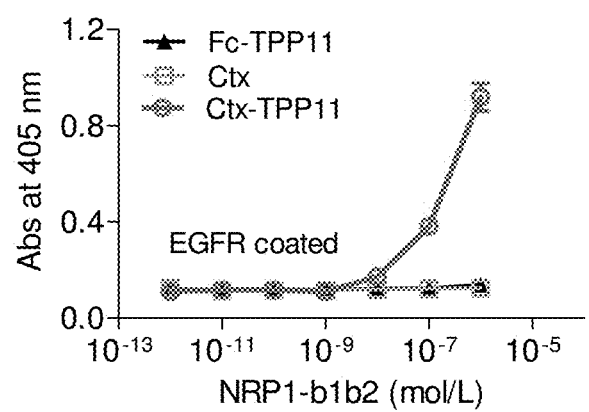

[Figure 4a]
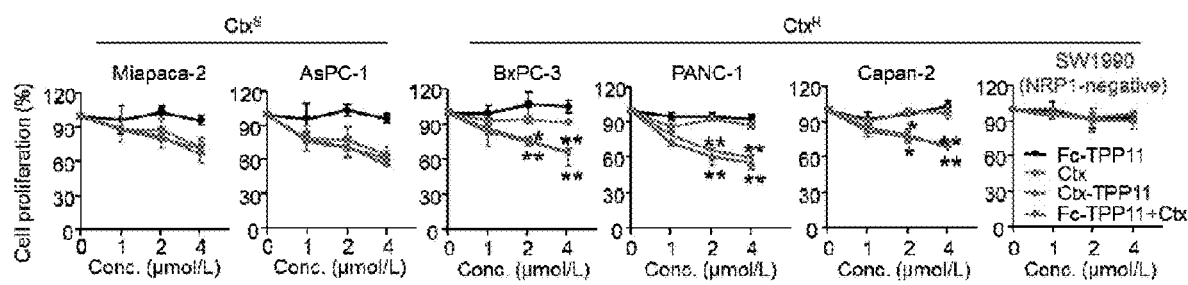
[Figure 4b]
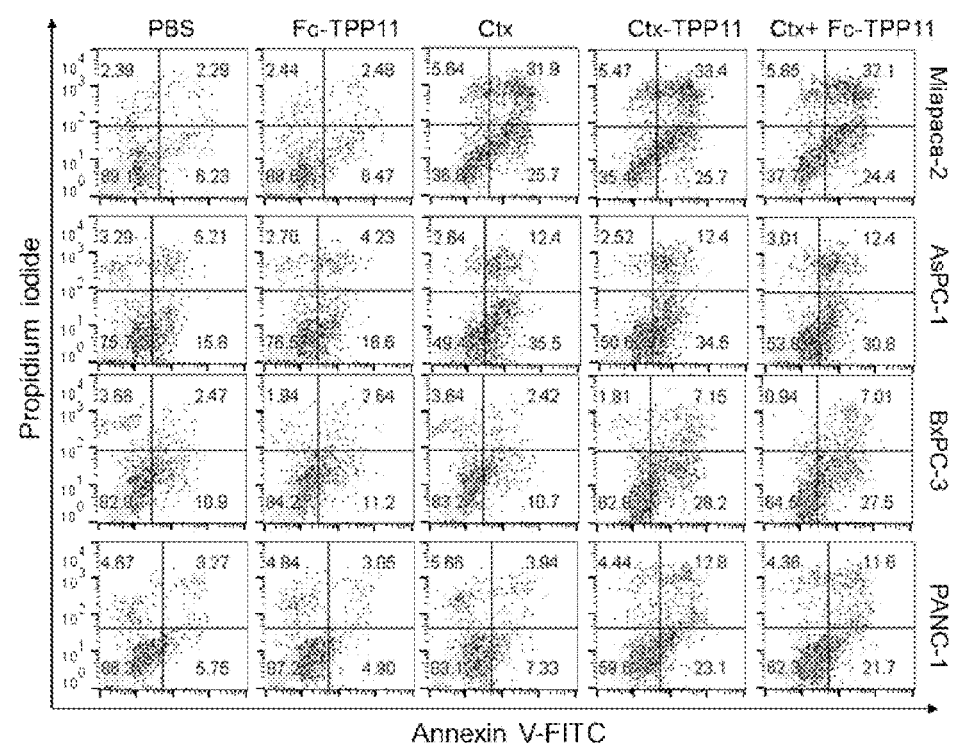

[Figure 4c]
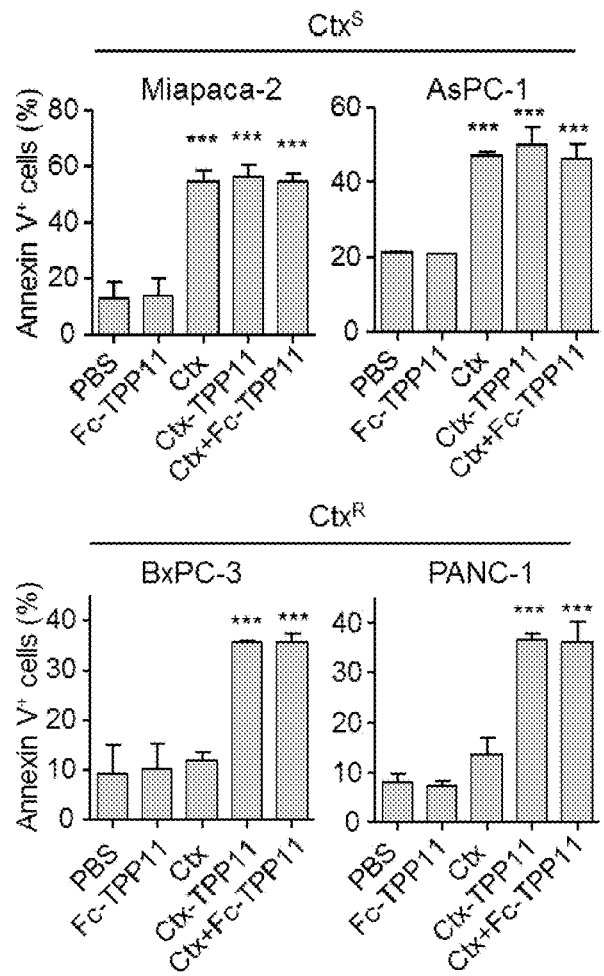
[Figure 4d]
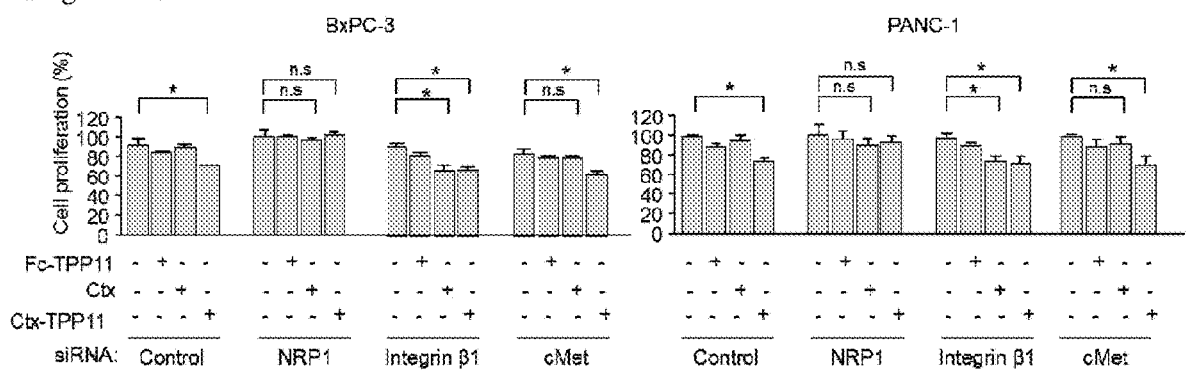

[Figure 4e]
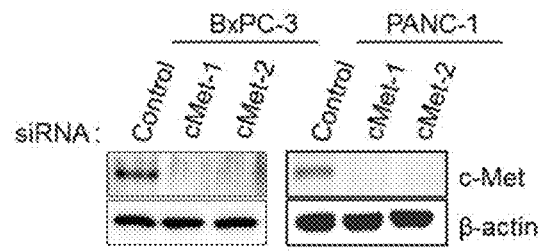
[Figure 4f]
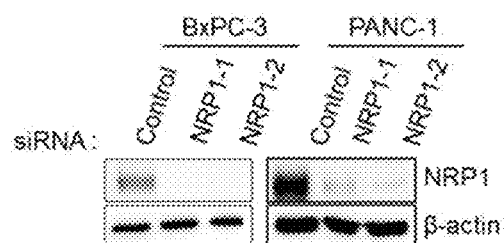
[Figure 5a]
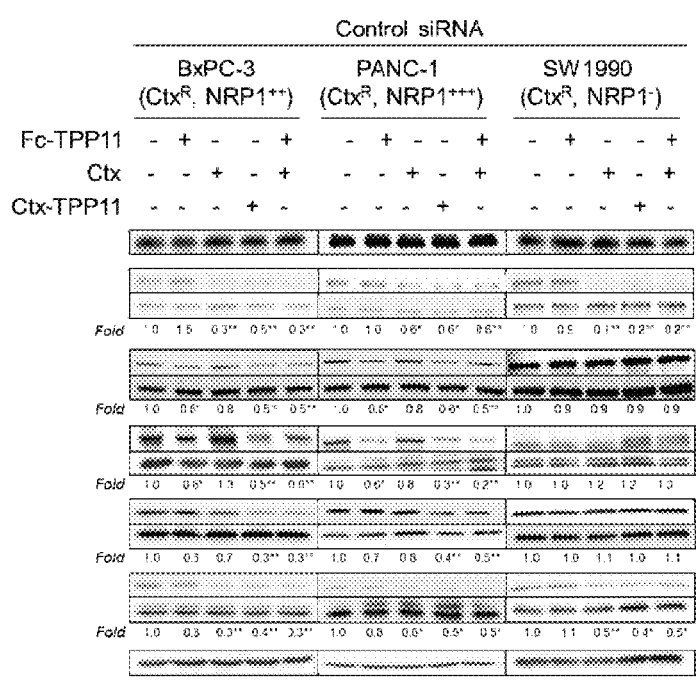

[Figure 5b]
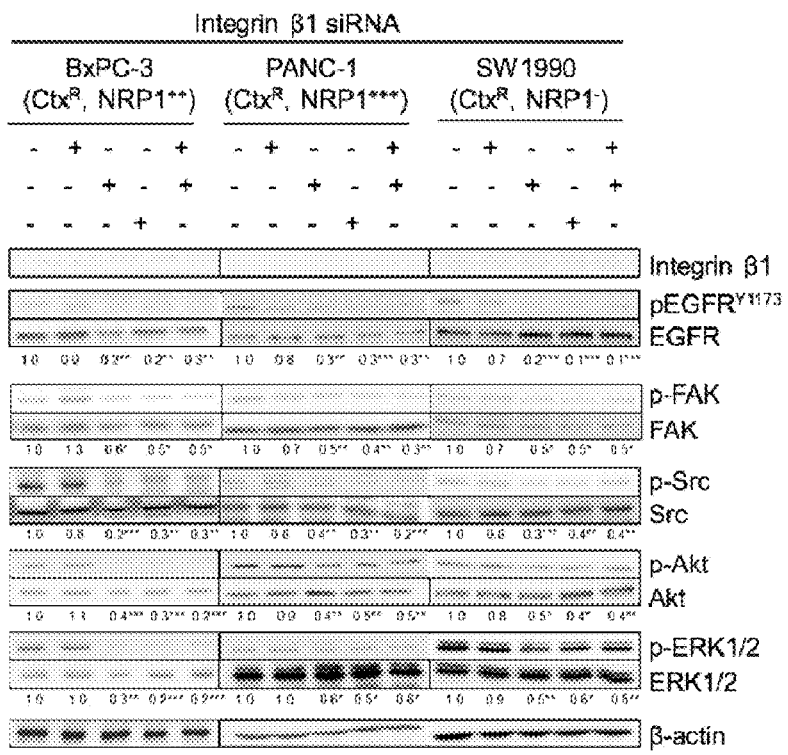
[Figure 6]
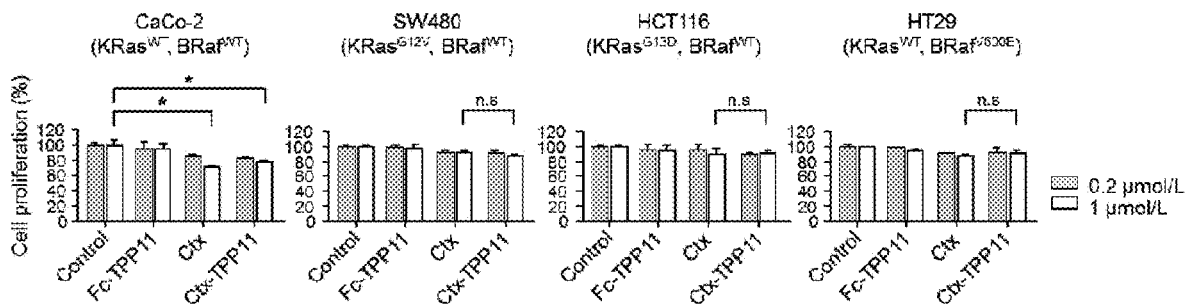

【Figure 7a】
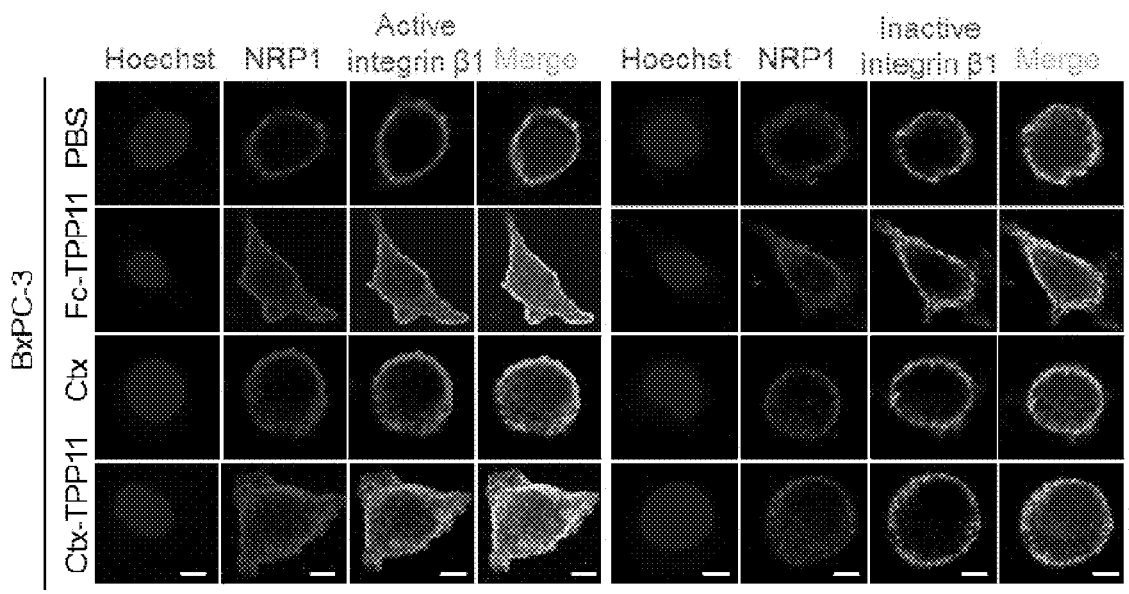
【Figure 7b】
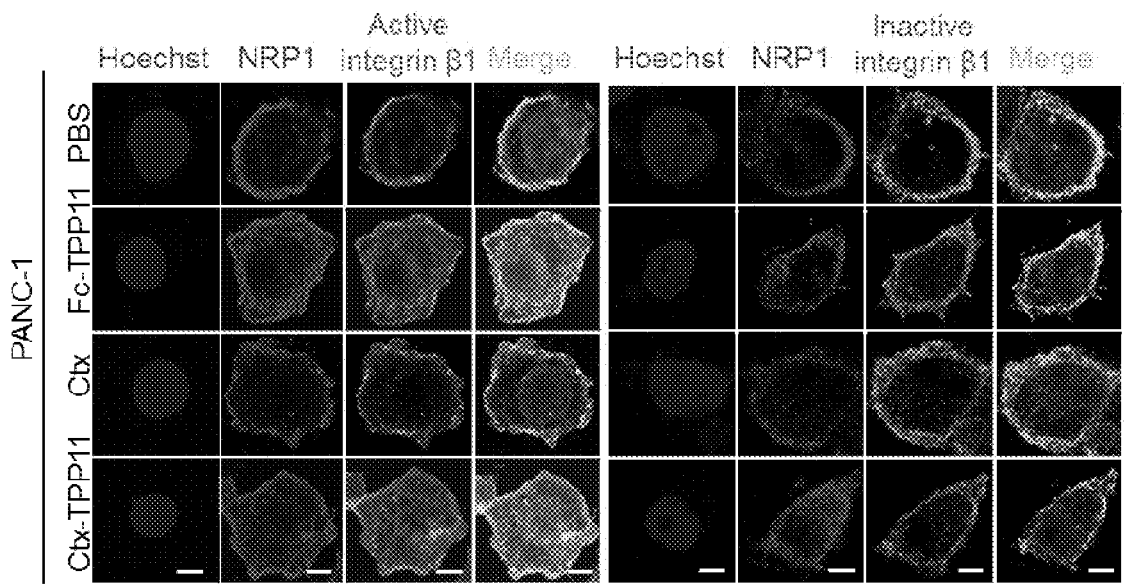

[Figure 8a]
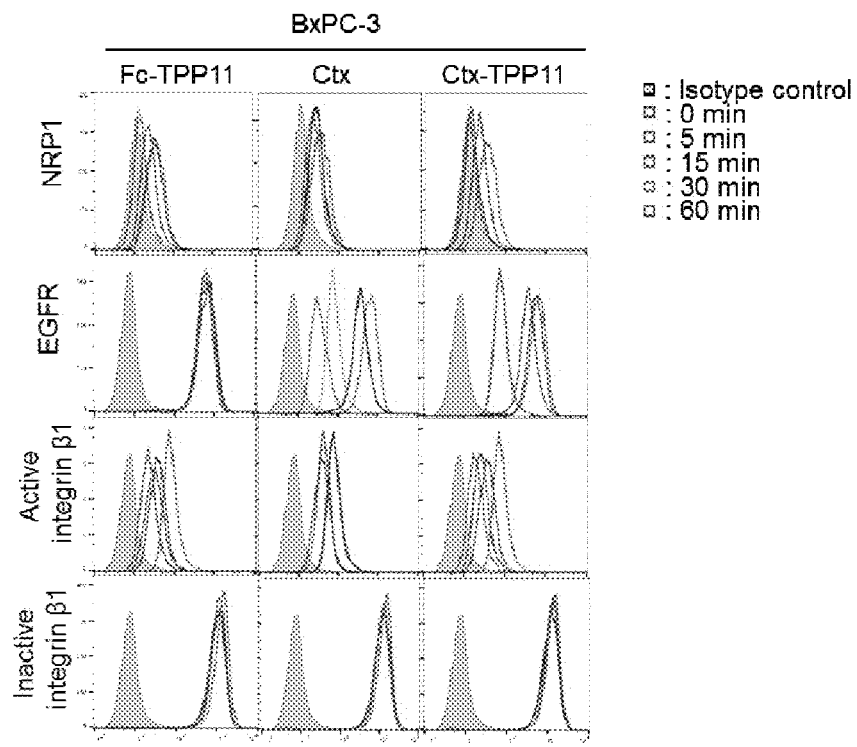
[Figure 8b]
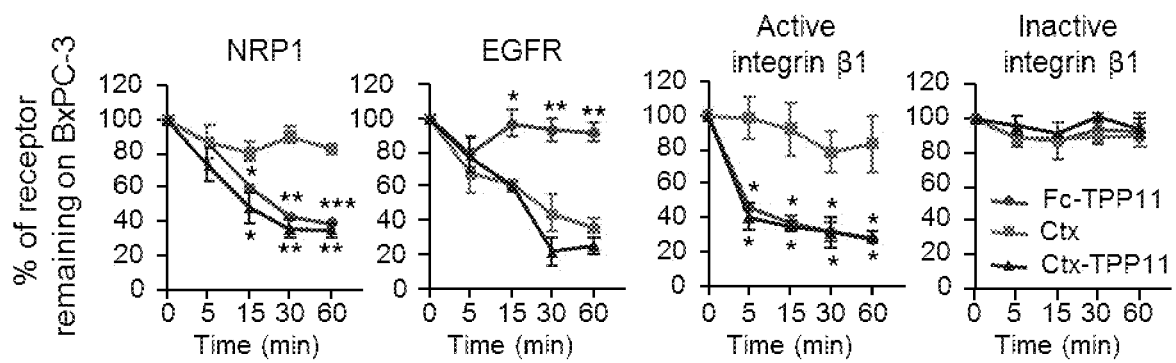

[Figure 9a]
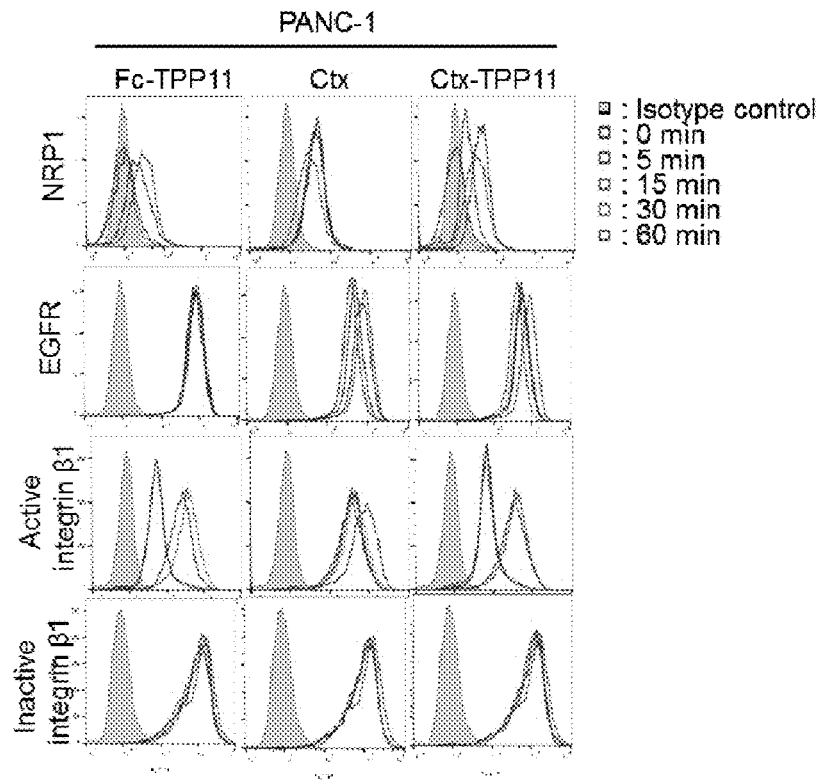
[Figure 9b]
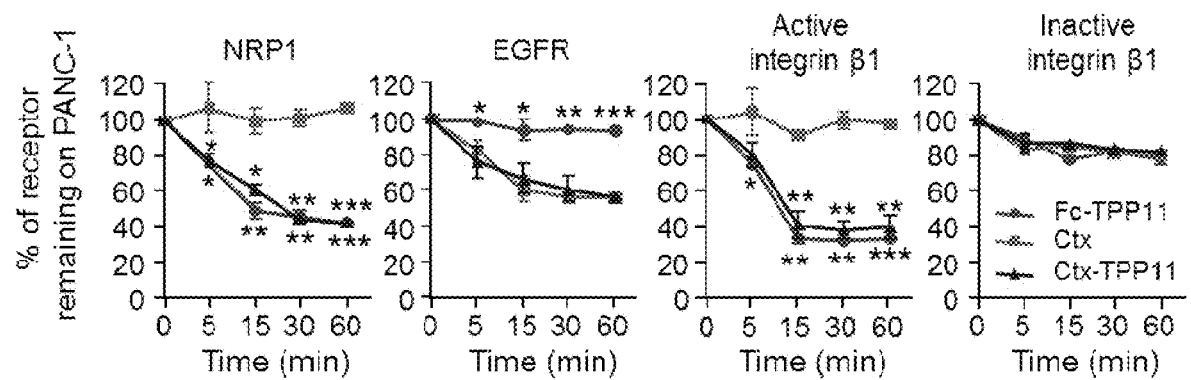

[Figure 10a]
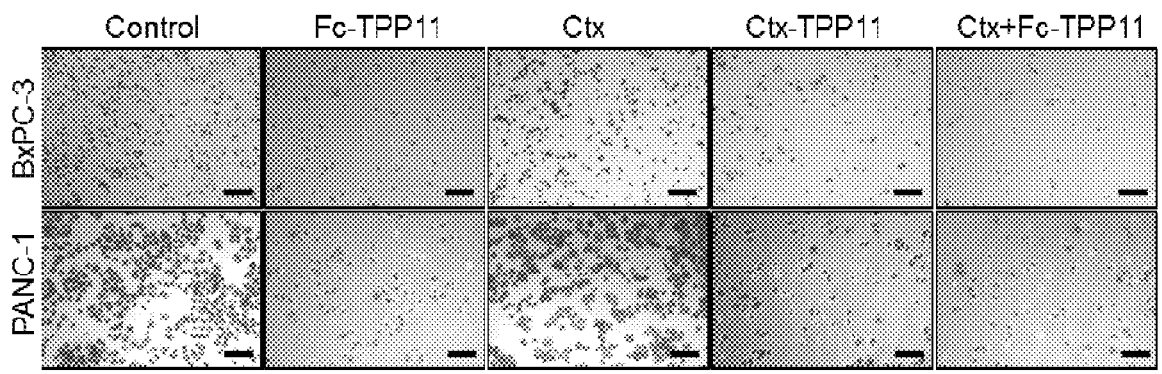
[Figure 10b]
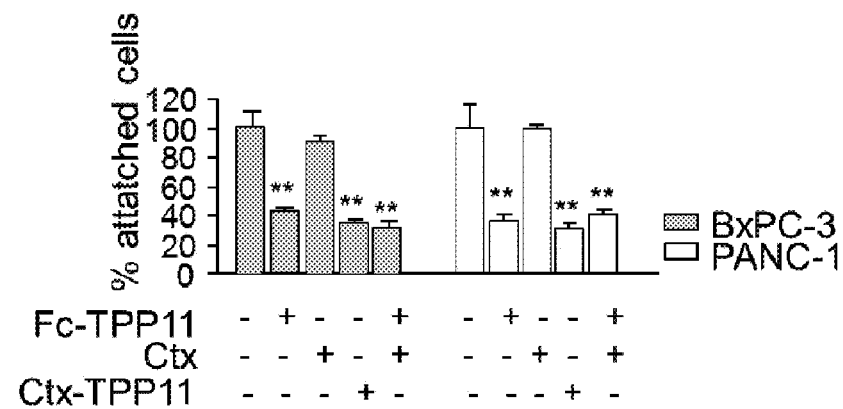

【Figure 11a】
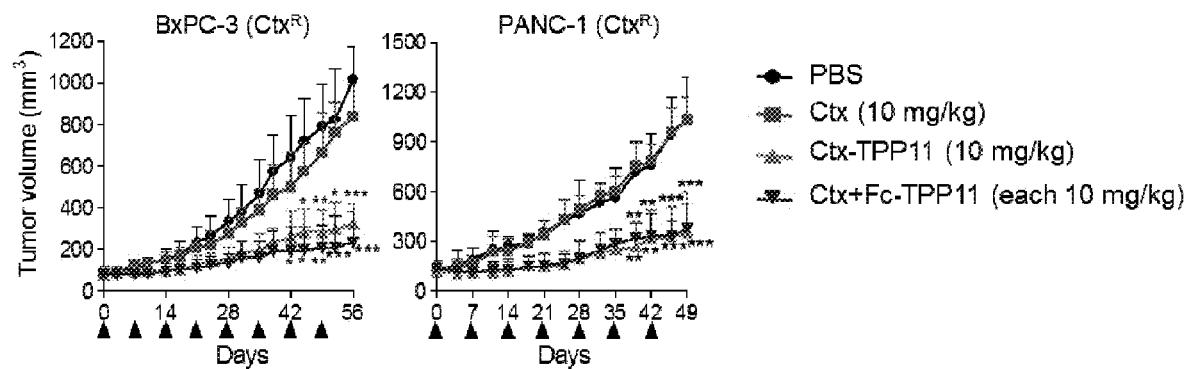
【Figure 11b】
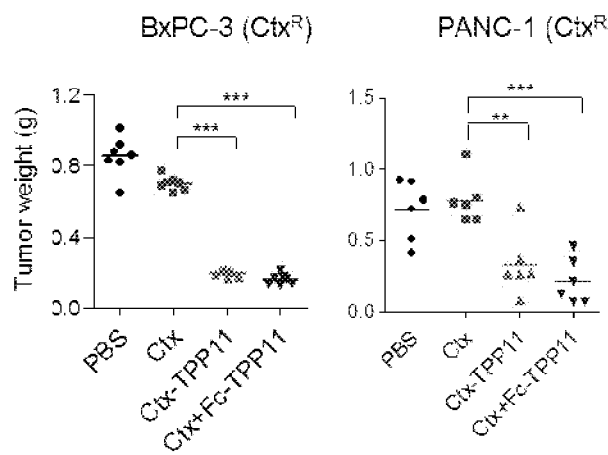
【Figure 11c】
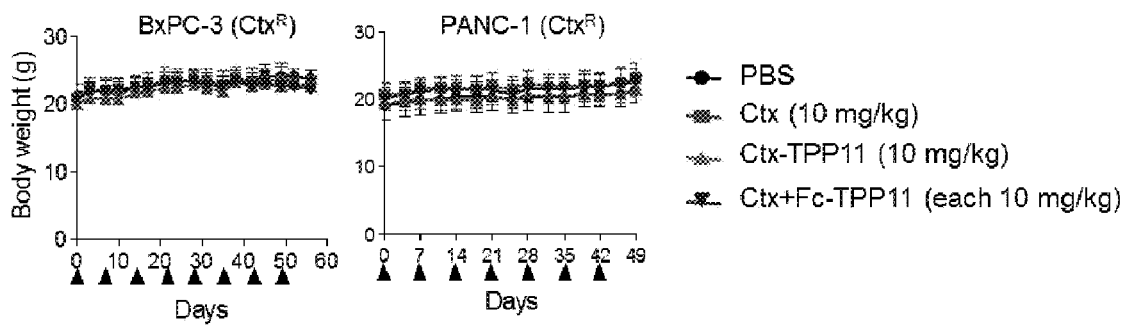

[Figure 12a]
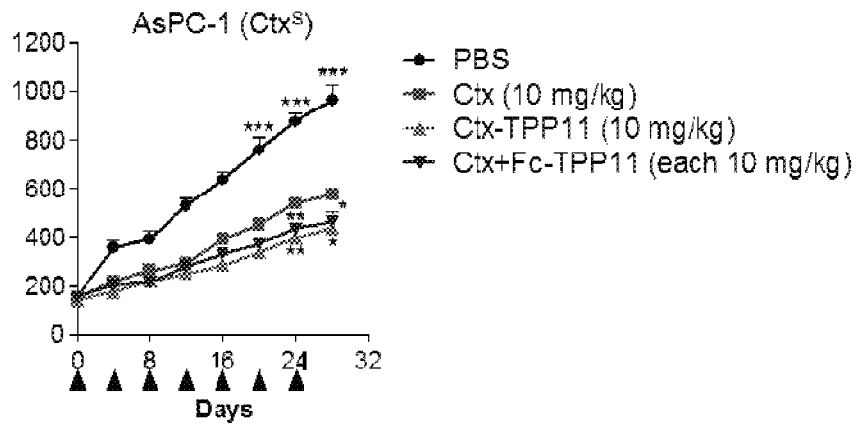
[Figure 12b]
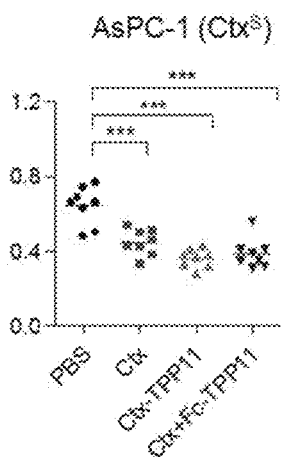
[Figure 12c]
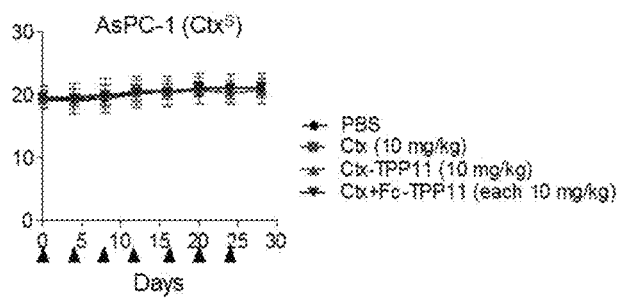

[Figure 13a]
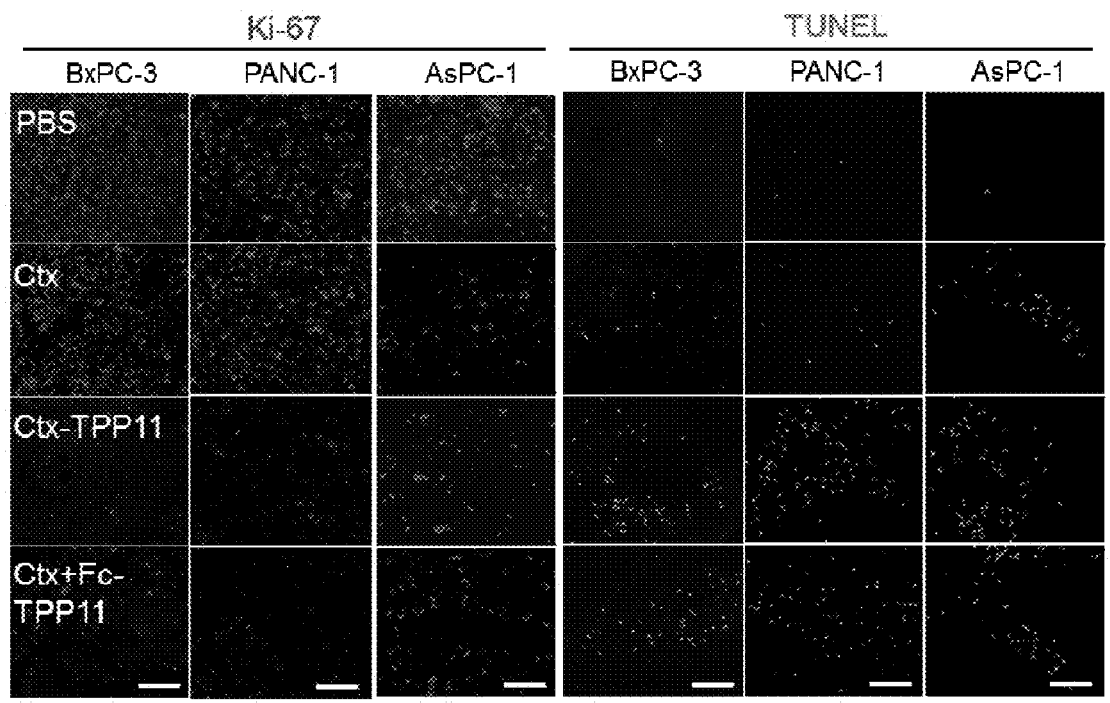
[Figure 13b]
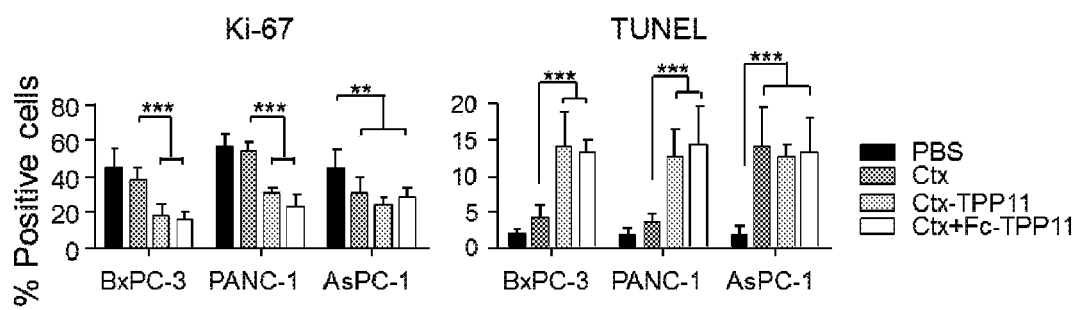

[Figure 14]
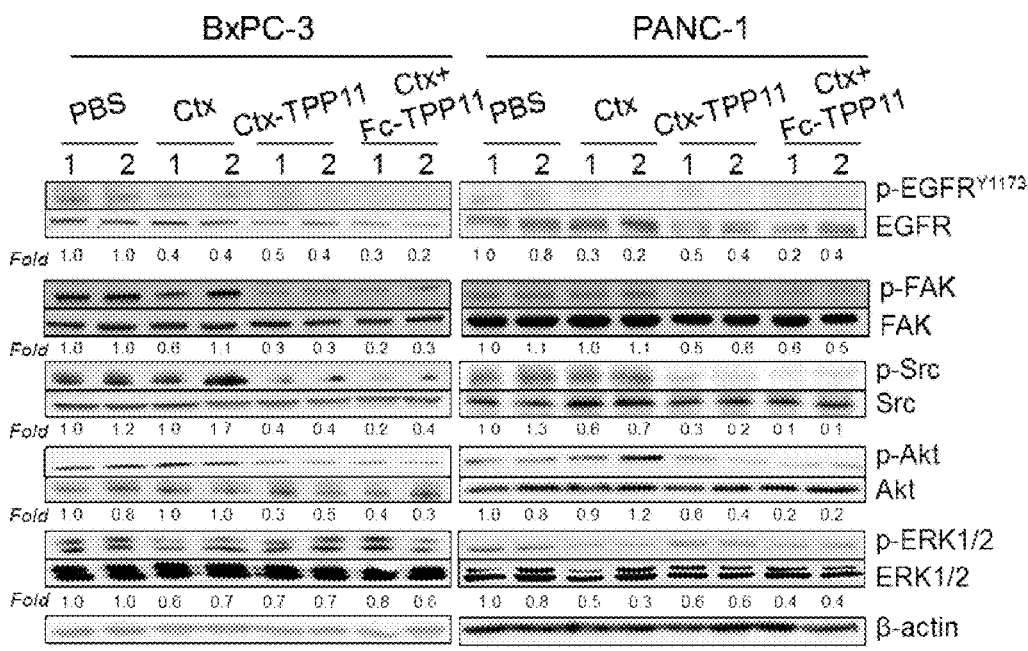
[Figure 15a]
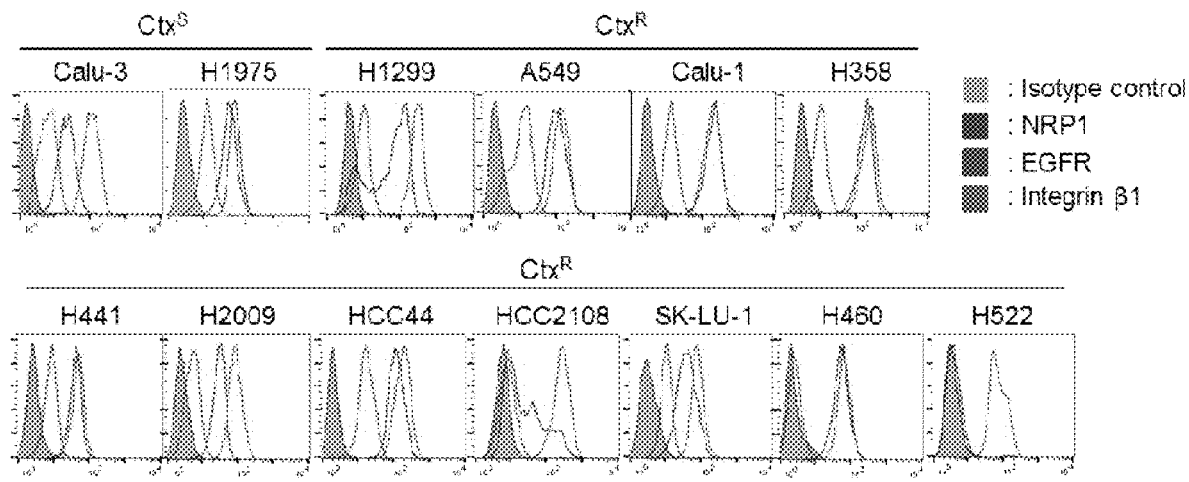

【Figure 15b】
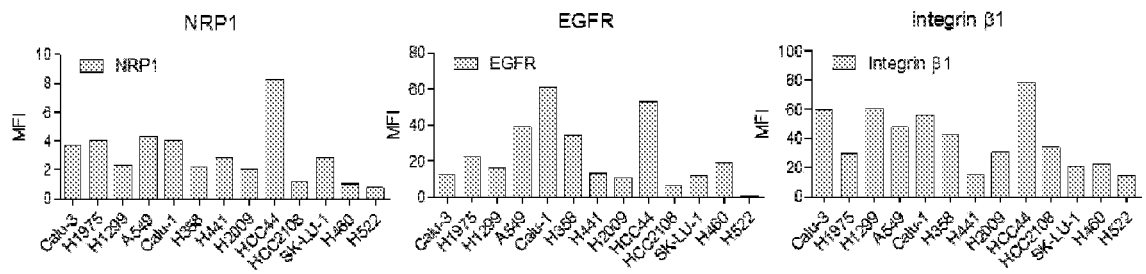
【Figure 16a】
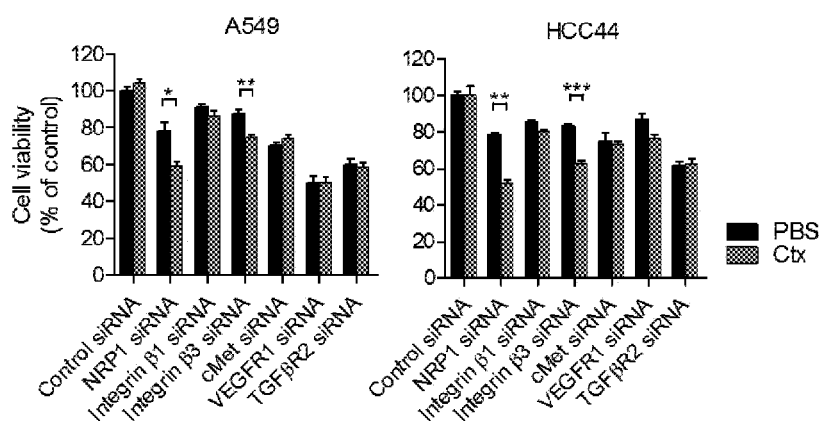
【Figure 16b】
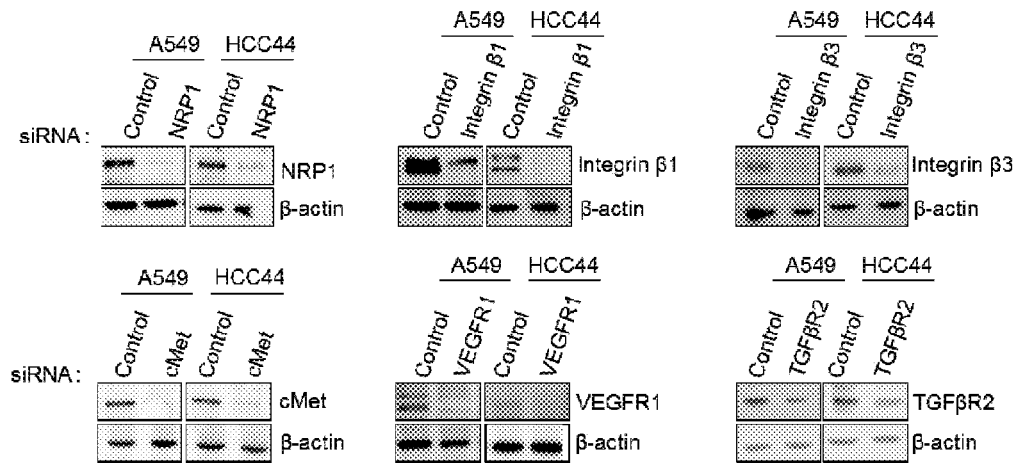

[Figure 17a]
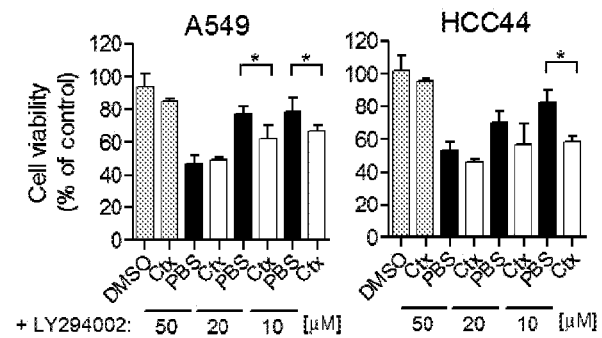
[Figure 17b]
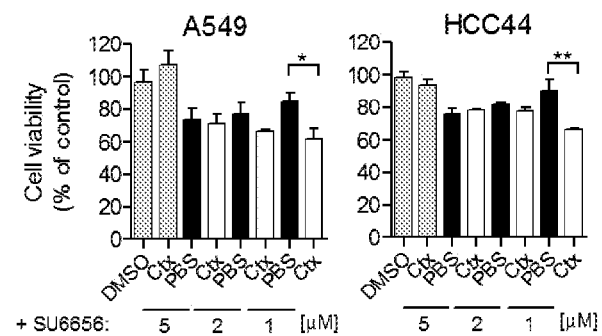
[Figure 17c]
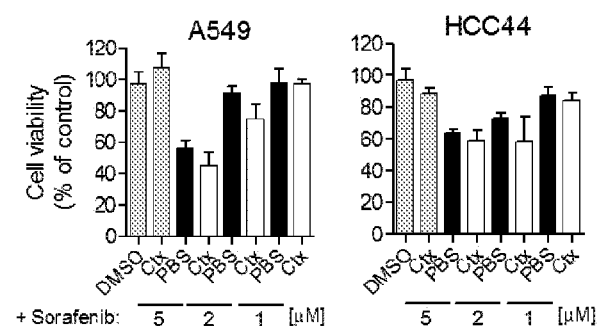

[Figure 18a]
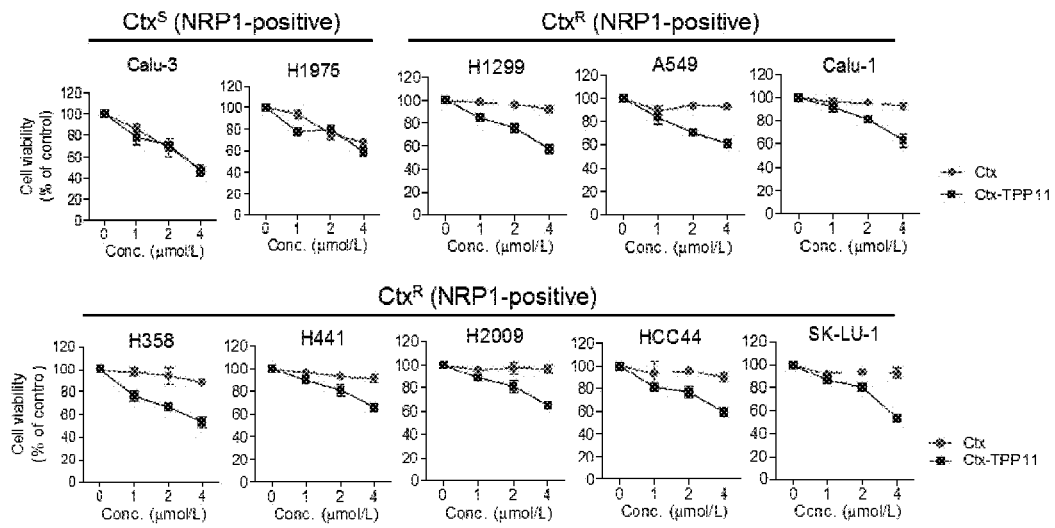
[Figure 18b]
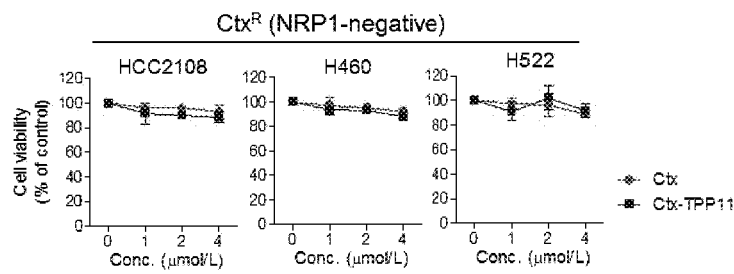
[Figure 18c]
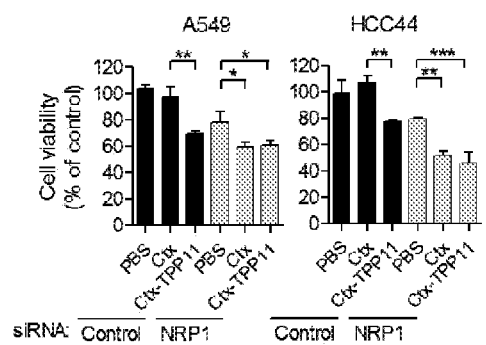

[Figure 19a]
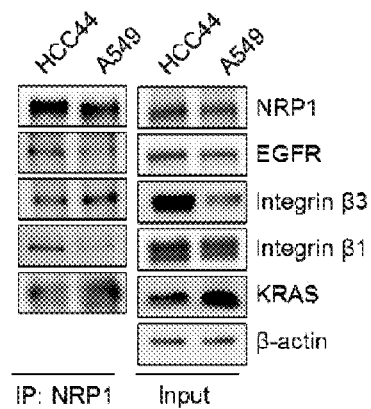
[Figure 19b]
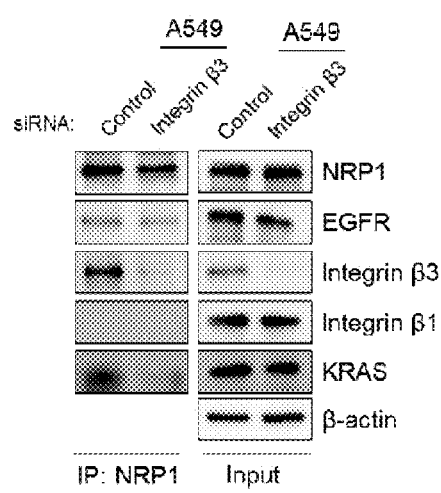

[Figure 20a]
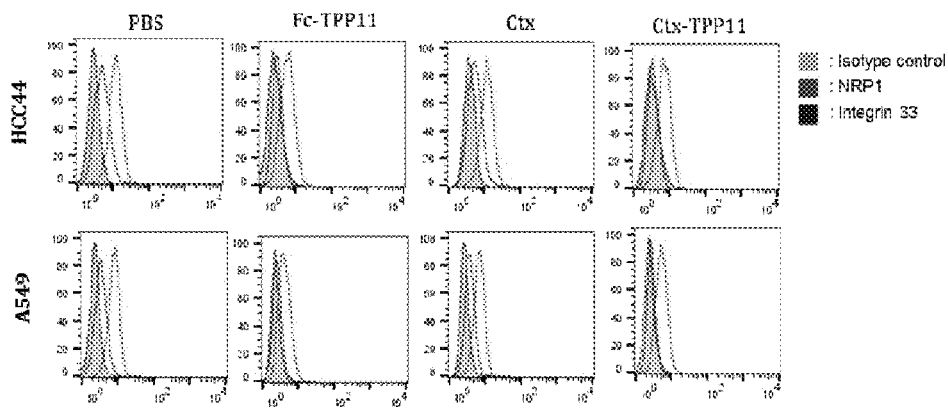
[Figure 20b]
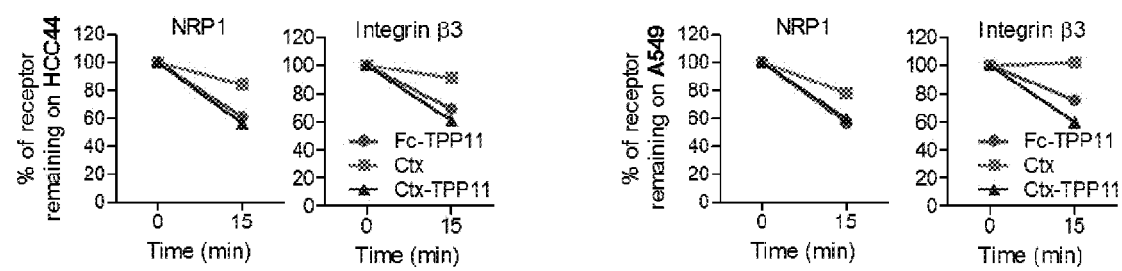
[Figure 21a]
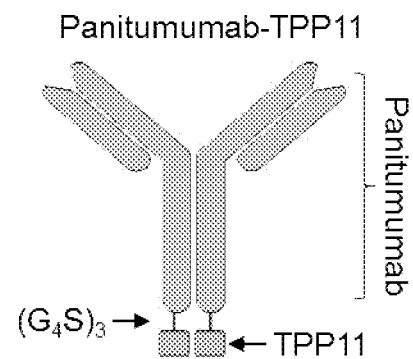

【Figure 21b】
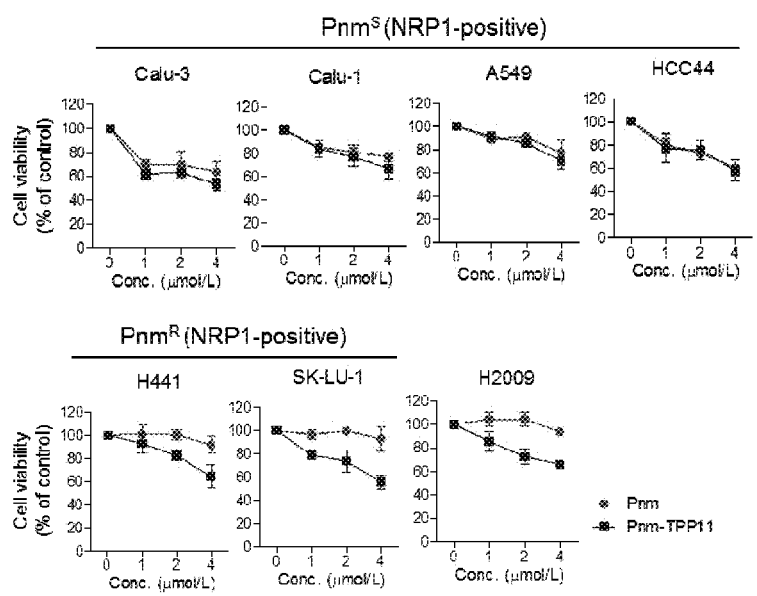
【Figure 21c】
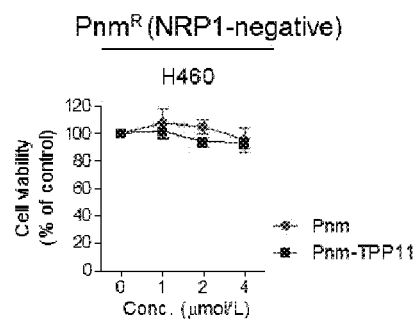

[Figure 22a]
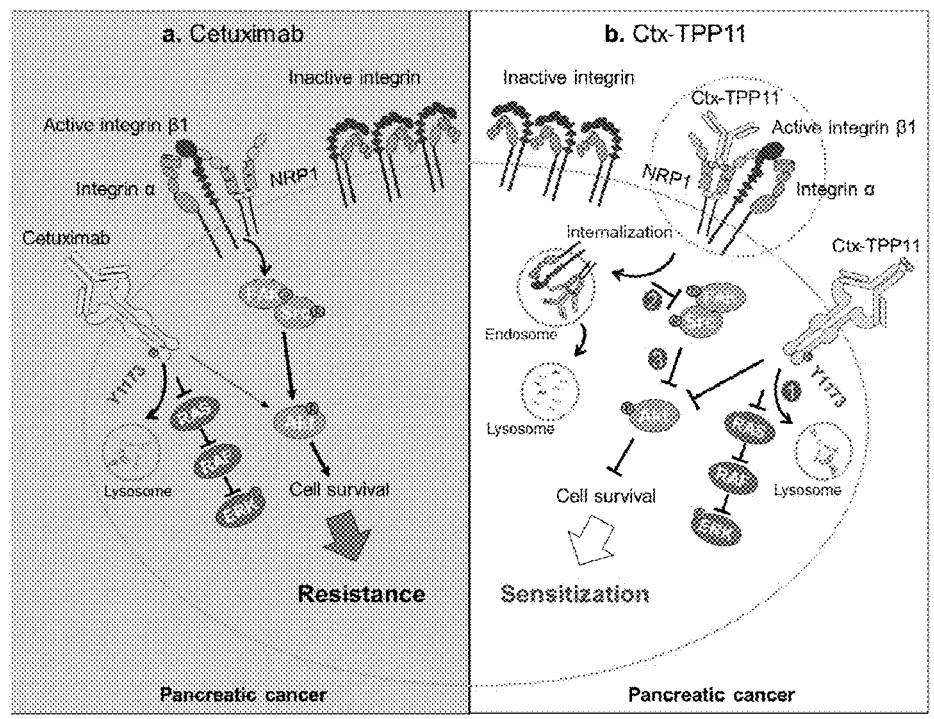
[Figure 22b]
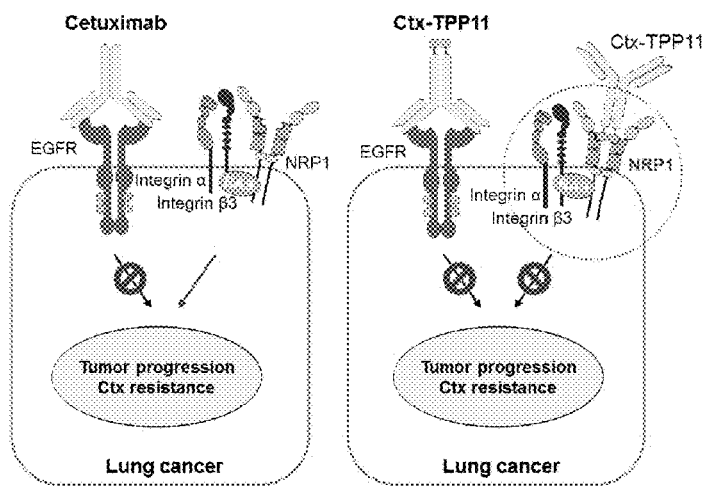

COMPOSITION FOR OVERCOMING RESISTANCE TO EGFR-TARGETING AGENT

CROSS REFERENCE TO RELATED APPLICATIONS

This application is a National Stage of International Application No. PCT/KR2017/003365 filed Mar. 28, 2017, claiming priority based on Korean Patent Application Nos. 10-2016-0037876 filed Mar. 29, 2016 and 10-2017-0037741 filed Mar. 24, 2017.

TECHNICAL FIELD

The present invention relates to a composition for overcoming resistance to an Epidermal Growth Factor Receptor (EGFR)-targeting antibody by fusion of neuropilin-1 (NRP1)-specific binding peptide to EGFR targeting antibody, and more particularly to a composition for treating cancers by overcoming resistance to an EGFR-targeting antibody alone, the composition comprising NRP1-binding peptide fused EGFR targeting antibody.

BACKGROUND ART

EGFR is a member of the cell receptor involved in cell function, such as cell growth, survival and metastasis, and overexpression or mutation of EGFR causes tumors. Accordingly, a number of antibodies and small-molecule tyrosine kinase inhibitors, which target EGFR, have been developed. For example, EGFR-targeting antibodies developed include cetuximab, panitumumab, zalutumumab, nimotuzumab, and matuzumab, and small-molecule tyrosine kinase inhibitors developed include gefitinib and erlotinib. These EGFR-targeting agents are used for the treatment of colorectal cancer, non-small cell lung cancer, and head and neck cancer. However, therapies employing these single drugs exhibit effects against specific types of tumor cells, and thus have limitations on their indications for use, or show resistance to various tumors or mutated tumors, and thus do not exhibit satisfactory therapeutic effects. For this reason, the development of multiple combination therapies that target two or more types of tumor cells is required for more effective cancer treatment.

Among various types of cancers, pancreatic cancer is a cancer with a very poor prognosis, and 60-80% of patients with pancreatic cancer show local severe diseases or metastatic diseases. For most pancreatic cancers, it is are known that EGFR and its ligands among a variety of receptor tyrosine kinases are overexpressed and play a major role in promoting the growth and survival of the cancers (Oliveira-Cunha et al., 2011; Wheeler et al., 2010). However, EGFR targeting agents developed to date are still not effective against pancreatic cancer. This is because many pancreatic cancers are resistant to the EGFR target agents. Accordingly, EGFR-targeting agents have been widely used for the treatment of pancreatic cancer in combination with the chemotherapeutic gene gemcitabine, but a problem arises in that they exhibit significant toxicity (Chong and Janne, 2013; Philip et al., 2010). Thus, there is a need to develop EGFR-targeting therapy effective against pancreatic cancer.

For lung cancer known as the main cause of cancer death worldwide, it is known that EGFR also plays a major role in the growth of the cancer (Sharma et al., 2007; Morgillo Floriana et al., 2016). Accordingly, various EGFR-targeting agents have been developed to treat lung cancer, and in particular, representative drugs include Gefitinib and Erlotinib, which are EGFR-targeting small-molecule tyrosine kinase inhibitors. However, although these targeting agents are highly effective drugs, only about 10% of lung cancer patients actually respond to these drugs (Socinski Mark A, 2007). Therefore, there is also an urgent need for a new alternative EGFR-targeting therapy against lung cancer.

Among EGFR-targeting agents, cetuximab (Ctx), an anti-EGFR antibody, inhibits the ligand (EGF, TGFα)-dependent activation of EGFR and prevents downstream signaling of EGFR. Ctx was FDA-approved for use in combination with chemotherapy for colorectal cancer and head and neck cancer, but was not approved for use for pancreatic and lung cancers that are resistant to EGFR-targeting agents. However, a clear mechanism of the resistance of pancreatic cancer and lung cancer cells to EGFR-targeting agents has not yet been found, and a method for improving this mechanism has not yet been developed.

The resistance mechanisms identified previously for colorectal cancer and head and neck cancer include: 1) high copy number of EGFR gene; 2) mutation of EGFR gene; 3) mutation of KRAS gene or BRAF gene, and the like (Oliveira-Cunha et al., 2011). To date, the mechanism of resistance against EGFR-targeting agents revealed in pancreatic cancer has been reported to be associated with the activation of the abnormal PI3K-Akt pathway by the EGFR family (EGFR, HER2, HER3), but this mechanism is also still unclear (Larbouret et al., 2012; Wong et al., 2014). For lung cancer, it has recently been reported that integrin $\beta 3$ binds to the KRAS gene and activates signaling from the KRAS-RalB-NFκB pathway, thereby inducing resistance to an EGFR-targeting agent (Laetitia Seguin, 2014). The absence of effective therapeutic drugs against pancreatic cancer and lung cancer is associated with a high mortality rate in patients, so it is necessary to accurately elucidate the mechanism of resistance to pancreatic cancer and lung cancer.

Neuropilin-1 (NRP1), a transmembrane glycoprotein, binds to VEGF-family ligands and class-3 semaphorin (Sema3A, Sema3B, Sema3C, Sema3D, Sema3E, Sema3F, Sema3G) ligands (Guo and Vander Kooi, 2015; Prud'homme and Glinka, 2012). NRP1 is very weakly expressed in normal cells, whereas it is overexpressed in most tumor vascular endothelial cells, solid tumor cells, and hematologic tumor cells, and plays an important role in tumor growth and metastasis. Some agents, small interfering RNAs, peptide inhibitors or NRP1-targeting antibodies have also been reported to reduce the growth, angiogenesis and metastasis of cancer cells by interfering with the function of NRP1 (Berge et al., 2010; Hong et al., 2007).

In addition, NRP1 is also overexpressed in pancreatic and lung cancer and plays a role in tumor growth. NRP1 acts as a co-receptor for various ligands. In particular, in pancreatic cancer, it binds to integrin $\beta 1$, thereby amplifying the signal of integrin $\beta 1$. It has been reported that integrin $\beta 1$ mainly activates the signal of the Src/Akt pathway and thus induces the resistance of lung cancer to erlotinib, an EGFR-targeting small-molecule tyrosine kinase inhibitor (Kanda et al., 2013). However, the relationship between the activation of NRP1/integrin $\beta 1$ in pancreatic cancer and the resistance of pancreatic cancer to EGFR-targeting agents has not been elucidated, and a new therapeutic agent for alleviating the resistance is also remarkably needed.

Under this technical background, the inventors of this application have identified a marker capable of predicting whether pancreatic cancer shows intrinsic resistance to an EGFR-targeting agent, and have used the marker to determine whether resistance to the EGFR-targeting agent appears, and particularly, have identified the possibility of regulating expression of the resistance-related marker by a peptide that binds specifically to neuropilin-1, as well as the mechanism of the regulation, and thus have found that resistance to the EGFR-targeting agent can be overcome. In addition, the present inventors have found that not only in pancreatic cancer but also on lung cancer resistant to EGFR-targeting agents, resistance to the EGFR-targeting agents can be overcome by a peptide that binds specifically to neuropilin-1, thereby completing the present invention.

The information disclosed in the Background Art section is only for the enhancement of understanding of the background of the present invention, and therefore may not contain information that forms a prior art that would already be known to a person of ordinary skill in the art.

DISCLOSURE OF INVENTION

Technical Problem

It is an object of the present invention to provide a composition capable of treating cancers by overcoming resistance to an EGFR-targeting antibody alone.

Another object of the present invention is to provide an anticancer drug or an anticancer adjuvant comprising the composition capable of treating cancer by overcoming resistance to an EGFR-targeting antibody alone.

Still another object of the present invention is to provide a composition for co-administration, which can treat cancer by overcoming resistance to an EGFR-targeting antibody in combination with the EGFR-targeting antibody.

Technical Solution

To achieve the above object, the present invention provides a composition for treating cancer, which comprises a NRP1-specific binding peptide-fused EGFR-targeting antibody, which can overcome the resistance to an EGFR-targeting antibody alone.

The present invention also provides an anticancer drug comprising the above-described composition.

The present invention also provides an anticancer adjuvant comprising the above-described composition.

The present invention also provides a composition for co-administration for cancer treatment, which comprises: a NRP1-binding peptide-fused Fc and an EGFR-targeting antibody, the combination of which can overcome the resistance to the EGFR-targeting antibody alone.

BRIEF DESCRIPTION OF THE DRAWINGS

FIG. 1 shows the characteristics of pancreatic cancer cell lines having or not having intrinsic resistance to Ctx.

FIG. 1a shows the results of flow cytometry (FACS) analysis performed to analyze the cell surface expression levels of EGFR, NRP1 and integrin-β1 in pancreatic cancer cell lines (BxPC-3, PANC-1, Capan-2, and SW1990) having intrinsic resistance to Ctx (cetuximab-resistant, $Ctx^R$) and in pancreatic cancer cell lines (Miapaca-2, and AsPC-1) not resistant to Ctx (cetuximab-sensitive, $Ctx^S$).

FIG. 1b shows the results of Western blot analysis performed to analyze the whole expression levels (cell surface and interior) of EGFR, NRP1 and integrin-β1 in the above-described pancreatic cancer cell lines.

FIG. 1c compares molecular characteristics in $Ctx^S$ and $Ctx^R$ pancreatic cancer cell lines. It shows the results of Western blot analysis of the whole expression levels and phosphorylation levels of EGFR, Akt, Src and ERK in non-Ctx-treated group and Ctx-treated group.

FIG. 2 shows the results of an MTT assay performed to evaluate the effects of each siRNA (short interfering RNA) and inhibitor in order to examine whether the resistance of $Ctx^R$ pancreatic cancer cell lines to Ctx is associated with overexpressed integrin-β1, Src and Akt.

FIG. 2a is a graph showing cell viability after Ctx treatment of $Ctx^R$ cell lines (BxPC-3, PANC-1 and SW1990) treated with each of control siRNA and integrin-β1 siRNA.

FIG. 2b shows the results of Western blot analysis performed to confirm whether integrin-β1 siRNA used in FIG. 2a inhibits expression of integrin-β1.

FIG. 2c is a graph showing the results of analyzing the cell viability of $Ctx^R$ cell lines after treatment with Ctx in combination with each of a PI3K-Akt inhibitor (LY294002), an Src inhibitor (SU6656) and an Raf inhibitor (Sorafenib).

FIG. 3 shows a schematic view of constructed Ctx-TPP11 and the results of examining the ability bind to both NRP1 and EGFR.

FIG. 3a is a schematic view of Ctx-TPP11 in which a NRP1-binding TPP11 peptide is fused to the C-terminus of the heavy chain of Ctx by a $(G_4S)_3$ linker consisting of 15 residues.

FIG. 3b shows the results of a sandwich ELISA (enzyme linked immunosorbent assay) to examine whether the constructed Ctx-TPP11 shows a binding affinity for both EGFR and NRP1-b1b2 in comparison with Fc-TPP11 and Ctx.

FIG. 4 shows results indicating that Ctx-TPP11 can inhibit the proliferation of NRP1-expressing $Ctx^R$ pancreatic cancer cells and promote apoptosis of the cells.

FIG. 4a shows the results of an MTT assay performed to measure the proliferation of $Ctx^S$ and $Ctx^R$ pancreatic cancer cell lines after treatment with various concentrations of Fc-TPP11, Ctx and Ctx-TPP11.

FIG. 4b shows the results of FACS analysis performed using an Annexin V-FITC apoptosis detection kit in order to analyze the apoptosis of $Ctx^S$ and $Ctx^R$ pancreatic cancer cell lines after treatment with Fc-TPP11, Ctx and Ctx-TPP11.

FIG. 4c is a graph showing the results of quantifying the apoptosis of annexin V-FITC-stained cells in the dot plot shown in FIG. 4b.

FIG. 4d shows the effects of evaluating the effects of NRP1, integrin-β1 and cMet siRNA on the inhibition of cell proliferation of $Ctx^R$ pancreatic cancer cell lines.

FIGS. 4e and 4f shows the results of Western blot analysis performed to confirm whether the NRP1 and cMet siRNA used in FIG. 4d inhibit the expression of NRP1 and cMet.

FIG. 5 shows the results of Western blot analysis performed to examine inhibitory signals of Fc-TPP11, Ctx and Ctx-TPP11 against the phosphorylation of EGFR, Src, Akt and ERK1/2 after treatment with siRNA and integrin-β1 siRNA.

FIG. 5a shows the results of examining the signal inhibitory effects of Fc-TPP11, Ctx and Ctx-TPP11 in three $Ctx^R$ pancreatic cancer cell lines (BxPC-3, PANC-1, and SW1990) after treatment with control siRNA.

FIG. 5b shows the results of examining the signal inhibitory effects of Fc-TPP11, Ctx and Ctx-TPP11 in three $Ctx^R$ pancreatic cancer cell lines (BxPC-3, PANC-1, and SW1990) after treatment with integrin-β1 siRNA.

FIG. 6 shows the results of an MTT assay performed to examine the cell proliferation inhibitory abilities of Fc-TPP11, Ctx and Ctx-TPP11 in KRas wild-type and BRaf wild-type $Ctx^S$ colorectal cancer cell lines and colorectal cancer lines having resistance to Ctx due to KRas and BRaf mutations, unlike pancreatic cancer.

FIG. 7 shows the results of confocal microscopic observation performed to examine the endocytosis of NRP1, active integrin β1 and inactive integrin β1 in $Ctx^R$ BxPC-3 and PANC-1 after treatment with Fc-TPP11, Ctx and Ctx-TPP11.

FIG. 7a shows the results of observation in $Ctx^R$ BxPC-3.

FIG. 7b shows the results of observation in $Ctx^R$ PANC-1.

FIG. 8 shows the results of FACS analysis performed to analyze the endocytosis of NRP1, EGFR, active integrin β1 and inactive integrin β1 in $Ctx^R$ BxPC-3 after treatment with Fc-TPP11, Ctx and Ctx-TPP11.

FIG. 8a is a histogram graph showing the cell surface expression levels of NRP1, EGFR, active integrin β1 and inactive integrin β1 after treatment with Fc-TPP11, Ctx and Ctx-TPP11.

FIG. 8b is a graph showing the mean fluorescence intensity (MFI) of the histogram shown in FIG. 8a.

FIG. 9 shows the results of FACS analysis performed to analyze the endocytosis of NRP1, EGFR, active integrin β1 and inactive integrin β1 in $Ctx^R$ PANC-1 after treatment with Fc-TPP11, Ctx and Ctx-TPP11.

FIG. 9a is a FACS histogram graph showing the cell surface expression levels of NRP1, EGFR, active integrin β1 and inactive integrin β1 after treatment with Fc-TPP11, Ctx and Ctx-TPP11.

FIG. 9b is a graph showing the mean fluorescence intensity of the histogram shown in FIG. 9a.

FIG. 10 shows the results of a cell adhesion assay performed to examine the cell adhesion ability of fibronectin (FN) in $Ctx^R$ BxPC-3 and PANC-1 after treatment with Fc-TPP11, Ctx and Ctx-TPP11.

FIG. 10a shows the results of optical microscopic observation of cell adhesion.

FIG. 10b is a graph comparatively comparing the number of cells attached to FN after the cell adhesion assay.

FIG. 11 shows the results of measuring the in vivo $Ctx^R$ pancreatic tumor growth inhibitory activity of Ctx-TPP11 in mice.

FIGS. 11a and 11b are graphs showing the change in tumor volume in $Ctx^R$ BxPC-3 and PANC-1 xenograft nude mice by administration of Ctx, Ctx-TPP11 or a combination of Ctx and Fc-TPP11 (a), and the weight of dissected tumors at the end of administration (b).

FIG. 11c shows change in the mouse weight measured at varying time points during the experiment associated with FIG. 11a.

FIG. 12 shows the results of measuring the in vivo $Ctx^S$ pancreatic tumor growth inhibitory activity of Ctx-TPP11 in mice.

FIGS. 12a and 12b show the change in tumor volume in $Ctx^S$ AsPC-1 xenograft nude mice by administration of Ctx, Ctx-TPP11 or a combination of Ctx and Fc-TPP11 (a), and the weight of dissected tumors at the end of administration (b).

FIG. 12c shows change in the mouse weight measured at varying time points during the experiment associated with FIG. 12a.

FIG. 13 shows the results of immunohistochemistry (IHC) that compare the levels of growth markers and apoptotic markers in the tumor tissues against which tumor inhibitory activity was confirmed in FIGS. 11 and 12.

FIG. 13a shows the results of confocal microscopic observation of the growth marker Ki-67 and the apoptotic marker TUNEL in the tumors dissected in the experiments of FIGS. 11 and 12.

FIG. 13b is a graph quantitatively comparing Ki-67 and TUNEL of FIG. 13a.

FIG. 14 shows the results of Western blot analysis on dissected tumor tissues against which tumor inhibitory activity was confirmed in FIG. 11.

FIG. 15 shows the results of comparing the cell surface expression levels of EGFR, NRP1 and integrin β1 in $Ctx^S$ and $Ctx^R$ lung cancer cell lines.

FIG. 15a is a histogram showing the results of FACS analysis performed to analyze the cell surface expression levels of EGFR, NRP1 and integrin β1 in two $Ctx^S$ lung cancer cell lines (Calu-3, and H1975) and 11 $Ctx^R$ lung cancer cell lines (H1299, A549, Calu-1, H358, H441, H2009, HCC44, HCC2108, SK-LU-1, H460, and H522).

FIG. 15b is a graph showing the mean fluorescence intensity of the histogram shown in FIG. 15a.

FIG. 16 shows the results of a WST-1 assay performed to examine the effects of siRNA against receptors (with which NRP1 acts as co-receptor) among various cell surface receptors in order to examine which cell surface receptors are involved in the resistance of $Ctx^R$ long cancer cell lines to Ctx.

FIG. 16a is a graph showing the results of analyzing cell viability after Ctx treatment in two $Ctx^R$ lung cancer cell lines (A549 and HCC44) treated with each of control siRNA, NRP1 siRNA, integrin β1 siRNA, integrin β3 siRNA, cMet siRNA, VEGFR1 siRNA, and TGFβ2 siRNA.

FIG. 16b shows the results of Western blot analysis performed to confirm that the siRNAs used in FIG. 16a specifically inhibit expression of their target proteins.

FIG. 17 is a graph showing the cell viability of $Ctx^R$ cell lines by treatment with Ctx in combination with a PI3K-Akt inhibitor (LY294002), an Src inhibitor (SU6656) and an Raf inhibitor (Sorafenib).

FIG. 18 shows results indicating that Ctx-TPP11 can inhibit the proliferation of $Ctx^R$ lung cancer cells.

FIG. 18a shows the results of a WST-1 assay performed to measure cell viability in two NRP1-expressing $Ctx^S$ lung cancer cell lines (Calu-3 and H1975) and eight $Ctx^R$ lung cancer cell lines (H1299, A549, Calu-1, H358, H441, H2009, HCC44, and SK-LU-1) after treatment with various concentrations of Ctx and Ctx-TPP11.

FIG. 18b shows the results of a WST-1 assay performed to measure cell viability in three non-NRP1-expressing $Ctx^R$ lung cell lines (HCC2108, H460 and H522) after treatment with various concentrations of Ctx and Ctx-TPP11.

FIG. 18c shows results indicating that the effect of NRP1 siRNA on the cell proliferation inhibitory ability of Ctx-TPP11 in $Ctx^R$ lung cancer cell lines.

FIG. 19 shows the results of an immunoprecipitation assay performed to examine the correlation between NRP1, integrin β3 and KRAS in $Ctx^R$ lung cancer cell lines.

FIG. 19a shows the results of an immunoprecipitation assay performed using NRP1 antibody in $Ctx^R$ lung cancer cell lines (HCC44 and A549).

FIG. 19b shows the results of an immunoprecipitation assay performed using NRP1 antibody in A549 treated with control siRNA and in A549 treated with integrin β3 siRNA.

FIG. 20 shows the results of FACS analysis performed to analyze the endocytosis of NRP1 and integrin β3 in $Ctx^R$ HCC44 and A549 after treatment with Fc-TPP11, Ctx and Ctx-TPP11.

FIG. 20a is a histogram graph showing the cell surface expression levels of NRP1 and integrin β3 after treatment with Fc-TPP11, Ctx and Ctx-TPP11.

FIG. 20b is a graph showing the mean fluorescence intensity (MFI) of the histogram shown in FIG. 20a.

FIG. 21 shows results indicating that Panitumumab-TPP11 (Pnm-TPP11), obtained by fusing TPP11 to Panitumumab (Pnm) among EGFR-targeting antibodies, in addition to Ctx, can inhibit the proliferation of Pnm$^R$ lung cancer cells.

FIG. 21a is a schematic view of Pnm-TPP11 in which a TPP11 peptide is fused to the C-terminus of the heavy chain of Pnm by a (G$_4$S)$_3$ linker consisting of 15 residues.

FIG. 21b shows the results of a WST-1 assay performed to measure cell viability in NRP1-expressing Pnm$^S$ and Pnm$^R$ lung cancer cell lines after treatment with various concentrations of Pnm and Pnm-TPP11.

FIG. 21c shows the results of a WST-1 assay performed to measure cell viability in a non-NRP1-expressing Pnm$^R$ lung cancer cell line after treatment with various concentrations of Pnm and Pnm-TPP11.

FIG. 22 is an overall schematic view showing the mechanisms of resistance of Ctx$^R$ pancreatic cancer and lung cancer and the mechanism of overcoming Ctx$^R$ by Ctx-TPP11.

FIG. 22a is an overall schematic view showing the mechanisms of resistance of Ctx$^R$ pancreatic cancer and the mechanism of overcoming Ctx$^R$ by Ctx-TPP11.

FIG. 22b is an overall schematic view showing the mechanisms of resistance of Ctx$^R$ lung cancer and the mechanism of overcoming Ctx$^R$ by Ctx-TPP11.

BEST MODE FOR CARRYING OUT THE INVENTION

Unless defined otherwise, all the technical and scientific terms used herein have the same meaning as those generally understood by one of ordinary skill in the art to which the invention pertains. Generally, the nomenclature used herein and the experiment methods, which will be described below, are those well known and commonly employed in the art.

In one aspect, the present invention is directed to a composition for treating cancer, which comprises a neuropilin-1 (NRP1)-specific binding peptide-fused EGFR targeting antibody that overcomes the resistance to an EGFR-targeting antibody alone.

The present invention is also directed to a method for treating cancer, which comprises administering to a patient with a NRP1-binding peptide fused EGFR-targeting antibody that overcomes the resistance an EGFR-targeting antibody, particularly to a method for treating cancer exhibiting resistance to an EGFR-targeting antibody alone.

The peptide may comprise one or more sequences that bind specifically to neuropilin-1, and for example, are selected from the group consisting of the following SEQ ID NOS: 1 to 3:

HTPGNSKPTRTPRR, (TPP11, SEQ ID NO: 1)

HTPGNSNQFVLTSTRPPR, (TPP1, SEQ ID NO: 2)
and

HTPGIATRTPR. (TPP8, SEQ ID NO: 3)

The NRP1-binding peptide fused EGFR-targeting antibody can or the combination of NRP1-binding peptide-fused Fc and EGFR-targeting antibody can overcome the resistance to the EGFR-targeting antibody alone.
by: i) reducing the expression level of active integrin β1 on the cell surface, thereby inhibiting the phosphorylation of Src and Akt; or ii) regulating the expression amount of NRP1 and integrin β3 on the cell surface.

In one example of the present invention, it was shown that as the peptide did bind specifically to neuropilin-1 in pancreatic cancer, it reduced the expression of active integrin β1 on the cell surface, which results from the endocytosis of NRP1/active integrin β1. In addition, it was shown that the peptide inhibited the integrin β1-induced phosphorylation of FAK, Src and Akt. Accordingly, it was confirmed that the peptide according to the present invention, which binds specifically to neuropilin-1, can overcome the resistance of cancer to an EGFR-targeting agent (e.g., cetuximab or panitumumab) and increase the sensitivity of cancer to the EGFR-targeting agent.

In another example of the present invention, it was confirmed that the peptide according to the present invention, which binds specifically to neuropilin-1, can overcome the resistance of lung cancer to an EGFR-targeting agent (e.g., cetuximab or panitumumab) and increase the sensitivity of lung cancer to the EGFR-targeting agent by regulating the expression amount of NRP1 and integrin β3 on the cell surface.

The EGFR-targeting agent may be a gene expression inhibitor or an activity inhibitor, and the type thereof is not limited. For example, it may be an EGFR expression inhibitor or an agent that inhibits expression of active integrin β1 and expression of FAK, Src and Akt. The expression inhibitor may be an antisense nucleotide, a small hairpin RNA (shRNA), a small interfering RNA (siRNA) or a ribozyme, which binds complementarily to the mRNA of a protein gene, and the activity inhibitor may be an EGFR activity inhibitor or an agent that inhibits the activity of integrin β1, FAK, Src and Akt, and may also be a compound, a peptide, a peptide mimic, a substrate analogue, an aptamer, an antibody, or an antagonist.

In one embodiment, the EGFR-targeting agent may be, for example, a compound that specifically inhibits EGFR activity, or an antibody or its fragment that binds specifically to EGFR, and the peptide may bind to the C-terminus of an antibody or its fragment.

Specifically, the EGFR-targeting agent may be one or more antibodies selected from the group consisting of cetuximab, panitumumab, zalutumumab, nimotuzumab, and matuzumab, or may be one or more selected from the group consisting of gefitinib, erlotinib, and lapatinib, but is not limited thereto.

The antibody fragment means the heavy-chain or light-chain domain of the antibody, or a fragment thereof. For example, the antibody fragment may be Fc, Fab, a heavy-chain constant region fragment (CH1, CH2, or CH3) of an antibody, a heavy-chain variable region fragment (VH), a light-chain constant region fragment (CL), a light-chain variable region fragment (VL), a single-chain variable fragment (scFv), or a fragment thereof. Preferably, the antibody fragment may be a heavy-chain constant region crystalizable fragment (Fc) composed of hinge-CH2-CH3 of the antibody.

Fab has a structure including variable regions of a light chain and a heavy chain, a constant region of the light chain, and a first constant region (CH1) of the heavy chain with one antigen-binding site. Fab' differs from Fab in that it has a hinge region containing one or more cysteine residues at the C-terminal of the heavy chain CH1 domain. The F(ab')$_2$ antibody is produced when the cysteine residue of the hinge region of the Fab' forms a disulfide bond.

An "Fv" fragment is an antibody fragment that contains complete antigen recognition and binding sites. Such region includes a heavy chain variable domain and a light chain variable domain, for example, dimers substantially tightly covalently associated with scFv.

"Single chain Fv" or "scFv" antibody fragment comprises VH and VL domains of the antibody. Such domains are within a single polypeptide chain. The Fv polypeptide may further include a polypeptide linker between the VH domain and the VL domain such that the scFv can form the desired structure for antigen binding.

A single chain Fv (scFv) is connected to a heavy chain variable region and a light chain variable region via a peptide linker by a covalent bond or directly at the C-terminal. Such an antibody fragment can be obtained using a protein hydrolyzing enzyme (for example, when the whole antibody is cleaved with papain, Fab can be obtained, and when whole antibody is cut with pepsin, F(ab')2 fragment can be obtained), and it can also be produced through gene recombinant technology.

The heavy chain constant region can be selected from any one isotype of gamma (γ), mu (μ), alpha (α), delta (δ), and epsilon (ε). Sub-classes have gamma 1 (γ1), gamma 2 (γ2), gamma 3 (γ3), gamma 4 (γ4), alpha 1 (α1), and alpha 2 (α2) types. A constant region of the light chain has kappa (κ) and lambda (λ) types.

The term "heavy chain" as used herein refers to a full-length heavy chain and fragments thereof including a variable region domain VH including an amino acid sequence with sufficient variable region sequence to confer specificity to an antigen and three constant region domains CH1, CH2, and CH3. The term "light chain" as used herein refers to a full-length heavy chain and fragments thereof including a variable region domain VL including an amino acid sequence with sufficient variable region sequence to confer specificity to an antigen and a constant region domain CL.

Moreover, the antibody fragment may be a monomer, a dimer, or a multimer. A peptide binding to the neuropilin-1 may bind to a heavy chain constant region (Fc) fragment of an antibody specific for EGFR, preferably to the C-terminus of of Fc.

According to an embodiment of the present invention, there is provided a strategy that targets both NRP1 and EGFR, by linking TPP11 (which is a peptide that binds specifically to NRP1) to the C-terminus of the heavy chain of each of cetuximab (Ctx) and panitumumab (Pnm), which are anti-EGFR antibodies that bind specifically to EGFR, suggesting that this strategy makes it possible to overcome resistance to the EGFR-targeting antibody.

The "linking" means integrating two molecules having different or same functions or structures, and may be used interchangeably with "fusing". It may be linking or fusing by all physical, chemical or biological methods by which the peptide can be linked.

In some cases, the peptide may further comprise a linker and may be linked to the EGFR-targeting agent. In one embodiment, the linker may be a peptide linker.

For example, a peptide linker comprising a sequence of (GGGGS)n SEQ ID NO: 16, (where n is an integer ranging from 1 to 20) may be linked to the EGFR-targeting antibody.

The composition of the present invention may be formulated using a pharmaceutically acceptable carrier and/or an excipient according to a method which can be easily carried out by those having ordinary skill in the art to which the present invention pertains so as to be provided in a unit dosage form or enclosed into a multi-dose container. Here, the formulations of the composition may be in the form of solutions, suspensions or emulsions in oils or aqueous media, or in the form of extracts, grains, suppositories, powders, granules, tablets or capsules, and may additionally include dispersing or stabilizing agents. Meanwhile, the composition includes an antibody or an antigen-binding fragment, and thus may be formulated into immuno liposome. Liposome including an antibody may be prepared according to a method well known in the pertinent art. The immuno liposome is a lipid composition including phosphatidylcholine, cholesterol and polyethyleneglycol-derived phosphatidylethanolamine, and may be prepared by reverse phase evaporation method. For example, a Fab' fragment of antibody may be conjugated to liposome through disulphide exchange reaction. Liposome may further include chemical therapeutic agents such as Doxorubicin.

The pharmaceutical composition of the present invention may be a pharmaceutical composition, and may be administered orally or parenterally. The parenteral administration is carried out by intravenous injection, subcutaneous injection, intramuscular injection, intraperitoneal injection, endothelial administration, topical administration, intranasal administration, intrapulmonary administration, rectal administration, and the like. Because a protein or peptide is digested when administered orally, a composition for oral administration should be formulated to coat an active drug agent or to be protected against degradation in stomach. Also, the composition may be administered by any device which can transport active substances to target cells.

In one embodiment, the present invention is directed to a method for treating cancer, which comprises: administering a composition comprising a peptide that binds specifically to neuropilin-1 to a subject in need of the treatment of cancer, thereby adjusting resistance or sensitivity to an EGFR (Epidermal Growth Factor Receptor)-targeting agent.

The appropriate dosage of the composition according to the present invention may vary depending on factors such as the formulation method, the administration method, patient's age, body weight, sex, pathological condition, food, administration time, route of administration, excretion rate and reaction sensitivity. Preferably, a proper dosage of the composition is within the range of 0.001 and 100 mg/kg based on an adult. The term "pharmaceutically effective dose" as used herein refers to an amount sufficient to prevent or treat cancer or angiogenesis-related diseases.

The composition and the treatment method according to the present invention are applied to cancer. The cancer is cancer that can be treated by an EGRF-targeting anticancer drug, and examples of the cancer include, but are not limited to, ACTH-producing tumor, acute lymphocytic or lymphoblastic leukemia, acute or chronic lymphoblastic leukemia, acute non-lymphoblastic leukemia, bladder cancer, brain tumor, breast cancer, carcinoma of the cervix, chronic myelogenous leukemia, kidney cancer, T-zone lymphoma, endometriosis, esophageal cancer, gallbladder cancer, Ewing's sarcoma, head and neck cancer, tongue cancer, Hodgkin's lymphoma, Kaposi's sarcoma, kidney cancer, liver cancer, lung cancer, mesothelioma, multiple myeloma, neuroblastoma, non-Hodgkin Lymphoma, osteosarcoma, ovarian cancer, ductal carcinoma in situ, prostate cancer, pancreatic cancer, colorectal cancer, penis cancer, retinoblastoma, skin cancer, gastric cancer, thyroid cancer, uterine cancer, testicular cancer, Wilms' tumor, and trophoblastoma. Most preferably, the cancer may be pancreatic cancer or lung cancer.

In one embodiment, the cancer may be cancer in which NRP1 is expressed. In one example of the present invention, it was shown that EGFR and NRP1 were expressed in tumor cells, and in non-NRP1-expressing cell lines, the peptide that binds specifically to NRP1 did not reduce resistance to the EGFR-targeting antibody. Accordingly, it was confirmed that expression of NRP1 should be premised so that the peptide that binds specifically to NRP1 can reduce resistance to the EGFR-targeting antibody.

In still another aspect, the present invention is directed to an anticancer drug or an anticancer adjuvant comprising the composition. The composition can exhibit direct anticancer effects through a composition comprising the peptide according to the present invention (e.g., a peptide itself or Fc fragment), which binds specifically to neuropilin-1, or it may be used as an anticancer adjuvant that reduces resistance to other anticancer drugs (e.g., EGFR-targeting antibody Ctx or Pnm) and increases sensitivity to the anticancer drugs.

In yet another aspect, the present invention is directed to a composition for co-administration for cancer treatment, which comprises: a Fc-fused peptide that binds specifically to neuropilin-1 and an EGFR-targeting antibody, the combination of which can overcome the resistance to the EGFR-targeting antibody alone. The present invention is also directed to a method for treating cancer, which comprises co-administering a composition comprising a NRP1-binding peptide-fused Fc and an EGFR-targeting antibody, the combination of which can overcome the resistance to the EGFR-targeting antibody alone.

When the Fc-fused peptide that binds specifically to neuropilin-1 is co-administered with the EGFR-targeting antibody, the NRP1-binding peptide fused Fc may act as a sensitizer to reduce resistance to the EGFR-targeting antibody and to increase sensitivity to the EGFR-targeting antibody, thereby improving the cancer treatment effect of the EGFR-targeting antibody alone.

The composition for co-administration includes the NRP1-binding peptide fused Fc, and the components related thereto are the same as the components included in the above-described composition and treatment method. Thus, the description of each constitution applies equally to the method of treating cancer by co-administration.

As used herein, the term "co-administration" means that the peptide specifically binding to neuropilin-1 and the EGFR-targeting agent may be administered simultaneously, sequentially, or in reverse order, and the NRP1-binding peptide fused Fc and the EGFR-targeting antibody may be administered in a combination of appropriate effective amounts of the active ingredients within the range determined by those skilled in the art. For example, the NRP1-binding peptide fused Fc and the EGFR-targeting antibody may be respectively stored in separate containers, and then administered simultaneously, sequentially, or in reverse order.

EXAMPLES

Hereinafter, the present invention will be described in further detail with reference to examples. It will be obvious to a person having ordinary skill in the art that these examples are for illustrative purposes only and are not to be construed to limit the scope of the present invention.

Example 1: Analysis of Characteristics of Pancreatic Cancer Cell Lines Having or not Having Intrinsic Resistance to Ctx The characteristics of pancreatic cancer cell lines used in the present invention, which have or do not have intrinsic resistance to Ctx, were analyzed. This may be an important marker that predicts whether pancreatic cancer has intrinsic resistance to Ctx.

FIG. 1a shows the results of flow cytometry (FACS) analysis performed to analyze the cell surface expression levels of EGFR, NRP1 and integrin-β1 in four pancreatic cancer cell lines (BxPC-3, PANC-1, Capan-2, and SW1990) having intrinsic resistance to Ctx and in two pancreatic cancer cell lines (Miapaca-2, and AsPC-1) not resistant to Ctx.

Specifically, Miapaca-2, AsPC-1, BxPC-3, PANC-1, Capan-2 and SW1990 cell lines were prepared at a density of $2 \times 10^5$ per sample. The cells were washed with PBS, and incubated with an antibody (R&D System) recognizing NRP1 and an FITC-conjugated antibody (e-Bioscience) recognizing each of EGFR and integrin β1 at 4° C. for 1 hour. Additionally, the NRP1 antibody bound to the cells were stained with the FITC-conjugated antibody, and then washed with PBS, followed by analysis with a flow cytometer (FACS Calibur) (BD Bioscience).

FIG. 1b shows the results of Western blot analysis performed to analyze the whole cell expression levels of EGFR, NRP1 and integrin-β1 in the cell lines used in FIG. 1a.

Specifically, each of Miapaca-2, AsPC-1, BxPC-3, PANC-1, Capan-2 or SW1990 cell lines was added to each well of 6-well plates at a density of $6 \times 10^5$ cells per well and cultured in 1 ml of 10% FBS-containing medium for 24 hours under 5% $CO_2$ at 37° C. After the culture, lysis buffer (10 mM Tris-HCl pH 7.4, 100 mM NaCl, 1% SDS, 1 mM EDTA, inhibitor cocktail (Sigma)) was added to obtain cell lysate. The cell lysate was quantified using a BCA protein assay kit. After performing SDS-PAGE, the gel was transferred to a PVDF membrane, and incubated with antibodies (SantaCruz), which recognize NRP1, EGFR, integrin β1 and β-actin, respectively, at 25° C. for 2 hours, and then incubated with HRP-conjugated secondary antibodies (SantaCruz) at 25° C. for hour, followed by detection. Analysis was performed using ImageQuant LAS4000 mini (GE Healthcare).

As a result, as shown in FIGS. 1a and 1b, the cell surface and whole cell expression levels of integrin β1 were higher in $Ctx^R$ pancreatic cancer cell lines than in $Ctx^S$ pancreatic cancer cell lines, unlike NRP1 and EGFR.

FIG. 1c shows the results of Western blot analysis of the whole expression levels and phosphorylation levels of EGFR, Akt, Src and ERK in $Ctx^S$ and $Ctx^R$ pancreatic cancer cell lines after treatment with various concentrations of Ctx.

As shown in FIG. 1b, each of Miapaca-2, AsPC-1, BxPC-3, PANC-1 and SW1990 cell lines was added to 6-well plates at a density of $4 \times 10^5$ cells per well and cultured in 10% FBS-containing medium for 12 hours. Then, Ctx was diluted in 1 ml of 10% FBS at a concentration of 1 μM or 0.1 μM, and the cells were incubated with the dilution for 24 hours under 5% $CO_2$ at 37° C. After incubation, the cells were washed with cold PBS, and then lysis buffer (10 mM Tris-HCl pH 7.4, 100 mM NaCl, 1% SDS, 1 mM EDTA, inhibitor cocktail (Sigma)) was added thereto to obtain cell lysate. For Western blot analysis, the cell lysate was incubated with antibodies, which recognize pEGFR (Y1173), EGFR, pFAK, FAK, pSrc, Src, pAkt, Akt, pERK1/2, ERK1/2 and β-actin, respectively, at 4° C. for 12 hours, and incubated with HRP-conjugated secondary antibodies (SantaCruz) at 25° C. for 1 hour, followed by analysis.

As a result, $Ctx^R$ pancreatic cancer cell lines maintain high phosphorylation levels of FAK, Src and Akt, even when they were treated with Ctx, unlike $Ctx^S$ pancreatic cancer cell lines. However, phosphorylation levels of EGFR (Y1173) and ERK1/2 showed no difference between the $Ctx^S$ pancreatic cancer cell lines and the $Ctx^R$ pancreatic cancer cell lines.

Example 2: Examination of the Effects of Inhibition of Integrin β1 Expression and Inhibition of Phosphorylation of Src and Akt on the Resistance of Pancreatic Cancer to Ctx It was found that the expression level of integrin β1 and the phosphorylation levels of Src and Akt were higher in the $Ctx^R$ pancreatic cancer cell lines than in the $Ctx^S$ cell lines. In fact, whether the resistance of the $Ctx^R$ pancreatic cancer cell lines to Ctx is associated with overexpressed integrin β1, Src and Akt was examined.

FIG. 2a shows the results of examining cell viability after Ctx treatment in $Ctx^R$ cell lines (cell line BxPC-3 expressing NRP1, cell line PANC-1, and cell line SW1990 not expressing NRP1) treated with each of control siRNA and integrin β1 siRNA.

Specifically, $3 \times 10^5$ BxPC-3, PANC-1 or SW1990 cells were added to and cultured in each well of 6-well plates, and then subjected to transient transfection with siRNA. For transient transfection, 100 nM of each of a control siRNA having no target and an siRNA targeting the inhibition of integrin β1 expression was incubated with 500 μl of Opti-MEM media (Gibco) and 3.5 μl of RNAiMax (Invitrogen, USA) in a tube at room temperature for 15 minutes, and then added to each well. In addition, 500 μl of antibiotic-free DMEM medium was added to each well which was then incubated for 6 hours at 37° C. under 5% $CO_2$, followed by replacement with 1 ml of 10% FBS-containing DMEM medium. After 24 hours of incubation, $7 \times 10^3$ cells were added to each well of 96-well plates and incubated for 12 hours. Then, Ctx was diluted in 10% FBS-containing medium at a concentration of 2 μM, and the cells were incubated with the dilution for 48 hours. Next, for a cell proliferation assay, 20 μl of MTT reagent (Sigma) was added to each well, followed by incubation at 37° C. for 2 hours. The formed formazan was dissolved in DMSO, and the absorbance at 570 nm was measured using a microplate reader (Molecular Devices).

FIG. 2b shows the results of Western blot analysis performed to confirm that expression of integrin β1 in the cell lysate obtained after transient transfection in FIG. 2a was specifically inhibited.

FIG. 2c shows the results of examining cell viability in $Ctx^R$ cell lines after treatment with Ctx in combination with each of a PI3K-Akt inhibitor (LY294002), an Src inhibitor (SU6656) and an Raf inhibitor (Sorafenib).

Specifically, each of BxPC-3 and PANC-1 cell lines was added to 96-well plates at a density of $7 \times 10^3$ cells per well and cultured in 10% FBS-containing medium for 12 hours. Then, each of 50 μM LY294002, 5 μM SU6656 and 2.5 μM sorafenib was diluted together with 2 μM Ctx, and the cells were incubated with the dilution for 72 hours. Then, cell viability was analyzed by MTT assay.

As a result, it could be seen that, regardless of expression of NRP1 in pancreatic cancer, inhibiting the expression of integrin β1 or inhibiting the phosphorylation of Src and Akt could overcome resistance to Ctx. However, when phosphorylation of Raf was inhibited, resistance to Ctx could not be overcome. This suggests that, independently of the signaling pathway of KRas-BRaf, the signaling pathways of integrin β1, Src and Akt may be major markers of resistance to Ctx.

Table 1 summarizes the results of analyzing the characteristics of the pancreatic cancer cell lines used in the present invention. The cell surface expression levels shown were classified by the FACS results shown in FIG. 1a and the MFI values. (+: low expression level, ++: moderate expression level, +++: high expression level).

TABLE 1

| Cell lines | Mutational state | | | Cell surface expression levels | | | Responsiveness to Cetuximab |
|---|---|---|---|---|---|---|---|
| | EGFR | KRAS | BRAF | NRP1 | EGFR | Integrin β1 | |
| Miapaca-2 | WT | G12C | WT | − | + | + | Sensitive |
| AsPC-1 | WT | G12D | WT | + | ++ | + | Sensitive |
| BxPC-3 | WT | WT | WT | + | +++ | ++ | Resistant |
| PANC-1 | WT | G12D | WT | ++ | ++ | ++ | Resistant |
| Capan-2 | WT | G12V | WT | + | ++ | +++ | Resistant |
| SW1990 | WT | G12D | WT | − | ++ | ++ | Resistant |

Example 3: Expression and Purification of Ctx-TPP11

In order to examine whether Ctx-TPP11 can inhibit the proliferation of Ctx$^R$ pancreatic cancer cells, Ctx-TPP11 was expressed and purified.

Specifically, for a vector for producing a fusion protein composed of a TPP11 peptide and an antibody heavy-chain constant region (Fc), the DNA of the TPP11-fused portion in the antibody heavy-chain constant region (amino acid (AA) sequence of SEQ ID NO: 4, and DNA sequence of SEQ ID NO: 5) obtained by treatment with BsrGI and HindIII restriction enzymes was cloned into a vector encoding a wild-type Ctx heavy chain (AA sequence of SEQ ID NO: 6; DNA sequence of SEQ ID NO: 7). As a light chain-encoding DNA (AA sequence of SEQ ID NO: 8, and DNA sequence of SEQ ID NO: 9), a wild-type Ctx light chain expression vector was used.

TABLE 2

| Constitution | Sequences | SEQ ID NO: |
|---|---|---|
| Heavy chain amino acid sequence of Ctx-TPP11 | MGWSCIILFLVATATGVHSQVQLKQSGPGLVQ PSQSLSITCTVSGFSLTNYGVHWVRQSPGKGL EWLGVIWSGGNTDYNTPFTSRLSINKDNSKSQ VFFKMNSLQSNDTAIYYCARALTYYDYEFAYW GQGTLVTVSAASTKGPSVFPLAPSSKSTSGGT AALGCLVKDYFPEPVTVSWNSGALTSGVHTFP AVLQSSGLYSLSSVVTVPSSSLGTQTYICNVN HKPSNTKVDKKVEPKSCDKTHTCPPCPAPELL GGPSVFLFPPKPKDTLMISRTPEVTCVVVDVS HEDPEVKFNWYVDGVEVHNAKTKPREEQYNST YRVVSVLTVLHQDWLNGKEYKCKVSNKALPAP IEKTISKAKGQPREPQVYTLPPSRDELTKNQV SLTCLVKGFYPSDIAVEWESNGQPENNYKTTP PVLDSDGSFFLYSKLTVDKSRWQQGNVFSCSV MHEALHNHYTQKSLSLSPGKGGGGSGGGGSGG GGSHTPGNSKPTRTPRR | SEQ ID NO: 4 |
| Heavy chain DNA sequence of Ctx-TPP11 | CAGGTGCAGCTGAAACAGAGCGGCCCGGGCCT GGTGCAGCCGAGCCAGAGCCTGAGCATTACCT GCACCGTGAGCGGCTTTAGCCTGACCAACTAT GGCGTGCATTGGGTGCGCCAGAGCCCGGGCAA AGGCCTGGAATGGCTGGGCGTGATTTGGAGCG GCGGCAACACCGATTATAACACCCCGTTTACC AGCCGCCTGAGCATTAACAAAGATAACAGCAA AAGCCAGGTGTTTTTTAAAATGAACAGCCTGC AGAGCAACGATACCGCGATTTATTATTGCGCG CGCGCGCTGACCTATTATGATTATGAATTTGC GTATTGGGGCCAGGGCACCCTGGTGACCGTGA GCGCGGCCTCCACCAAGGGCCCATCGGTCTTC CCCCTGGCACCCTCCTCCAAGAGCACCTCTGG GGGCACAGCGGCCCTGGGCTGCCTGGTCAAGG ACTACTTCCCCGAACCGGTGACGGTGTCGTGG AACTCAGGCGCCCTGACCAGCGGCGTGCACAC CTTCCCGGCTGTCCTACAGTCCTCAGGACTCT ACTCCCTCAGCAGCGTGGTGACCGTGCCCTCC AGCAGCTTGGGCACCCAGACCTACATCTGCAA CGTGAATCACAAGCCCAGCAACACCAAGGTGG ACAAGAAAGTTGAGCCCAAATCTTGTGACAAA ACTCACACATGCCCACCGTGCCCAGCACCTGA ACTCCTGGGGGGACCGTCAGTCTTCCTCTTCC CCCCAAAACCCAAGGACACCCTCATGATCTCC CGGACCCCTGAGGTCACATGCGTGGTGGTGGA CGTGAGCCACGAAGACCCTGAGGTCAAGTTCA ACTGGTACGTGGACGGCGTGGAGGTGCATAAT GCCAAGACAAAGCCGCGGGAGGAGCAGTACAA CAGCACGTACCGTGTGGTCAGCGTCCTCACCG TCCTGCACCAGGACTGGCTGAATGGCAAGGAG TACAAGTGCAAGGTCTCCAACAAAGCCCTCCC AGCCCCCATCGAGAAAACCATCTCCAAAGCCA AAGGGCAGCCCCGAGAACCACAGGTGTACACC CTGCCCCCATCCCGGGATGAGCTGACCAAGAA CCAGGTCAGCCTGACCTGCCTGGTCAAAGGCT TCTATCCCAGCGACATCGCCGTGGAGTGGGAG AGCAATGGGCAGCCGGAGAACAACTACAAGAC CACGCCTCCCGTGCTGGACTCCGACGGCTCCT TCTTCCTCTACAGCAAGCTCACCGTGGACAAG AGCAGGTGGCAGCAGGGGAACGTCTTCTCATG CTCCGTGATGCATGAGGCTCTGCACAACCACT ACACGCAGAAGAGCCTCTCCCTGTCCCCGGGT AAAGGTGGAGGAGGATCTGGAGGAGGAGGAAG TGGAGGTGGAGGATCACATACTCCTGGAAATA GCAAACCAACACGCACACCAAGGCGT | SEQ ID NO: 5 |
| Heavy chain amino acid sequence of Ctx | MGWSCIILFLVATATGVHSQVQLKQSGPGLVQ PSQSLSITCTVSGFSLTNYGVHWVRQSPGKGL EWLGVIWSGGNTDYNTPFTSRLSINKDNSKSQ | SEQ ID NO: 6 |

TABLE 2-continued

| Constitution | Sequences | SEQ ID NO: |
|---|---|---|
| | VFFKMNSLQSNDTAIYYCARALTYYDYEFAYW GQGTLVTVSAASTKGPSVFPLAPSSKSTSGGT AALGCLVKDYFPEPVTVSWNSGALTSGVHTFP AVLQSSGLYSLSSVVTVPSSSLGTQTYICNVN HKPSNTKVDKKVEPKSCDKTHTCPPCPAPELL GGPSVFLFPPKPKDTLMISRTPEVTCVVVDVS HEDPEVKFNWYVDGVEVHNAKTKPREEQYNST YRVVSVLTVLHQDWLNGKEYKCKVSNKALPAP IEKTISKAKGQPREPQVYTLPPSRDELTKNQV SLTCLVKGFYPSDIAVEWESNGQPENNYKTTP PVLDSDGSFFLYSKLTVDKSRWQQGNVFSCSV MHEALHNHYTQKSLSLSPGK | |
| Heavy chain DNA sequence of Ctx | CAGGTGCAGCTGAAACAGAGCGGCCCGGGCCT GGTGCAGCCGAGCCAGAGCCTGAGCATTACCT GCACCGTGAGCGGCTTTAGCCTGACCAACTAT GCACGTGCATTGGGTGCGCCAGAGCCCGGGCAA AGGCCTGGAATGGCTGGGCGTGATTTGGAGCG GCGGCAACACCGATTATAACACCCCGTTTACC AGCCGCCTGAGCATTAACAAAGATAACAGCAA AAGCCAGGTGTTTTTTAAAATGAACAGCCTGC AGAGCAACGATACCGCGATTTATTATTGCGCG CGCGCGCTGACCTATTATGATTATGAATTTGC GTATTGGGGCCAGGGCACCCTGGTGACCGTGA GCGCGGCCTCCACCAAGGGCCCATCGGTCTTC CCCCTGGCACCCTCCTCCAAGAGCACCTCTGG GGGCACAGCGGCCCTGGGCTGCCTGGTCAAGG ACTACTTCCCCGAACCGGTGACGGTGTCGTGG AACTCAGGCGCCCTGACCAGCGGCGTGCACAC CTTCCCGGCTGTCCTACAGTCCTCAGGACTCT ACTCCCTCAGCAGCGTGGTGACCGTGCCCTCC AGCAGCTTGGGCACCCAGACCTACATCTGCAA CGTGAATCACAAGCCCAGCAACACCAAGGTGG ACAAGAAAGTTGAGCCCAAATCTTGTGACAAA ACTCACACATGCCCACCGTGCCCAGCACCTGA ACTCCTGGGGGGACCGTCAGTCTTCCTCTTCC CCCCAAAACCCAAGGACACCCTCATGATCTCC CGGACCCCTGAGGTCACATGCGTGGTGGTGGA CGTGAGCCACGAAGACCCTGAGGTCAAGTTCA ACTGGTACGTGGACGGCGTGGAGGTGCATAAT GCCAAGACAAAGCCGCGGGAGGAGCAGTACAA CAGCACGTACCGTGTGGTCAGCGTCCTCACCG TCCTGCACCAGGACTGGCTGAATGGCAAGGAG TACAAGTGCAAGGTCTCCAACAAAGCCCTCCC AGCCCCCATCGAGAAAACCATCTCCAAAGCCA AAGGGCAGCCCCGAGAACCACAGGTGTACACC CTGCCCCCATCCCGGGATGAGCTGACCAAGAA CCAGGTCAGCCTGACCTGCCTGGTCAAAGGCT TCTATCCCAGCGACATCGCCGTGGAGTGGGAG AGCAATGGGCAGCCGGAGAACAACTACAAGAC CACGCCTCCCGTGCTGGACTCCGACGGCTCCT TCTTCCTCTACAGCAAGCTCACCGTGGACAAG AGCAGGTGGCAGCAGGGGAACGTCTTCTCATG CTCCGTGATGCATGAGGCTCTGCACAACCACT ACACGCAGAAGAGCCTCTCCCTGTCCCCGGGT AAA | SEQ ID NO: 7 |
| Light chain amino acid sequence of Ctx | MGWSCIILFLVATATGVHSDILLTQSPVILSV SPGERVSFSCRASQSIGTNIHWYQQRTNGSPR LLIKYASESISGIPSRFSGSGSGTDFTLSINS VESEDIADYYCQQNNWPTTFGAGTKLELKRT VAAPSVFIFPPSDEQLKSGTASVVCLLNNFYP REAKVQWKVDNALQSGNSQESVTEQDSKDSTY SLSSTLTLSKADYEKHKVYACEVTHQGLSSPV TKSFNRGEC | SEQ ID NO: 8 |
| Light chain DNA sequence of Ctx | GATATTCTGCTGACCCAGAGCCCGGTGATTCT GAGCGTGAGCCCGGGCGAACGCGTGAGCTTTA GCTGCCGCGCGAGCCAGAGCATTGGCACCAAC ATTCATTGGTATCAGCAGCGCACCAACGGCAG CCCGCGCCTGCTGATTAAATATGCGAGCGAAA GCATTAGCGGCATTCCGAGCCGCTTTAGCGGC AGCGGCAGCGGCACCGATTTTACCCTGAGCAT TAACAGCGTGGAAAGCGAAGATATTGCGGATT ATTATTGCCAGCAGAACAACAACTGGCCGACC ACCTTTGGCGCGGGCACCAAACTGGAACTGAA ACGTACGGTGGCTGCACCATCTGTCTTCATCT TCCCGCCATCTGATGAGCAGTTGAAATCTGGA | SEQ ID NO: 9 |

TABLE 2-continued

| Constitution | Sequences | SEQ ID NO: |
|---|---|---|
| | ACTGCCTCTGTTGTGTGCCTGCTGAATAACTT<br>CTATCCCAGAGAGGCCAAAGTACAGTGGAAGG<br>TGGATAACGCCCTCCAATCGGGTAACTCCCAG<br>GAGAGTGTCACAGAGCAGGACAGCAAGGACAG<br>CACCTACAGCCTCAGCAGCACCCTGACGCTGA<br>GCAAAGCAGACTACGAGAAACACAAAGTCTAC<br>GCCTGCGAAGTCACCCATCAGGGCCTGAGCTC<br>GCCCGTCACAAAGAGCTTCAACAGGGGAGAGT<br>GTTGA | |

The light-chain and heavy-chain expression vectors were subjected to transient transfection, thereby expressing and purifying protein. In a shaking flask, HEK293-F cells (Invitrogen) suspension-growing in serum-free FreeStyle 293 expression medium (Invitrogen) were transfected with a mixture of a plasmid and polyethylenimine (PEI) (Polyscience). For 200 mL transfection in a shaking flask (Corning), HEK293-F cells were seeded into 100 ml of medium at a density of $2\times10^6$ cells/ml and cultured at 130 rpm under 8% $CO_2$. Heavy-chain and light-chain plasmids suitable for producing each monoclonal antibody were diluted in 10 ml of FreeStyle 293 expression medium (Invitrogen) to 125 μg heavy chain and 125 μg light chain (a total of 250 μg (2.5 μg/ml)), and the dilution was mixed with 10 ml of medium containing 750 μg (7.5 μg/ml) of PEI and was incubated at room temperature for 10 minutes. Next, the incubated mixed medium was added to 100 ml of the above-seeded cells and incubated for 4 hours at 150 rpm under 8% $CO_2$, and then the remaining 100 ml of FreeStyle 293 expression medium was added thereto, followed by incubation for 7 days. With reference to a standard protocol, protein was purified from the collected cell culture supernatant. Antibody was applied to a Protein A Sepharose column (GE healthcare), followed by washing with PBS (pH 7.4). The antibody was eluted with 0.1 M glycine buffer at pH 3.0, and then the sample was immediately neutralized with 1M Tris buffer. The eluted antibody fraction was concentrated by dialysis while replacing buffer with PBS (pH 7.4). The purified protein was quantified using the absorbance at 280 nm and absorption coefficient.

Example 4: Evaluation of the Simultaneous Binding Affinity of Ctx-TPP11 for Both NRP1 and EGFR The binding affinity of Ctx-TPP11 (expressed and purified in Example 2) for EGFR and NRP1-b1b2 was analyzed comparatively with that of wild-type antibody Ctx.

FIG. 3b shows the results of sandwich ELISA performed to confirm that the constructed Ctx-TPP11 has a binding affinity for both EGFR and NRP1-b1b2 in comparison with Fc-TPP11 and Ctx.

Specifically, EGFR (0.5 μg/well) was coated on a 96-well plate (SPL, Korea) for 1 hour, and then incubated with each of Fc-TPP11, Ctx and Ctx-TPP11 (10 nM) at 25° C. for 1 hour. After washing with TBST (TBS with 0.1% Tween-20), each well was incubated with serially diluted biotinylated NRP1-b1b2 (1 μM-1 pM) at 25° C. for 1 hour, and then bound with AP-conjugated goat anti-biotin antibody at 25° C. for 1 hour. Next, the bound biotinylated protein was detected using a p-nitrophenyl phosphate substrate (Sigma-Aldrich), and the absorbance at 405 nm was measured using a microplate reader.

Table 3 below shows the results of SPR (Surface plasmon resonance) performed using the Biacore2000 instrument (GE healthcare) in order to more quantitatively analyze the binding affinity of Ctx-TPP11 for NRP1-b1b2 and EGFR in comparison with Fc-TPP11 and Ctx.

Specifically, each of Fc-TPP11, Ctx and Ctx-TPP11 protein was immobilized on a CM5 sensor chip (GE healthcare, USA) at a level of about 1,000 response units (RUs). For analysis, HBS-EP buffer [10 mM Hepes, 3 mM ethylenediaminetetraacetic acid, 0.005% surfactant P20 (pH 7.6), GE Healthcare] was used at a flow rate of 30 μl/min, and treatment with NRP1-b1b2 protein was performed. After analysis of association and dissociation, regeneration of the CM5 chip was performed by running buffer (20 mM NaOH, 1M NaCl, pH10.0) at a flow rate of 30 μl/min for 2 minutes. Each sensorgram obtained for 3 min of association and 6 min of dissociation was normalized relative to a blank cell and subtracted, thereby calculating the affinity.

TABLE 3

| | Antibodies | $k_{on}$ $(M^{-1}s^{-1})$ | $k_{off}(s^{-1})$ | $K_D$ (nM) |
|---|---|---|---|---|
| EGFR | Cetuximab | $(3.77 \pm 1.34) \times 10^5$ | $(5.36 \pm 0.90) \times 10^{-4}$ | $(1.64 \pm 0.96) \times 10^{-9}$ |
| | Ctx-TPP11 | $(3.50 \pm 0.80) \times 10^5$ | $(5.30 \pm 0.64) \times 10^{-4}$ | $(1.57 \pm 0.44) \times 10^{-9}$ |
| NRP1-b1b2 | Fc-TPP11 | $(5.38 \pm 1.12) \times 10^4$ | $(8.65 \pm 0.61) \times 10^{-4}$ | $(1.62 \pm 0.23) \times 10^{-8}$ |
| | Ctx-TPP11 | $(6.69 \pm 2.00) \times 10^4$ | $(9.85 \pm 0.82) \times 10^{-4}$ | $(1.55 \pm 0.38) \times 10^{-8}$ |

As shown in Table 3 above, the affinity for EGFR was the same between TPP11-fused Ctx-TPP11 and wild-type antibody Ctx, and the affinity for NRP1-b1b2 was also the same between Ctx-TPP11 and Fc-TPP11. For analysis, at least five sensorgrams were used, and the results obtained in triplicate were statistically processed. ± indicates the results of independent experiments and standard deviation values.

Example 5: Evaluation of Cell Growth Inhibitory Ability of Ctx-TPP11 in $Ctx^R$ Pancreatic Cancer Cell Lines In order to examine whether Ctx-TPP11 that targets NRP1 and EGFR can inhibit the proliferation of $Ctx^R$ pancreatic cancer cells that express NRP1, a cell growth assay was performed on various cell lines.

FIG. 4a shows the results of an MTT assay performed to measure cell proliferation in $Ctx^S$ (Miapaca-2, AsPC-1) and $Ctx^R$ (BxPC-3, PANC-1, Capan-2, SW1990) pancreatic cancer cell lines after treatment with various concentrations of Fc-TPP11, Ctx and Ctx-TPP11.

Specifically, pancreatic cancer cell lines were prepared in the same manner as described in Example 2. When the cells were stabilized, the cells were treated with various concentrations (0, 1, 2, 4 µM) of each of Fc-TPP11, Ctx and Ctx-TPP11 twice at 48-hour intervals and incubated for a total of 96 hours. In addition, in order to examine whether the inhibition of cell proliferation would result from targeting both NRP1 and EGFR, the cells were co-treated with the same concentration of Fc-TPP11 and Ctx and then incubated. In the same manner as described in Example 2, 20 µl of MTT reagent (Sigma) was added to each well which was then incubated at 37° C. for 2 hours, and the formed formazan was dissolved in DMSO. The absorbance at 570 nm was measured using a microplate reader (Molecular Devices). In $Ctx^S$ (Miapaca-2, AsPC-1) pancreatic cancer cell lines, Ctx and Ctx-TPP11 showed the same cell growth inhibitory ability, and in three $Ctx^R$ (BxPC-3, PANC-1, Capan-2) pancreatic cancer cell lines, Ctx-TPP11 and a combination of Fc-TPP11 and Ctx showed cell growth inhibition, unlike Ctx. However, as confirmed in Example, in SW1990 which is a $Ctx^R$ pancreatic cancer cell line expressing no NRP1, Ctx-TPP11 showed no effect. This suggests that Ctx-TPP11 shows an effect specific for its target NRP1.

In addition, in order to examine whether the inhibition of $Ctx^R$ pancreatic cancer cell proliferation by Ctx-TPP11 is attributable to induction of apoptosis, an apoptosis assay was performed.

FIGS. 4b and 4c show the results of analysis performed using an Annexin V-FITC apoptosis detection kit (BD Biscience) in order to analyze apoptosis of $Ctx^S$ (Miapaca-2, AsPC-1) and $Ctx^R$ (BxPC-3, PANC-1) pancreatic cancer cell lines after treatment with Fc-TPP11, Ctx and Ctx-TPP11.

Specifically, $2\times10^5$ Miapaca-2, AsPC-1, BxPC-3 or PANC-1 cells were cultured in each well of 12-well plates. When the cells were stabilized, the cells were treated with 4 µM of each of Fc-TPP11, Ctx and Ctx-TPP11 and incubated for a total of 48 hours. Next, the cells were washed with cold PBS. $1\times10^6$ cells were prepared per sample, and 5 µl of annexin V-FITC and 5 µl of propidium iodide were added thereto, followed by incubation at 25° C. for 15 minutes. Next, 400 µl of 1× binding buffer was added to each sample, followed by analysis with the flow cytometer FACS Calibur (BD Bioscience). The above-described experiment was performed in accordance with the manufacturer's protocol.

After analysis, a dot plot for each sample is shown in FIG. 4b. In addition, based on the dot plot, the number of dead cells stained only with annexin V was expressed as a percentage (%) relative to the total cell number, and the results are quantitatively shown in FIG. 4c.

In the $Ctx^S$ (Miapaca-2, AsPC-1) pancreatic cancer cell lines, Ctx and Ctx-TPP11 induced apoptosis in the same manner, and in the $Ctx^R$ (BxPC-3, PANC-1) pancreatic cancer cell lines, Ctx-TPP11 and a combination of Fc-TPP11 and Ctx induced apoptosis, unlike Ctx. This suggests that the inhibition of proliferation of $Ctx^R$ pancreatic cancer cells by Ctx-TPP11 is attributable to induction of apoptosis.

FIG. 4d shows the effects of evaluating the effects of NRP1, integrin-β1 and cMet siRNA on the inhibition of cell proliferation of $Ctx^R$ pancreatic cancer cell lines.

Specifically, cells were prepared in the same manner as described in Example 2 and were subjected to transient transfection with siRNA. For transient transfection, 100 nM of each of a control siRNA having no target and an siRNA targeting the inhibition of integrin β1 expression was incubated with 500 µl of Opti-MEM media (Gibco) and 3.5 µl of RNAiMax (Invitrogen, USA) in a tube at room temperature for 15 minutes, and then added to each well. In addition, 500 µl of antibiotic-free DMEM medium was added to each well which was then incubated for 6 hours at 37° C. under 5% $CO_2$, followed by replacement with 1 ml of 10% FBS-containing DMEM medium. After 24 hours of incubation, $7\times10^3$ cells were added to each well of 96-well plates and incubated for 12 hours. Then, each of Fc-TPP11, Ctx and Ctx-TPP11 was diluted in 10% FBS-containing medium at a concentration of 2 µM, and the cells were incubated with the dilution for 48 hours. Next, for a cell proliferation assay, 20 µl of MTT reagent (Sigma) was added to each well, and the absorbance at 570 nm was measured using a microplate reader (Molecular Devices). When expression of NRP1 was inhibited, the cell growth inhibitory ability of Ctx-TPP11 disappeared, but resistance to Ctx still appeared. In addition, inhibition of cMet expression could not overcome resistance to Ctx. However, as shown in FIG. 2a, when expression of integrin β1 was inhibited, resistance to Ctx was overcome.

FIGS. 4e and 4f show the results of Western blot analysis performed on the cell lysate, obtained after transient transfection in FIG. 4d, in order to confirm that NRP1 siRNA and cMet siRNA inhibited the expression of NRP1 and cMet.

Example 6: Evaluation of $Ctx^R$ Inhibitory Signal of Ctx-TPP11

In order to confirm whether resistance to $Ctx^R$ is overcome by Ctx-TPP11 because Ctx-TPP11 inhibits the expression of the resistance marker integrin β1 identified in Example 1 and the phosphorylation of FAK, Src and Akt which are signaling factors downstream of integrin β1, the signal inhibitory effects of Ctx-TPP11 with control siRNA and integrin β1 siRNA were examined.

FIGS. 5a and 5b shows the results of Western blot analysis performed to evaluate the signal inhibitory effects of Fc-TPP11, Ctx and Ctx-TPP11 on $Ctx^R$ pancreatic cancer cell lines after treatment with control siRNA and integrin β1 siRNA.

Specifically, cells were prepared in the same manner as described in Example 2 and were subjected to transient transfection with siRNA. For transient transfection, 100 nM of each of a control siRNA having no target and an siRNA targeting the inhibition of integrin β1 expression was incubated with 500 µl of Opti-MEM media (Gibco) and 3.5 µl of RNAiMax (Invitrogen, USA) in a tube at room temperature for 15 minutes, and then added to each well. In addition, 500 µl of antibiotic-free DMEM medium was added to each well which was then incubated for 6 hours at 37° C. under 5% $CO_2$, followed by replacement with 1 ml of 10% FBS-containing DMEM medium. After 12 hours of incubation, each of Fc-TPP11, Ctx and Ctx-TPP11 was diluted in 1 ml of 10% FBS-containing medium at a concentration of 2 µM, and the cells were incubated with the dilution for 24 hours at 37° C. under 5% $CO_2$. After incubation, the cells were washed with cold PBS, and lysis buffer (10 mM Tris-HCl pH 7.4, 100 mM NaCl, 1% SDS, 1 mM EDTA, Inhibitor cocktail(sigma)) was added thereto to obtain cell lysate. Next, Western blot analysis was performed in the same manner as described in Example 1.

As a result, the $Ctx^R$ SW1990 cells expressing no NRP1 had the same Ctx resistance mechanism as BxPC-3 and PANC-1, but the effects of Fc-TPP11 and Ctx-TPP11 did not appear in the cells. In addition, it was shown that the cell growth inhibitory effect of Ctx-TPP11 was because of inhibition of the expression of the Ctx resistance marker integrin β1 identified in Example 1 and inhibition of the phosphorylation of FAK, Src and Akt which are signaling markers downstream of integrin β1. It was shown that when the expression of integrin β1 was inhibited, the phosphorylation of FAK, Src and Akt, which are resistance markers, was inhibited. This suggests that integrin β1 is a molecule upstream of the phosphorylation pathways of FAK, Src and Akt. However, Ctx-TPP11 did not reduce the whole cell expression of integrin β1 itself.

Example 7: Evaluation of Cell Proliferation Inhibitory Effect of Ctx-TPP11 in $Ctx^R$ Colorectal Cancer Cell Lines The mechanism of resistance of most colorectal cancers to Ctx includes KRas and BRaf mutations, unlike pancreatic cancer. In order to confirm whether Ctx-TPP11 also overcomes resistance in other resistance mechanisms, the cell proliferation inhibitory abilities of Fc-TPP11, Ctx and Ctx-TPP11 were evaluated.

FIG. 6 shows the results of an MTT assay performed to examine the cell proliferation inhibitory abilities of Fc-TPP11, Ctx and Ctx-TPP11 in KRas wild-type and BRaf wild-type $Ctx^S$ colorectal cancer cell lines and colorectal cancer lines having resistance to Ctx due to KRas and BRaf mutations.

Specifically, cells were prepared in the same manner as described in Example 2. Then, each of Fc-TPP11, Ctx and Ctx-TPP11 was diluted in 1 ml of 10% FBS-containing medium at a concentration of 0.2 μM or 1 μM, and the cells were incubated with the dilution for 72 hours under 5% $CO_2$ at 37° C., after which an MTT assay was performed. As a result, treatment with Ctx-TPP11 and a combination of Ctx and Fc-TPP11 did not overcome the resistance of the colorectal cancer cell lines having the resistance mechanism caused by KRas and BRaf mutations.

Example 8: Evaluation of Mechanism of the Down-Regulation of Active Integrin β1 by NRP1 Targeting Ctx-TPP11 inhibited the phosphorylation of the Ctx resistance markers (FAK, Src and Akt) by NRP1 targeting, but did not reduce the whole expression level of overexpressed integrin β1. Integrin β1 is classified into active integrin pi in an extended form which can send a signal, and inactive integrin β1 in a bent form which cannot send a signal. Thus, in order to examine whether Ctx-TPP11 down-regulates signaling from integrin β1 by actually reducing the expression of active integrin β1 which can send a signal, the endocytosis of active integrin β1 was analyzed after treatment with Ctx-TPP11.

FIGS. 7a and 7b show the results of confocal microscopic observation performed to examine the endocytosis of NRP1, active integrin β1 and inactive integrin β1 in $Ctx^R$ BxPC-3 and PANC-1 after treatment with Fc-TPP11, Ctx and Ctx-TPP11.

Specifically, a coverslip was added to a 24-well plate, and each of BxPC-3 or PANC-1 cell lines in 0.5 ml of 10% FBS-containing medium was added to each well of the plate at a density of 2.5×10⁴ cells per well and cultured for 12 hours under 5% $CO_2$ at 37° C. When the cells were stabilized, the cells were serum-deprived with serum-free medium for 4 hours in order to eliminate the effect of serum.

Next, the cells were treated with 2 μM of each of Fc-TPP11, Ctx, Ctx-TPP11 (diluted in 0.5 ml of serum-free medium) for 1 hour for 37° C., and then washed three times with cold PBS. Next, the cells were fixed with 4% paraformaldehyde at 25° C. for 10 minutes. Next, the cells were washed with PBS and incubated with a PBS buffer containing 0.1% saponin, 0.1% sodium azide and 1% BSA at 25° C. for 10 minutes, thereby forming holes in the cell membrane. Next, the cells were washed with PBS, and then incubated with a PBS buffer containing 2% BSA at 25° C. for 1 hour in order to inhibit non-specific binding. Next, the cells were incubated with primary antibodies, which recognize NRP1, active integrin β1 (antibody clone name: HUTS-21, BD Bioscience) and inactive integrin β1 (antibody clone name: mAb13, BD Bioscience), respectively, at 25° C. for 1 hour and 30 minutes. The cells were incubated with TRITC (red fluorescence) or FITC (green fluorescence)-conjugated secondary antibodies, which recognize the primary antibodies, respectively, at 25° C. for 1 hour, and the nucleus was stained (blue fluorescence) with Hoechst 33342, followed by confocal microscopic observation. NRP1 overlapped only with active integrin β1, indicating that NRP1 did bind specifically to active integrin β1.

FIGS. 8 and 9 shows the results of FACS analysis performed to analyze the endocytosis of NRP1, EGFR, active integrin β1 and inactive integrin β1 in $Ctx^R$ BxPC-3 and PANC-1 after treatment with Fc-TPP11, Ctx and Ctx-TPP11.

Specifically, cells were prepared in the same manner as described in Example 1. When the cells were stabilized, the cells were serum-deprived with serum-free medium for 4 hours in order to eliminate the effect of serum. Then, the cells were treated with 2 μM of each of Fc-TPP11, Ctx and Ctx-TPP11 (diluted in 1 ml of serum-free medium) at varying time points (0, 5, 15, 30 and 60 min) at 37° C., and then washed with cold PBS. BxPC-3 and PANC-1 cell lines were prepared at a density of 2×10⁵ cells per sample. The cells were incubated with primary antibodies, which recognize NRP1, active integrin β1 and inactive integrin β1, respectively, at 4° C. for 1 hour. Then, the cells were incubated with FITC-conjugated secondary antibodies, which recognize the primary antibodies, respectively, at 4° C. for 30 minutes, after which the cells were washed with cold PBS, and then analyzed by the flow cytometer FACS Calibur (BD Bioscience). After analysis, a histogram graph for each sample was obtained. Based on the mean fluorescence intensity of the histogram, the amounts of receptors remaining on the cell surface after the endocytosis of NRP1, EGFR, active integrin β1 and inactive integrin β1 after treatment with Fc-TPP11, Ctx and Ctx-TPP11 were quantitatively measured, and the results are shown in FIGS. 8b and 9b.

As a result, Fc-TPP11 and Ctx-TPP11, which bind to NRP1, increased the endocytosis of NRP1, and also increased the endocytosis of active integrin β1 bound to NRP1. In addition, Ctx and Ctx-TPP11 increased the endocytosis of EGFR. This suggests that Ctx-TPP11 binds to NRP1 and selectively reduces the cell surface expression levels of NRP1 and active integrin β1.

Example 9: Evaluation of the Inhibitory Activity of Ctx-TPP11 Against Cell Adhesion of Active Integrin β1

Active integrin β1 expressed on the cell surface plays an important role in the binding of the cells to extracellular matrix (ECM). In particular, cells have the highest binding affinity for FN among extracellular matrix proteins. Thus, in order to examine whether Ctx-TPP11 reduces the adhesion of cells to FN by reducing the expression of active integrin β1, analysis was performed.

FIG. 10a shows the results of optical microscopic observation following a cell adhesion assay performed to examine the adhesion of cells to FN in $Ctx^R$ BxPC-3 and PANC-1 after treatment with Fc-TPP11, Ctx and Ctx-TPP11.

Specifically, FN (Sigma), diluted in 0.5 ml of PBS at a concentration of 10 μg/ml, was coated on a 12-well uncoated plate at 37° C. for 30 minutes. BxPC-3 and PANC-1 were pretreated with 100 nM of each of Fc-TPP11, Ctx and Ctx-TPP11 at 37° C. for 30 minutes, and $3 \times 10^5$ pretreated BxPC-3 cells and $1 \times 10^5$ pretreated PANC-1 cells were added to the FN-coated plate. The BxPC-3 cells were incubated for 1 hour at 37° C., and the PANC-1 cells were incubated for 6 hours at 37° C., followed by washing of the cells with PBS. After washing, the cells were fixed with 4% paraformaldehyde at 25° C. for 10 minutes, and washed with PBS, and cells attached to FN were stained with 0.5% (w/v) crystal violet (diluted in 20% ethanol) at 25° C. for 15 minutes. The stained attached cells were analyzed with an optical microscope. Each well was imaged 10 times, and the number of the attached cells was counted. FIG. 10b shows the quantitatively comparing results. Fc-TPP11 and Ctx-TPP11 reduced the adhesion of $Ctx^R$ cells to FN, unlike Ctx. This suggests that Fc-TPP11 and Ctx-TPP11 reduce the binding affinity of active integrin β1 for FN by reducing the expression level of active integrin β1 on the cell surface.

Example 10: Evaluation of In Vivo Tumor Growth Inhibitory Activity of Ctx-TPP11

In Example 5, the in vitro cell growth inhibitory activity of Ctx-TPP11 against $Ctx^R$ pancreatic cancer cell lines was confirmed. Whether the same effect of Ctx-TPP11 also appears in vivo was examined.

FIGS. 11 and 12 show the results of measuring the in vivo tumor growth inhibitory activity of Ctx-TPP11 in mice.

Specifically, BxPC-3 cells ($5 \times 10^6$ cells/mouse), PANC-1 ($1 \times 10^7$ cells/mouse) or AsPC-1 ($5 \times 10^6$ cells/mouse) cells in a 1:1 mixture of 150 μl of PBS and 150 μl of Matrigel (BD Biosciences) were transplanted subcutaneously into 3-week-old female BALB/c nude mice (NARA Biotech, Korea). Mice with tumors having similar sizes (mean volume: 100-120 mm³) were randomly grouped, and each antibody (Ctx, Ctx-TPP11, and Fc-TPP11 and Ctx co-adminstered) was injected intravenously into the tail vein of each mouse. The tumor size was measured at least once, and the tumor volume (V) was calculated using the following equation: V=volume×width²/2.

As shown in FIGS. 11a and 11b, administration of Ctx-TPP11 or a combination of Fc-TPP11 and Ctx inhibited the tumor growth of $Ctx^R$ BxPC-3 and PANC-1, compared to the control PBS. However, the group administered with Ctx showed resistance. In FIGS. 12a and 12b, it was shown that the tumor growth inhibitory activity of Ctx against $Ctx^S$ AsPC-1 was similar to that of Ctx-TPP11. In addition, in FIGS. 11c and 12c, it was shown that administration of Ctx, Ctx-TPP11 and a combination of Fc-TPP11 and Ctx caused little or no change in the weight of the mice, compared to PBS, indicating that they had no toxicity.

FIG. 13 shows the results of immunohistochemistry (IHC) that compare the levels of growth markers and apoptotic markers in the tumor tissues against which the tumor inhibitory activity of was confirmed in FIGS. 11 and 12.

Specifically, 5 hours after the last administration of the antibody in FIGS. 11 and 12, tumor tissue was dissected. The dissected tumor tissue was fixed with 4% paraformaldehyde at 4° C. for 24 hours, and kept in 30% sucrose buffer at 4° C. for 24 hours. Next, the tissue was sectioned to a thickness of 20 μm according to a frozen section method, and the tumor section was stained with Ki-67 antibody (Abcam) and the growth marker Ki-67 as TRITC-conjugated secondary antibody, which recognizes the Ki-67 antibody, at 25° C. for 1 hour. In addition, to examine apoptosis, the tumor tissue was stained with DeadEnd™ Colorimetric TUNEL System (Promega), and the nucleus was stained (blue fluorescence) with Hoechst 33342, followed by confocal microscopic observation. In a tissue treated with Ctx-TPP11 showing inhibition on tumor growth, a decreased amount of the growth marker and an increased amount of the apoptotic marker were observed.

FIG. 14 shows the results of Western blot analysis on dissected tumor tissues against which tumor inhibitory activity was confirmed in FIG. 11.

Specifically, 5 hours after the last administration of the antibody in FIGS. 11 and 12, tumor tissue was dissected. The dissected tumor tissue was homogenized with the cell lysis buffer used in the Example, followed by Western blot analysis. As shown in FIG. 14, it was observed that in the $Ctx^R$ tumor tissue, Ctx-TPP11 and a combination of Ctx and Fc-TPP11 inhibited the phosphorylation of FAK, Src and Akt, which are Ctx resistance markers, in the same manner as the signal inhibitory effect in vitro.

Example 11: Analysis of Cell Surface Expression Levels of EGFR, NRP1 and Integrin β1 in Lung Cancer Cell Lines As shown in Example 1, in pancreatic cancer, the cell surface and whole cell expression levels of integrin β1 were higher in $Ctx^R$ pancreatic cancer cell lines than in $Ctx^S$ pancreatic cancer cell lines. In order to examine whether the mechanism of resistance of lung cancer to Ctx is also correlated with the expression level of integrin β1, the cell surface expression levels of EGFR, NRP1 and integrin β1 in lung cancer cell lines were analyzed.

FIG. 15a shows the results of FACS analysis performed to analyze the cell surface expression levels of EGFR, NRP1 and integrin β1 in $Ctx^S$ (Calu-3, H1975) and $Ctx^R$ (H1299, A549, Calu-1, H358, H441, H2009, HCC44, HCC2108, SK-LU-1, H460, H522) lung cancer cell lines.

Specifically, lung cancer cell lines were prepared in the same manner as described in Example 1. The cells were washed with PBS, and then incubated with an antibody (R&D System), which recognizes NRP1, and FITC-conjugated antibodies(e-Bioscience) which recognize EGFR and integrin β1, respectively, at 4° C. for 1 hour. Additionally, the cells having the NRP1 antibody bound thereto were stained with FITC-conjugated antibody, washed with PBS, and then analyzed with the flow cytometer FACS Calibur (BD Bioscience).

FIG. 15b is a graph quantitatively showing the mean fluorescence intensity of the histogram shown in FIG. 15a.

As a result, unlike the case of pancreatic cancer, resistance to Ctx and the cell surface expression level of integrin β1 showed no particular correlation in the lung cancer cell lines.

Example 12: Examination of the Effects of Inhibition of Expression of Various Cell Surface Receptors and Inhibition of Phosphorylation of Akt and Src on $Ctx^R$ in Lung Cancer As described in Example 11, unlike the case of pancreatic cancer, in lung cancer, the expression level of integrin β1 showed no particular correlation with resistance to Ctx. Thus, in order to examine which receptors on the cell surface are associated with resistance to Ctx, the effects of siRNA against receptors (with which NRP1 acts as co-receptor) among various cell surface receptors were examined.

FIG. 16a is a graph showing the results of analyzing cell viability after Ctx treatment in $Ctx^R$ lung cancer cell lines (A549 and HCC44; NRP1-expressing $Ctx^R$ cell lines) treated with each of control siRNA, NRP1 siRNA, integrin β1 siRNA, integrin β3 siRNA, cMet siRNA, VEGFR1 siRNA, and TGFβR2 siRNA.

Specifically, $2\times10^5$ A549 or HCC44 cells were cultured in each well of 6-well plates, and then subjected to transient transfection with siRNA. For transient transfection, 100 nM of each of a control siRNA having no target and an siRNA targeting each of NRP1, integrin β1, integrin β3, cMet, VEGFR1 and TGFβ2 was incubated with 500 μl of Opti-MEM media (Gibco) and 3.5 μl of RNAiMax (Invitrogen, USA) in a tube at room temperature for 15 minutes, and then added to each well. In addition, 500 μl of antibiotic-free DMEM medium was added to each well which was then incubated for 6 hours at 37° C. under 5% $CO_2$, followed by replacement with 2 ml of DMEM medium containing 10% FBS and 1% antibiotic. After 24 hours of incubation, $5\times10^3$ cells were added to each well of 96-well plates and incubated for 12 hours. Then, Ctx was diluted in 10% FBS-containing medium at a concentration of 2 μM, and the cells were incubated with the dilution for 48 hours, after which cell viability was analyzed by a WST-1 assay.

FIG. 16b shows the results of Western blot analysis performed on the cell lysate, obtained after transient transfection in FIG. 16a, in order to confirm that the siRNAs specifically inhibited the expression of their target proteins.

As a result, it could be seen that inhibition of NRP1 expression and integrin β3 expression in the two lung cancer cell lines tested overcame resistance to Ctx.

Furthermore, in order to examine which downstream signaling factors in addition to expression of NRP1 and integrin β3 are associated with resistance to Ctx, the effects of inhibitors of PI3K-Akt, Src and Raf were evaluated.

FIG. 17 shows the results of analyzing cell viability in $Ctx^R$ lung cancer cell lines after treatment with Ctx in combination with each of a PI3K-Akt inhibitor (LY294002), an Src inhibitor (SU6656) and an Raf inhibitor (Sorafenib).

Specifically, each of A549 and HCC44 cell lines was added to a 96-well plate at a density of $5\times10^3$ cells per well and cultured in 10% FBS-containing medium for 12 hours. Then, 50, 20 and 10 μM of LY294002, 5, 2 and 1 μM of SU6656, and 5, 2 and 1 μM of sorafenib were diluted together with 2 μM of Ctx, and the cells were incubated with each of the dilutions for 48 hours, after which cell viability was analyzed by WST-1 assay.

As a result, it could be seen that inhibition of NRP1 expression and integrin β3 in the lung cancer cell lines (HCC44 and A549) or inhibition of the phosphorylation of Akt and Src could overcome resistance to Ctx. However, inhibition of expression of integrin β1, cMet, VEGFR1 and TGFβ2 or inhibition of phosphorylation of Raf could not overcome resistance to Ctx.

Table 4 below summarizes the results of analyzing the characteristics of the lung cancer cell lines used in the present invention.

TABLE 4

| Cell lines | Mutational state | | | Responsiveness to Cetuximab |
|---|---|---|---|---|
| | EGFR | RAS | BRAF | |
| Calu-3 | WT | WT | WT | Sensitive |
| H1975 | L858R, T790M | WT | WT | Sensitive |
| H522 | WT | WT | WT | Resistant |
| H1299 | WT | NRAS Q61K | WT | Resistant |
| A549 | WT | KRAS G12S | WT | Resistant |
| Calu-1 | WT | KRAS G12C | WT | Resistant |
| H358 | WT | KRAS G12C | WT | Resistant |
| H441 | WT | KRAS G12V | WT | Resistant |
| H2009 | WT | KRAS G12A | WT | Resistant |
| HCC44 | WT | KRAS G12C | WT | Resistant |
| HCC2108 | WT | KRAS Q61H | WT | Resistant |
| SK-LU-1 | WT | KRAS G12D | WT | Resistant |
| H460 | WT | KRAS Q61H | WT | Resistant |

As can be seen in FIG. 15a and Table 4 above, in all the cell lines having the RAS mutation, not the EGFR or BRAF mutation, except the H522 cell line showing resistance to Ctx due to non-expression of EGFR, resistance to Ctx was observed. This fact suggests that, unlike the case of pancreatic cancer, in lung cancer cell lines, resistance to Ctx is closely associated with NRP1, integrin β3 and the KRAS mutation.

Example 13: Evaluation of Cell Proliferation Inhibitory Activity of Ctx-TPP11 in $Ctx^R$ Lung Cancer Cell Lines In order to examine whether Ctx-TPP11 overcomes resistance to Ctx even lung cancer resistant to Ctx, like the results obtained for pancreatic cancer, the cell proliferation inhibitory activities of Ctx and Ctx-TPP11 in $Ctx^S$ lung cancer cell lines and $Ctx^R$ lung cancer cell lines were evaluated.

FIG. 18 shows the results of a cell growth assay performed on a total of 13 lung cancer cell lines in order to examine whether Ctx-TPP11 can inhibit the proliferation of $Ctx^R$ lung cancer cell lines that express NRP1.

FIGS. 18a and 18b shows the results of a WST-1 assay performed to measure cell viability in NRP1-expressing $Ctx^S$ (Calu-3, H1975) and $Ctx^R$ (H1299, A549, Calu-1, H358, H441, H2009, HCC44, SK-LU-1) lung cancer cell lines and non-NRP1-expressing $Ctx^R$ (HCC2108, H460, H522) lung cancer cell lines after treatment with various concentrations of Ctx and Ctx-TPP11.

Specifically, lung cancer cells were added to 96-well plates at a density of $5\times10^3$ cells per well and cultured in 10% FBS-containing medium for 12 hours. Then, the cells were incubated with various concentrations (0, 1, 2, and 4 μM) of Ctx or Ctx-TPP11 for 48 hours, after which 10 μl of Cyto-X reagent (LPS Solution) was added to each well, followed by incubation at 37° C. for 1 to 2 hours. The absorbance at 450 nm was measured using a microplate reader (Molecular Devices). In the $Ctx^S$ (Calu-3, H1975) lung cancer cell lines, Ctx and Ctx-TPP11 showed the same inhibitory activity against cell growth, and in eight $Ctx^R$ (H1299, A549, Calu-1, H358, H441, H2009, HCC44, SK-LU-1) lung cancer cell lines, only Ctx-TPP11 showed cell growth inhibitory activity, unlike Ctx. However, in three $Ctx^R$ lung cancer cell lines (HCC2108, H460, and H522) expressing no NRP1, Ctx-TPP11 showed no activity. This suggests that Ctx-TPP11 is specifically effect against its target NRP1.

FIG. 18c shows the results of evaluating the effect of NRP1 siRNA on the cell proliferation inhibitory activity of Ctx-TPP11 confirmed in the $Ctx^R$ lung cancer cell lines.

Specifically, cells were prepared in the same manner as described in FIG. 17a. The cells were subjected to transient transfection, and then added to a 96-well plate at a density of 5×10³ cells per well and cultured for 12 hours. Then, each of Ctx and Ctx-TPP11 was diluted in 10% FBS-containing medium at a concentration of 2 μM, and the cells were incubated with each of the dilutions for 48 hours, after which cell viability was analyzed by WST-1 assay.

As a result, it was shown that when expression of NRP1 was inhibited by NRP1 siRNA, the cell growth inhibitory activity of Ctx-TPP11 disappeared. This suggests that Ctx-TPP11 exhibits a specific effect against its target NRP1, like the results shown in FIG. 18b.

Example 14: Examination of Correlation Between NRP1, Integrin β3 and KRAS in Ctx$^R$ Lung Cancer Cell Lines Examples 11 and 12 above indicated that, in the lung cancer cell lines, resistance to Ctx was closely correlated with NRP1, integrin β3 and KRAS mutation, and in these Ctx$^R$ lung cancer cell lines, Ctx-TPP11 showed a specific effect against NRP1. Thus, in order to examine why Ctx-TPP11 can overcome resistance to Ctx in lung cancer cell lines, an immunoprecipitation assay was performed to confirm how NRP1 interacts with integrin β3 and KRAS.

FIG. 19a shows the results of an immunoprecipitation assay performed on Ctx$^R$ lung cancer cell lines (HCC44, and A549) using NRP1 antibody.

Specifically, each of lung cancer cell lines (HCC44 and A549; cell lines expressing NRP1 and integrin β3) was added to each well of a 100-mm³ plate at a density of 2×10⁶ cells and cultured in 10% FBS-containing medium for 12 hours. To obtain cell lysate, the cells were incubated with lysis buffer (50 mM Tris-HCl pH 7.4, 150 mM NaCl, 1% NP-40, 0.5% SDC, 0.1% SDS, 100× Protease inhibitor) at 4° C. for 30 minutes, and the cell debris was removed by precipitation. Next, the cell lysate was quantified using a BCA protein assay kit (Pierce), and then 0.5 mg of the cell lysate was incubated with 5 μg of anti-NRP1 antibody (Abacm) at 4° C. for 12 hours. Thereafter, Protein A/G agarose was added thereto, followed by incubation at 4° C. for 2 hours, after which the antibody was precipitated. Next, using anti-NRP1 antibody, anti-EGFR antibody, anti-integrin β3 antibody, anti-integrin β1 antibody, and anti-KRAS antibody, Western blot analysis was performed. As a result, it was shown that when NRP1 in HCC44 and A549 was immunoprecipitated, EGFR, integrin β3 and KRAS were observed together. This suggests that, in the Ctx$^R$ lung cancer cell lines (HCC44, and A549), NRP1 interacted with EGFR, integrin β3 and KRAS. However, the interaction of integrin β1 with NRP1 was observed in HCC44, but not observed in A549.

FIG. 19b shows the results of an immunoprecipitation assay performed using NRP1 antibody in A549 treated with control siRNA and in A549 treated with integrin β3 siRNA in order to examine whether the interaction between NRP1 and KRAS is induced by integrin β3.

Specifically, the A549 cell line was added to a 100 mm³ plate at a density of 1×10⁶ cells per well and cultured in 10% FBS-containing medium for 12 hours, after which it was treated with each of control siRNA and integrin β3 siRNA in the same manner as described in Example 12. Next, in the same manner as the method of FIG. 19a, a cell lysate was prepared and subjected to an immunoprecipitation assay. As a result, in A549 expressing integrin β3 due to treatment with control siRNA, EGFR, integrin β3 and KRAS were all observed together with NRP1. However, in A549 in which expression of integrin β3 was inhibited by treatment with integrin β3 siRNA, EGFR and integrin β3 were observed together with NRP1, but KRAS was not observed. This suggests that NRP1 and KRAS do not interact directly with each other, and NRP1 and KRAS form a complex through integrin β3.

Example 15: Evaluation of Mechanism that Reduces Cell Surface Expression Level of Integrin β3 by NRP1 Targeting As described in Example 8 above, it was confirmed that, in pancreatic cancer, Ctx-TPP11 reduced the cell surface expression level of active integrin β1 by NRP1 targeting, thereby down-regulating signaling from integrin β1. In lung cancer, it was confirmed that NRP1 interacted with integrin β3. Thus, whether the cell surface expression level of integrin β3 can be reduced by NRP1 targeting was examined.

FIG. 20 shows the results of FACS analysis performed to analyze the endocytosis of NRP1 and integrin β3 in Ctx$^R$ HCC44 and A549 after treatment with Fc-TPP11, Ctx and Ctx-TPP11.

Specifically, cells were prepared in the same manner as described in Example 8. When the cells were stabilized, the cells were serum-deprived with serum-free medium for 4 hours in order to eliminate the effect of serum. Then, 2 μM of each of Fc-TPP11, Ctx and Ctx-TPP11 was diluted in 1 ml of serum-free medium, and the cells were treated with the dilution for 15 minutes at 37° C., and then washed with cold PBS. HCC44 and A549 cell lines were prepared at a density of 1×10⁵ cells per sample. The cells were incubated with primary antibodies, which recognize NRP1 and integrin β3, respectively, at 4° C. for 1 hour. Then, the cells were incubated with FITC-conjugated secondary antibodies, which recognize the primary antibodies, respectively, at 4° C. for 30 minutes. Then, the cells were washed with PBS and analyzed using the flow cytometer FACS Calibur (BD Bioscience). After analysis, a histogram for each sample was obtained, and based on the mean fluorescence intensity of the histogram, the amounts of receptors on the cell surface after the endocytosis of NRP1 and integrin β3 by treatment with Fc-TPP11, Ctx or Ctx-TPP11 were measured. The results are quantitatively shown in FIG. 20b.

As a result, it was shown that Fc-TPP11 and Ctx-TPP11, which did bind to NRP1, increased the endocytosis of NRP1 and also increased the endocytosis of integrin β3 bound to NRP1. This suggests that Ctx-TPP11 binds NRP1 and selectively reduces the cell surface expression levels of NRP1 and integrin β3.

Example 16: Expression and Purification of Pnm-TPP11

Examples 1 to 13 described cell lines resistant to Ctx among EGFR-targeting antibodies. Additionally, in order to examine whether Pnm-TPP11, obtained by fusing TPP11 to Panitumumab (Pnm) among EGFR-targeting antibodies, can inhibit the proliferation of Pnm$^R$ lung cancer cells, Pnm-TPP11 was expressed and purified.

FIG. 21a is a schematic view of Pnm-TPP11 in which a TPP11 peptide is fused to the C-terminus of the heavy chain of Pnm by a $(G_4S)_3$ linker consisting of 15 residues.

Specifically, using a reverse primer for the C-terminus of the heavy chain of Pnm (amino acid (AA) sequence of SEQ ID NO: 12; and DNA sequence of SEQ ID NO: 13) and a (G₄S)₃ linker and a forward primer for TPP11, polymerase chain reaction was performed, and a DNA fragment composed sequentially of a signal peptide, a Pnm heavy-chain, a (G₄S)₃ linker, TPP11 and termination codon were obtained. Next, using 1% agarose gel and electrophoresis, DNA was recovered, and using NotI and BamHI restriction enzymes, a cohesive end was generated. Thereafter, cloning into a pcDNA3.4 vector by T4 ligase was performed, thereby constructing a vector capable of expressing a Pnm-TPP11 heavy chain (AA sequence of SEQ ID NO: 10, and DNA sequence of SEQ ID NO: 11) in animal cells. As a light chain-encoding DNA (AA sequence of SEQ ID NO: 14, and DNA sequence of SEQ ID NO: 15), a vector expressing a wild-type Pnm light chain was used.

TABLE 5

| Constitution | Sequences | SEQ ID NO: |
|---|---|---|
| Heavy chain amino acid sequence of Pnm-TPP11 | QVQLQESGPGLVKPSETLSLTCTVSGGSVSSG DYYWTWIRQSPGKGLEWIGHIYYSGNTNYNPS LKSRLTISIDTSKTQFSLKLSSVTAADTAIYY CVRDRVTGAFDIWGQGTMVTVSSASTKGPSVF PLAPCSRSTSESTAALGCLVKDYFPEPVTVSW NSGALTSGVHTFPAVLQSSGLYSLSSVVTVPS SNFGTQTYTCNVDHKPSNTKVDKTVERKCCVE CPPCPAPPVAGPSVFLFPPKPKDTLMISRTPE VTCVVVDVSHEDPEVQFNWYVDGVEVHNAKTK PREEQFNSTFRVVSVLTVVHQDWLNGKEYKCK VSNKGLPAPIEKTISKTKGQPREPQVYTLPPS REEMTKNQVSLTCLVKGFYPSDIAVEWESNGQ PENNYKTTPPMLDSDGSFFLYSKLTVDKSRWQ QGNVFSCSVMHEALHNHYTQKSLSLSPGKGGG GSGGGGSGGGGSHTPGNSKPTRTPRR | SEQ ID NO: 10 |
| Heavy chain DNA sequence of Pnm-TPP11 | CAGGTGCAGCTGCAGGAGTCCGGCCCCGGCCT GGTGAAGCCCTCCGAGACCCTGTCCCTGACCT GCACCGTGTCCGGCGGCTCCGTGTCCTCCGGC GACTACTACTGGACCTGGATTCGGCAGTCCCC CGGCAAGGGCCTGGAGTGGATCGGCCACATCT ACTACTCCGGCAACACCAACTACAACCCCTCC CTGAAGTCCCGGCTGACCATCTCCATCGACAC CTCCAAGACCCAGTTCTCCCTGAAGCTGTCCT CCGTGACCGCCGCCGACACCGCCATCTACTAC TGCGTGCGGGACCGGGTGACCGGCGCCTTCGA CATCTGGGGCCAGGGCACCATGGTGACCGTGT CCTCCGCCTCCACCAAGGGCCCATCGGTCTTC CCCCTGGCGCCCTGCTCCAGGAGCACCTCCGA GAGCACAGCGGCCCTGGGCTGCCTGGTCAAGG ACTACTTCCCCGAACCGGTGACGGTGTCGTGG AACTCAGGCGCTCTGACCAGCGGCGTGCACAC CTTCCCAGCTGTCCTACAGTCCTCAGGACTCT ACTCCCTCAGCAGCGTGGTGACCGTGCCCTCC AGCAACTTCGGCACCCAGACCTACACCTGCAA CGTAGATCACAAGCCCAGCAACACCAAGGTGG ACAAGACAGTTGAGCGCAAATGTTGTGTCGAG TGCCCACCGTGCCCAGCACCACCTGTGGCAGG ACCGTCAGTCTTCCTCTTCCCCCCAAAACCCA AGGACACCCTCATGATCTCCCGGACCCCTGAG GTCACGTGCGTGGTGGTGGACGTGAGCCACGA AGACCCCGAGGTCCAGTTCAACTGGTACGTGG ACGGCGTGGAGGTGCATAATGCCAAGACAAAG CCACGGGAGGAGCAGTTCAACAGCACGTTCCG TGTGGTCAGCGTCCTCACCGTTGTGCACCAGG ACTGGCTGAACGGCAAGGAGTACAAGTGCAAG GTCTCCAACAAAGGCCTCCCAGCCCCCATCGA GAAAACCATCTCCAAAACCAAAGGGCAGCCCC GAGAACCACAGGTGTACACCCTGCCCCCATCC CGGGAGGAGATGACCAAGAACCAGGTCAGCCT GACCTGCCTGGTCAAAGGCTTCTACCCCAGCG ACATCGCCGTGGAGTGGGAGAGCAATGGGCAG CCGGAGAACAACTACAAGACCACACCTCCCAT GCTGGACTCCGACGGCTCCTTCTTCCTCTACA GCAAGCTCACCGTGGACAAGAGCAGGTGGCAG CAGGGGAACGTCTTCTCATGCTCCGTGATGCA TGAGGCTCTGCACAACCACTACACGCAGAAGA GCCTCTCCCTGTCCCCGGGTAAAGGTGGAGGA GGATCTGGAGGAGGAGGAAGTGGAGGTGGAGG ATCACATACTCCTGGAAATAGCAAACCAACAC GCACACCAAGGCGT | SEQ ID NO: 11 |
| Heavy chain amino acid sequence of Pnm | QVQLQESGPGLVKPSETLSLTCTVSGGSVSSG DYYWTWIRQSPGKGLEWIGHIYYSGNTNYNPS LKSRLTISIDTSKTQFSLKLSSVTAADTAIYY CVRDRVTGAFDIWGQGTMVTVSSASTKGPSVF PLAPCSRSTSESTAALGCLVKDYFPEPVTVSW NSGALTSGVHTFPAVLQSSGLYSLSSVVTVPS | SEQ ID NO: 12 |

TABLE 5-continued

| Constitution | Sequences | SEQ ID NO: |
|---|---|---|
| | SNFGTQTYTCNVDHKPSNTKVDKTVERKCCVE CPPCPAPPVAGPSVFLFPPKPKDTLMISRTPE VTCVVVDVSHEDPEVQFNWYVDGVEVHNAKTK PREEQFNSTFRVVSVLTVVHQDWLNGKEYKCK VSNKGLPAPIEKTISKTKGQPREPQVYTLPPS REEMTKNQVSLTCLVKGFYPSDIAVEWESNGQ PENNYKTTPPMLDSDGSFFLYSKLTVDKSRWQ QGNVFSCSVMHEALHNHYTQKSLSLSPGK | |
| Heavy chain DNA sequence of Pnm | CAGGTGCAGCTGCAGGAGTCCGGCCCCGGCCT GGTGAAGCCCTCCGAGACCCTGTCCCTGACCT GCACCGTGTCCGGCGGCTCCGTGTCCTCCGGC GACTACTACTGGACCTGGATTCGGCAGTCCCC CGGCAAGGGCCTGGAGTGGATCGGCCACATCT ACTACTCCGGCAACACCAACTACAACCCCTCC CTGAAGTCCCGGCTGACCATCTCCATCGACAC CTCCAAGACCCAGTTCTCCCTGAAGCTGTCCT CCGTGACCGCCGCCGACACCGCCATCTACTAC TGCGTGCGGGACCGGGTGACCGGCGCCTTCGA CATCTGGGGCCAGGGCACCATGGTGACCGTGT CCTCCGCCTCCACCAAGGGCCCATCGGTCTTC CCCCTGGCGCCCTGCTCCAGGAGCACCTCCGA GAGCACAGCGGCCCTGGGCTGCCTGGTCAAGG ACTACTTCCCCGAACCGGTGACGGTGTCGTGG AACTCAGGCGCTCTGACCAGCGGCGTGCACAC CTTCCCAGCTGTCCTACAGTCCTCAGGACTCT ACTCCCTCAGCAGCGTGGTGACCGTGCCCTCC AGCAACTTCGGCACCCAGACCTACACCTGCAA CGTAGATCACAAGCCCAGCAACACCAAGGTGG ACAAGACAGTTGAGCGCAAATGTTGTGTCGAG TGCCCACCGTGCCCAGCACCACCTGTGGCAGG ACCGTCAGTCTTCCTCTTCCCCCCAAAACCCA AGGACACCCTCATGATCTCCCGGACCCCTGAG GTCACGTGCGTGGTGGTGGACGTGAGCCACGA AGACCCCGAGGTCCAGTTCAACTGGTACGTGG ACGGCGTGGAGGTGCATAATGCCAAGACAAAG CCACGGGAGGAGCAGTTCAACAGCACGTTCCG TGTGGTCAGCGTCCTCACCGTTGTGCACCAGG ACTGGCTGAACGGCAAGGAGTACAAGTGCAAG GTCTCCAACAAAGGCCTCCCAGCCCCCATCGA GAAAACCATCTCCAAAACCAAAGGGCAGCCCC GAGAACCACAGGTGTACACCCTGCCCCCATCC CGGGAGGAGATGACCAAGAACCAGGTCAGCCT GACCTGCCTGGTCAAAGGCTTCTACCCCAGCG ACATCGCCGTGGAGTGGGAGAGCAATGGGCAG CCGGAGAACAACTACAAGACCACACCTCCCAT GCTGGACTCCGACGGCTCCTTCTTCCTCTACA GCAAGCTCACCGTGGACAAGAGCAGGTGGCAG CAGGGGAACGTCTTCTCATGCTCCGTGATGCA TGAGGCTCTGCACAACCACTACACGCAGAAGA GCCTCTCCCTGTCCCCGGGTAAA | SEQ ID NO: 13 |
| Light chain amino acid sequence of Pnm | DIQMTQSPSSLSASVGDRVTITCQASQDISNY LNWYQQKPGKAPKLLIYDASNLETGVPSRFSG SGSGTDFTFTISSLQPEDIATYFCQHFDHLPL AFGGGTKVEIKRTVAAPSVFIFPPSDEQLKSG TASVVCLLNNFYPREAKVQWKVDNALQSGNSQ ESVTEQDSKDSTYSLSSTLTLSKADYEKHKVY ACEVTHQGLSSPVTKSFNRGEC | SEQ ID NO: 14 |
| Light chain DNA sequence of Pnm | GACATCCAGATGACCCAGTCTCCATCCTCCCT GTCTGCATCTGTAGGAGACAGAGTCACCATCA CTTGCCAGGCGAGTCAGGACATCAGCAACTAT TTAAATTGGTATCAGCAGAAACCAGGGAAAGC CCCTAAACTCCTGATCTACGATGCATCCAATT TGGAAACAGGGGTCCCATCAAGGTTCAGTGGA AGTGGATCTGGGACAGATTTTACTTTCACCAT CAGCAGCCTGCAGCCTGAAGATATTGCAACAT ATTTCTGCCAACACTTTGATCATCTCCCGCTC GCTTTCGGCGAGGGACCAAGGTGGAGATCAA ACGTACGGTGGCTGCACCATCTGTCTTCATCT TCCCGCCATCTGATGAGCAGTTGAAATCTGGA ACTGCCTCTGTTGTGTGCCTGCTGAATAACTT CTATCCCAGAGAGGCCAAAGTACAGTGGAAGG TGGATAACGCCCTCCAATCGGGTAACTCCCAG GAGAGTGTCACAGAGCAGGACAGCAAGGACAG CACCTACAGCCTCAGCAGCACCCTGACGCTGA GCAAAGCAGACTACGAGAAACACAAAGTCTAC | SEQ ID NO: 15 |

TABLE 5-continued

| Constitution | Sequences | SEQ ID NO: |
|---|---|---|
| | GCCTGCGAAGTCACCCATCAGGGCCTGAGCTC GCCCGTCACAAAGAGCTTCAACAGGGGAGAGT GT | |

The light-chain and heavy-chain expression vectors were subjected to transient transfection, thereby expressing and purifying protein. In a shaking flask, HEK293-F cells (Invitrogen) suspension-growing in serum-free FreeStyle 293 expression medium (Invitrogen) were transfected with a mixture of a plasmid and polyethylenimine (PEI) (Polyscience). For 200 mL transfection in a shaking flask (Corning), HEK293-F cells were seeded into 100 ml of medium at a density of $2\times10^6$ cells/ml and cultured at 130 rpm under 8% $CO_2$. Heavy-chain and light-chain plasmids suitable for producing each monoclonal antibody were diluted in 10 ml of FreeStyle 293 expression medium (Invitrogen) to 125 μg heavy chain and 125 μg light chain (a total of 250 μg (2.5 μg/ml)), and the dilution was mixed with 10 ml of medium containing 750 μg (7.5 μg/ml) of PEI and was incubated at room temperature for 10 minutes. Next, the incubated mixed medium was added to 100 ml of the above-seeded cells and incubated for 4 hours at 150 rpm under 8% $CO_2$, and then the remaining 100 ml of FreeStyle 293 expression medium was added thereto, followed by incubation for 7 days. With reference to a standard protocol, protein was purified from the collected cell culture supernatant. Antibody was applied to a Protein A Sepharose column (GE healthcare), followed by washing with PBS (pH 7.4). The antibody was eluted with 0.1 M glycine buffer at pH 3.0, and then the sample was immediately neutralized with 1M Tris buffer. The eluted antibody fraction was concentrated by dialysis while replacing buffer with PBS (pH 7.4). The purified protein was quantified using the absorbance at 280 nm and absorption coefficient.

Example 17: Evaluation of Cell Growth Inhibitory Activity of Pnm-TPP11 in $Pnm^R$ Lung Cancer Cell Lines In order to examine whether Pnm-TPP11 can also inhibit the proliferation of NRP1-expressing $Pnm^R$ lung cancer cell lines, like Ctx-TPP11, a cell growth assay was performed using various lung cancer cell lines.

FIGS. 21b and 21c show the results of a WST-1 assay performed to measure cell viability in NRP1-expressing $Pnm^S$ (Calu-3, A549, Calu-1, HCC44) and $Pnm^R$ (H441, SK-LU-1, H1299) lung cancer cell lines and a non-NRP1-expressing $Pnm^R$ lung cancer cell line after treatment with various concentrations of Pnm and Pnm-TPP11.

Specifically, lung cancer cell lines were prepared in the same manner as described in Example 11. When the cells were stabilized, the cells were incubated with various concentrations (0, 1, 2, and 4 μM) of each of Pnm and Pnm-TPP11 for 48 hours. Then, 10 μl of Cyto-X reagent (LPS Solution) was added to each well which was then incubated at 37° C. for 1 to 2 hours, and the absorbance at 450 nm was measured using a microplate reader (Molecular Devices). In the $Pnm^S$ (Calu-3, A549, Calu-1, HCC44) lung cancer cell line, Pnm and Pnm-TPP11 showed the same inhibitory activity against cell growth, and in three $Pnm^R$ (H441, SK-LU-1, H1299) lung cancer cell lines, only Pnm-TPP11 showed cell growth inhibitory activity, unlike Pnm. However, in the non-NRP1-expressing $Pnm^R$ lung cancer cell line H460, Pnm-TPP11 was showed no effect. This suggests that Pnm-TPP11 shows an effect specific against its target NRP1.

INDUSTRIAL APPLICABILITY

According to the present invention, when the peptide that binds specifically to neuropilin-1 (NRP1) is fused to an EGFR-targeting antibody or the NRP1-binding peptide fused Fc combined with an EGFR-targeting antibody, it acts on NRP1 in tumor cells to promote the endocytosis of NRP1/active integrin β1, thereby reducing the cell surface expression level of active integrin β1 and reducing the integrin β1-induced phosphorylation of FAK, Src and Akt. Accordingly, through the composition or combination formulation according to the present invention, the intrinsic resistance of cancer to an EGFR-targeting antibody can be overcome. Thus, the present invention may be used for the development of effective anticancer drugs or anticancer adjuvants.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

A 32 Kb sequence text file named "268824-459902 SEQUENCE-LISTING", saved on Nov. 27, 2021, is herein incorporated by reference.

The invention claimed is:

1. A composition for treatment of cancer consisting comprising one or more neuropilin-1 (NRP1)-specific binding peptide(s) selected from the group consisting of SEQ ID NOS: 1 to 3.

2. The composition of claim 1, wherein the NRP1-specific binding peptide is fused to an EGFR-targeting antibody or fragment thereof.

3. The composition of claim 2, wherein the EGFR-targeting antibody or fragment thereof is selected from the group consisting of cetuximab, panitumumab, zalutumumab, nimotuzumab, and matuzumab.

4. The composition of claim 2, or wherein the cancer treated is pancreatic cancer or lung cancer.

5. The composition of claim 2, wherein the NRP1-specific binding peptide is fused to the C-terminus of the EGFR-targeting antibody or fragment thereof.

6. The composition of claim 5, wherein the NRP1-specific binding peptide fused to the C-terminus of an the EGFR-targeting antibody or fragment thereof further comprises a linker.

7. The composition of claim 6, wherein the linker comprises a sequence of (GGGGS)n (SEQ ID NO: 16), where n is an integer ranging from 1 to 20.

8. The composition of claim 2, wherein the antibody fragment is an Fc, Fab, scFv, $V_H$ or $V_L$, of an EGFR antibody.

9. The composition of claim 8, wherein the NRP1-specific binding peptide is fused to the C-terminus of an antibody Fc fragment.

10. An anticancer drug comprising the composition of claim 8.

11. An anticancer adjuvant comprising the composition of claim 8.

12. A composition for co-administration with a cancer treatment, comprising a neuropilin-1 (NRP1)-binding peptide comprising an amino acid sequence selected from the group consisting of SEQ ID NOS: 1 to 3, wherein the NRP1-binding peptide is fused to an Fc antibody fragment or an EGFR-targeting antibody.

13. The composition of claim 12, wherein the EGFR-targeting antibody is selected from the group consisting of cetuximab, panitumumab, zalutumumab, nimotuzumab, and matuzumab.

14. The composition of claim 13, wherein the cancer is pancreatic cancer or lung cancer.

* * * * *

SEQUENCE LISTING

```
<160> NUMBER OF SEQ ID NOS: 16

<210> SEQ ID NO 1
<211> LENGTH: 14
<212> TYPE: PRT
<213> ORGANISM: Artificial Sequence
<220> FEATURE:
<223> OTHER INFORMATION: NRP1 Peptide (Synthetic)

<400> SEQUENCE: 1
```

-continued

His Thr Pro Gly Asn Ser Lys Pro Thr Arg Thr Pro Arg Arg
1               5                   10

<210> SEQ ID NO 2
<211> LENGTH: 18
<212> TYPE: PRT
<213> ORGANISM: Artificial Sequence
<220> FEATURE:
<223> OTHER INFORMATION: NRP1 Peptide (synthetic)

<400> SEQUENCE: 2

His Thr Pro Gly Asn Ser Asn Gln Phe Val Leu Thr Ser Thr Arg Pro
1               5                   10                  15

Pro Arg

<210> SEQ ID NO 3
<211> LENGTH: 11
<212> TYPE: PRT
<213> ORGANISM: Artificial Sequence
<220> FEATURE:
<223> OTHER INFORMATION: NRP1 Peptide (Synthetic)

<400> SEQUENCE: 3

His Thr Pro Gly Ile Ala Thr Arg Thr Pro Arg
1               5                   10

<210> SEQ ID NO 4
<211> LENGTH: 497
<212> TYPE: PRT
<213> ORGANISM: Artificial Sequence
<220> FEATURE:
<223> OTHER INFORMATION: Cetuximab-TPP11 VH (Synthetic)

<400> SEQUENCE: 4

Met Gly Trp Ser Cys Ile Ile Leu Phe Leu Val Ala Thr Ala Thr Gly
1               5                   10                  15

Val His Ser Gln Val Gln Leu Lys Gln Ser Gly Pro Gly Leu Val Gln
                20                  25                  30

Pro Ser Gln Ser Leu Ser Ile Thr Cys Thr Val Ser Gly Phe Ser Leu
            35                  40                  45

Thr Asn Tyr Gly Val His Trp Val Arg Gln Ser Pro Gly Lys Gly Leu
        50                  55                  60

Glu Trp Leu Gly Val Ile Trp Ser Gly Gly Asn Thr Asp Tyr Asn Thr
65                  70                  75                  80

Pro Phe Thr Ser Arg Leu Ser Ile Asn Lys Asp Asn Ser Lys Ser Gln
                85                  90                  95

Val Phe Phe Lys Met Asn Ser Leu Gln Ser Asn Asp Thr Ala Ile Tyr
            100                 105                 110

Tyr Cys Ala Arg Ala Leu Thr Tyr Tyr Asp Tyr Glu Phe Ala Tyr Trp
        115                 120                 125

Gly Gln Gly Thr Leu Val Thr Val Ser Ala Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys Gly Gly Gly Ser Gly Gly Gly Gly Ser Gly Gly Gly
465                 470                 475                 480

Gly Gly Ser His Thr Pro Gly Asn Ser Lys Pro Thr Arg Thr Pro Arg
                485                 490                 495

Arg

<210> SEQ ID NO 5
<211> LENGTH: 1434
<212> TYPE: DNA
<213> ORGANISM: Artificial Sequence
<220> FEATURE:
<223> OTHER INFORMATION: Cetuximab-TPP11 VH  (Synthetic)

<400> SEQUENCE: 5
caggtgcagc tgaaacagag cggcccgggc ctggtgcagc cgagccagag cctgagcatt      60
acctgcaccg tgagcggctt tagcctgacc aactatggcg tgcattgggt gcgccagagc     120
ccgggcaaag cctggaatg gctgggcgtg atttggagcg gcggcaacac cgattataac      180
accccgttta ccagccgcct gagcattaac aaagataaca gcaaaagcca ggtgtttttt     240
aaaatgaaca gcctgcagag caacgatacc gcgatttatt attgcgcgcg cgcgctgacc     300
tattatgatt atgaatttgc gtattggggc cagggcaccc tggtgaccgt gagcgcggcc     360

```
tccaccaagg gcccatcggt cttccccctg gcaccctcct ccaagagcac ctctgggggc    420
acagcggccc tgggctgcct ggtcaaggac tacttccccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg ccctccagca gcttgggcac ccagacctac    600
atctgcaacg tgaatcacaa gcccagcaac accaaggtgg acaagaaagt tgagcccaaa    660
tcttgtgaca aaactcacac atgcccaccg tgcccagcac ctgaactcct ggggggaccg    720
tcagtcttcc tcttcccccc aaaacccaag gacaccctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaagccctc ccagccccca tcgagaaaac catctccaaa   1020
gccaaagggc agccccgaga accacaggtg tacaccctgc ccccatcccg ggatgagctg   1080
accaagaacc aggtcagcct gacctgcctg gtcaaaggct tctatcccag cgacatcgcc   1140
gtggagtggg agagcaatgg gcagccggag aacaactaca agaccacgcc tcccgtgctg   1200
gactccgacg gctccttctt cctctacagc aagctcaccg tggacaagag caggtggcag   1260
caggggaacg tcttctcatg ctccgtgatg catgaggctc tgcacaacca ctacacgcag   1320
aagagcctct ccctgtcccc gggtaaaggt ggaggaggat ctggaggagg aggaagtgga   1380
ggtggaggat cacatactcc tggaaatagc aaaccaacac gcacaccaag gcgt          1434
```

<210> SEQ ID NO 6
<211> LENGTH: 468
<212> TYPE: PRT
<213> ORGANISM: Artificial Sequence
<220> FEATURE:
<223> OTHER INFORMATION: Cetuximab VH (Synthetic)

<400> SEQUENCE: 6

```
Met Gly Trp Ser Cys Ile Ile Leu Phe Leu Val Ala Thr Ala Thr Gly
1               5                   10                  15

Val His Ser Gln Val Gln Leu Lys Gln Ser Gly Pro Gly Leu Val Gln
            20                  25                  30

Pro Ser Gln Ser Leu Ser Ile Thr Cys Thr Val Ser Gly Phe Ser Leu
        35                  40                  45

Thr Asn Tyr Gly Val His Trp Val Arg Gln Ser Pro Gly Lys Gly Leu
    50                  55                  60

Glu Trp Leu Gly Val Ile Trp Ser Gly Gly Asn Thr Asp Tyr Asn Thr
65                  70                  75                  80

Pro Phe Thr Ser Arg Leu Ser Ile Asn Lys Asp Asn Ser Lys Ser Gln
                85                  90                  95

Val Phe Phe Lys Met Asn Ser Leu Gln Ser Asn Asp Thr Ala Ile Tyr
            100                 105                 110

Tyr Cys Ala Arg Ala Leu Thr Tyr Tyr Asp Tyr Glu Phe Ala Tyr Trp
        115                 120                 125

Gly Gln Gly Thr Leu Val Thr Val Ser Ala Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175
```

Val Ser Trp Asn Ser Gly Ala Leu Thr Ser Gly Val His Thr Phe Pro
            180                 185                 190
Ala Val Leu Gln Ser Ser Gly Leu Tyr Ser Leu Ser Val Val Thr
        195                 200                 205
Val Pro Ser Ser Ser Leu Gly Thr Gln Thr Tyr Ile Cys Asn Val Asn
    210                 215                 220
His Lys Pro Ser Asn Thr Lys Val Asp Lys Lys Val Glu Pro Lys Ser
225                 230                 235                 240
Cys Asp Lys Thr His Thr Cys Pro Pro Cys Pro Ala Pro Glu Leu Leu
                245                 250                 255
Gly Gly Pro Ser Val Phe Leu Phe Pro Pro Lys Pro Lys Asp Thr Leu
            260                 265                 270
Met Ile Ser Arg Thr Pro Glu Val Thr Cys Val Val Val Asp Val Ser
        275                 280                 285
His Glu Asp Pro Glu Val Lys Phe Asn Trp Tyr Val Asp Gly Val Glu
    290                 295                 300
Val His Asn Ala Lys Thr Lys Pro Arg Glu Glu Gln Tyr Asn Ser Thr
305                 310                 315                 320
Tyr Arg Val Val Ser Val Leu Thr Val Leu His Gln Asp Trp Leu Asn
                325                 330                 335
Gly Lys Glu Tyr Lys Cys Lys Val Ser Asn Lys Ala Leu Pro Ala Pro
            340                 345                 350
Ile Glu Lys Thr Ile Ser Lys Ala Lys Gly Gln Pro Arg Glu Pro Gln
        355                 360                 365
Val Tyr Thr Leu Pro Pro Ser Arg Asp Glu Leu Thr Lys Asn Gln Val
    370                 375                 380
Ser Leu Thr Cys Leu Val Lys Gly Phe Tyr Pro Ser Asp Ile Ala Val
385                 390                 395                 400
Glu Trp Glu Ser Asn Gly Gln Pro Glu Asn Asn Tyr Lys Thr Thr Pro
                405                 410                 415
Pro Val Leu Asp Ser Asp Gly Ser Phe Phe Leu Tyr Ser Lys Leu Thr
            420                 425                 430
Val Asp Lys Ser Arg Trp Gln Gln Gly Asn Val Phe Ser Cys Ser Val
        435                 440                 445
Met His Glu Ala Leu His Asn His Tyr Thr Gln Lys Ser Leu Ser Leu
    450                 455                 460
Ser Pro Gly Lys
465

<210> SEQ ID NO 7
<211> LENGTH: 1347
<212> TYPE: DNA
<213> ORGANISM: Artificial Sequence
<220> FEATURE:
<223> OTHER INFORMATION: Cetuximab VH  (Synthetic)

<400> SEQUENCE: 7
caggtgcagc tgaaacagag cggcccgggc ctggtgcagc cgagccagag cctgagcatt     60
acctgcaccg tgagcggctt tagcctgacc aactatggcg tgcattgggt gcgccagagc    120
ccgggcaaag cctggaatg gctgggcgtg atttggagcg gcggcaacac cgattataac    180
accccgttta ccagccgcct gagcattaac aaagataaca gcaaaagcca ggtgttttt    240 aaaatgaaca gcctgcagag caacgatacc gcgatttatt attgcgcgcg cgcgctgacc    300
tattatgatt atgaatttgc gtattggggc cagggcaccc tggtgaccgt gagcgcggcc    360

```
tccaccaagg gcccatcggt cttccccctg gcaccctcct ccaagagcac ctctgggggc    420
acagcggccc tgggctgcct ggtcaaggac tacttccccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg ccctccagca gcttgggcac ccagacctac    600
atctgcaacg tgaatcacaa gcccagcaac accaaggtgg acaagaaagt tgagcccaaa    660
tcttgtgaca aaactcacac atgcccaccg tgcccagcac ctgaactcct ggggggaccg    720
tcagtcttcc tcttccccccc aaaacccaag gacaccctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaagccctc ccagccccca tcgagaaaac catctccaaa   1020
gccaaagggc agccccgaga accacaggtg tacaccctgc ccccatcccg ggatgagctg   1080
accaagaacc aggtcagcct gacctgcctg gtcaaaggct tctatcccag cgacatcgcc   1140
gtggagtggg agagcaatgg gcagccggag aacaactaca agaccacgcc tcccgtgctg   1200
gactccgacg gctccttctt cctctacagc aagctcaccg tggacaagag caggtggcag   1260
caggggaacg tcttctcatg ctccgtgatg catgaggctc tgcacaacca ctacacgcag   1320
aagagcctct ccctgtcccc gggtaaa                                       1347

<210> SEQ ID NO 8
<211> LENGTH: 233
<212> TYPE: PRT
<213> ORGANISM: Artificial Sequence
<220> FEATURE:
<223> OTHER INFORMATION: Cetuximab VL  (Synthetic)

<400> SEQUENCE: 8

Met Gly Trp Ser Cys Ile Ile Leu Phe Leu Val Ala Thr Ala Thr Gly
1               5                   10                  15

Val His Ser Asp Ile Leu Leu Thr Gln Ser Pro Val Ile Leu Ser Val
            20                  25                  30

Ser Pro Gly Glu Arg Val Ser Phe Ser Cys Arg Ala Ser Gln Ser Ile
        35                  40                  45

Gly Thr Asn Ile His Trp Tyr Gln Gln Arg Thr Asn Gly Ser Pro Arg
    50                  55                  60

Leu Leu Ile Lys Tyr Ala Ser Glu Ser Ile Ser Gly Ile Pro Ser Arg
65                  70                  75                  80

Phe Ser Gly Ser Gly Ser Gly Thr Asp Phe Thr Leu Ser Ile Asn Ser
                85                  90                  95

Val Glu Ser Glu Asp Ile Ala Asp Tyr Tyr Cys Gln Gln Asn Asn Asn
            100                 105                 110

Trp Pro Thr Thr Phe Gly Ala Gly Thr Lys Leu Glu Leu Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190
```

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 9
<211> LENGTH: 645
<212> TYPE: DNA
<213> ORGANISM: Artificial Sequence
<220> FEATURE:
<223> OTHER INFORMATION: Cetuximab VL  (Synthetic)

<400> SEQUENCE: 9
gatattctgc tgacccagag cccggtgatt ctgagcgtga gcccgggcga acgcgtgagc     60
tttagctgcc gcgcgagcca gagcattggc accaacattc attggtatca gcagcgcacc    120
aacggcagcc cgcgcctgct gattaaatat gcgagcgaaa gcattagcgg cattccgagc    180
cgctttagcg gcagcggcag cggcaccgat tttaccctga gcattaacag cgtggaaagc    240
gaagatattg cggattatta ttgccagcag aacaacaact ggccgaccac ctttggcgcg    300
ggcaccaaac tggaactgaa acgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttga                   645

<210> SEQ ID NO 10
<211> LENGTH: 474
<212> TYPE: PRT
<213> ORGANISM: Artificial Sequence
<220> FEATURE:
<223> OTHER INFORMATION: Pnm-TPP11 Heavy Chain  (Synthetic)

<400> SEQUENCE: 10

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
            195                 200                 205

Ser Asn Thr Lys Val Asp Lys Thr Val Glu Arg Lys Cys Cys Val Glu
            210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Phe Arg Val Val Ser Val Leu
290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
            325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys Gly Gly Gly
            435                 440                 445

Gly Ser Gly Gly Gly Gly Ser Gly Gly Gly Gly Ser His Thr Pro Gly
450                 455                 460

Asn Ser Lys Pro Thr Arg Thr Pro Arg Arg
465                 470

<210> SEQ ID NO 11
<211> LENGTH: 1422
<212> TYPE: DNA
<213> ORGANISM: Artificial Sequence
<220> FEATURE:
<223> OTHER INFORMATION: Pnm-TPP11 Heavy Chain (Synthetic)

<400> SEQUENCE: 11
caggtgcagc tgcaggagtc cggccccggc ctggtgaagc cctccgagac cctgtccctg      60
acctgcaccg tgtccggcgg ctccgtgtcc tccggcgact actactggac ctggattcgg     120
cagtcccccg gcaagggcct ggagtggatc ggccacatct actactccgg caacaccaac     180

```
tacaacccct ccctgaagtc ccggctgacc atctccatcg acacctccaa gacccagttc      240
tccctgaagc tgtcctccgt gaccgccgcc gacaccgcca tctactactg cgtgcgggac      300
cgggtgaccg gcgccttcga catctggggc cagggcacca tggtgaccgt gtcctccgcc      360
tccaccaagg gcccatcggt cttccccctg gcgccctgct ccaggagcac ctccgagagc      420
acagcggccc tgggctgcct ggtcaaggac tacttccccg aaccggtgac ggtgtcgtgg      480
aactcaggcg ctctgaccag cggcgtgcac accttcccag ctgtcctaca gtcctcagga      540
ctctactccc tcagcagcgt ggtgaccgtg ccctccagca cttcggcacc cagacctac       600 acctgcaacg tagatcacaa gcccagcaac accaaggtgg acaagacagt tgagcgcaaa      660
tgttgtgtcg agtgcccacc gtgcccagca ccacctgtgg caggaccgtc agtcttcctc      720
ttccccccaa acccaaggac accctcatg atctcccgga cccctgaggt cacgtgcgtg        780
gtggtggacg tgagccacga agaccccgag gtccagttca actggtacgt ggacggcgtg      840
gaggtgcata atgccaagac aaagccacgg gaggagcagt tcaacagcac gttccgtgtg      900
gtcagcgtcc tcaccgttgt gcaccaggac tggctgaacg gcaaggagta caagtgcaag      960
gtctccaaca aaggcctccc agcccccatc gagaaaacca tctccaaaac caaagggcag     1020
ccccgagaac cacaggtgta caccctgccc ccatcccggg aggagatgac caagaaccag     1080
gtcagcctga cctgcctggt caaaggcttc taccccagcg acatcgccgt ggagtgggag     1140
agcaatgggc agccggagaa caactacaag accacacctc ccatgctgga ctccgacggc     1200
tccttcttcc tctacagcaa gctcaccgtg gacaagagca ggtggcagca ggggaacgtc     1260
ttctcatgct ccgtgatgca tgaggctctg cacaaccact acacgcagaa gagcctctcc     1320
ctgtccccgg gtaaaggtgg aggaggatct ggaggaggag gaagtggagg tggaggatca     1380
catactcctg gaaatagcaa accaacacgc acaccaaggc gt                        1422
```

<210> SEQ ID NO 12
<211> LENGTH: 445
<212> TYPE: PRT
<213> ORGANISM: Artificial Sequence
<220> FEATURE:
<223> OTHER INFORMATION: Pnm Heavy Chain (Synthetic)

<400> SEQUENCE: 12

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140
```

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
            195                 200                 205

Ser Asn Thr Lys Val Asp Lys Thr Val Glu Arg Lys Cys Cys Val Glu
            210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Phe Arg Val Val Ser Val Leu
290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
            325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 13
<211> LENGTH: 1335
<212> TYPE: DNA
<213> ORGANISM: Artificial Sequence
<220> FEATURE:
<223> OTHER INFORMATION: Pnm Heavy Chain (Synthetic)

<400> SEQUENCE: 13
caggtgcagc tgcaggagtc cggccccggc ctggtgaagc cctccgagac cctgtccctg     60
acctgcaccg tgtccggcgg ctccgtgtcc tccggcgact actactggac ctggattcgg    120
cagtcccccg gcaagggcct ggagtggatc ggccacatct actactccgg caacaccaac    180
tacaacccct ccctgaagtc ccggctgacc atctccatcg acacctccaa gacccagttc    240
tccctgaagc tgtcctccgt gaccgccgcc gacaccgcca tctactactg cgtgcgggac    300
cgggtgaccg gcgccttcga catctggggc cagggcacca tggtgaccgt gtcctccgcc    360

```
tccaccaagg gcccatcggt cttccccctg gcgccctgct ccaggagcac ctccgagagc    420
acagcggccc tgggctgcct ggtcaaggac tacttccccg aaccggtgac ggtgtcgtgg    480
aactcaggcg ctctgaccag cggcgtgcac accttcccag ctgtcctaca gtcctcagga    540
ctctactccc tcagcagcgt ggtgaccgtg ccctccagca acttcggcac ccagacctac    600
acctgcaacg tagatcacaa gcccagcaac accaaggtgg acaagacagt tgagcgcaaa    660
tgttgtgtcg agtgcccacc gtgcccagca ccacctgtgg caggaccgtc agtcttcctc    720
ttccccccaa aacccaagga caccctcatg atctcccgga cccctgaggt cacgtgcgtg    780
gtggtggacg tgagccacga agaccccgag gtccagttca actggtacgt ggacggcgtg    840
gaggtgcata atgccaagac aaagccacgg gaggagcagt tcaacagcac gttccgtgtg    900
gtcagcgtcc tcaccgttgt gcaccaggac tggctgaacg gcaaggagta caagtgcaag    960
gtctccaaca aaggcctccc agcccccatc gagaaaacca tctccaaaac caaagggcag    1020
ccccgagaac cacaggtgta caccctgccc ccatcccggg aggagatgac caagaaccag    1080
gtcagcctga cctgcctggt caaaggcttc taccccagcg acatcgccgt ggagtgggag    1140
agcaatgggc agccggagaa caactacaag accacacctc ccatgctgga ctccgacggc    1200
tccttcttcc tctacagcaa gctcaccgtg gacaagagca ggtggcagca ggggaacgtc    1260
ttctcatgct ccgtgatgca tgaggctctg cacaaccact acacgcagaa gagcctctcc    1320
ctgtccccgg gtaaa                                                    1335
```

<210> SEQ ID NO 14
<211> LENGTH: 214
<212> TYPE: PRT
<213> ORGANISM: Artificial sequence
<220> FEATURE:
<223> OTHER INFORMATION: Pnm Light Chain (Synthetic)

<400> SEQUENCE: 14

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

Ala Cys Glu Val Thr His Gln Gly Leu Ser Ser Pro Val Thr Lys Ser
        195                 200                 205

Phe Asn Arg Gly Glu Cys
    210

<210> SEQ ID NO 15
<211> LENGTH: 642
<212> TYPE: DNA
<213> ORGANISM: Artificial Sequence
<220> FEATURE:
<223> OTHER INFORMATION: Pnm Light Chain  (Synthetic)

<400> SEQUENCE: 15

```
gacatccaga tgacccagtc tccatcctcc ctgtctgcat ctgtaggaga cagagtcacc      60
atcacttgcc aggcgagtca ggacatcagc aactatttaa attggtatca gcagaaacca     120
gggaaagccc ctaaactcct gatctacgat gcatccaatt tggaaacagg gtcccatca     180 aggttcagtg gaagtggatc tgggacagat tttactttca ccatcagcag cctgcagcct     240
gaagatattg caacatattt ctgccaacac tttgatcatc tcccgctcgc tttcggcgga     300
gggaccaagg tggagatcaa acgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gt                        642
```

<210> SEQ ID NO 16
<211> LENGTH: 100
<212> TYPE: PRT
<213> ORGANISM: Artificial Sequence
<220> FEATURE:
<223> OTHER INFORMATION: Linker  (Synthetic)
<220> FEATURE:
<221> NAME/KEY: REPEAT
<222> LOCATION: (1)..(5)
<223> OTHER INFORMATION: (GGGGS)n  wherein n = 1-20, some of the repeats
      may be absent

<400> SEQUENCE: 16

Gly Gly Gly Gly Ser Gly Gly Gly Gly Ser Gly Gly Gly Gly Ser Gly
1               5                   10                  15

Gly Gly Ser Gly Gly Gly Gly Ser Gly Gly Gly Gly Ser Gly Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser Gly Gly Gly Gly Ser Gly
                85                  90                  95

Gly Gly Gly Ser
            100